United States Patent
Mills et al.

(10) Patent No.: US 10,165,788 B2
(45) Date of Patent: Jan. 1, 2019

(54) METHODS AND COMPOSITIONS FOR IMPROVED DIGESTION OF MILK OLIGOSACCHARIDES

(71) Applicant: The Regents of the University of California, Oakland, CA (US)

(72) Inventors: David Mills, Davis, CA (US); Daniel Garrido, Santiago (CL); Santiago Ruiz-Moyano, Badajoz (ES); Carlito Lebrilla, Davis, CA (US); J. Bruce German, Davis, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 211 days.

(21) Appl. No.: 14/305,868

(22) Filed: Jun. 16, 2014

(65) Prior Publication Data

US 2015/0010670 A1 Jan. 8, 2015

Related U.S. Application Data

(60) Provisional application No. 61/836,046, filed on Jun. 17, 2013.

(51) Int. Cl.
*A61K 35/745* (2015.01)
*A23L 1/30* (2006.01)
*A23L 33/135* (2016.01)

(52) U.S. Cl.
CPC ............ *A23L 1/3014* (2013.01); *A23L 33/135* (2016.08); *A61K 35/745* (2013.01); *A23V 2002/00* (2013.01); *A23Y 2220/17* (2013.01); *A23Y 2220/63* (2013.01); *A23Y 2220/73* (2013.01); *A23Y 2300/19* (2013.01); *A23Y 2300/29* (2013.01); *A23Y 2300/31* (2013.01); *A23Y 2300/39* (2013.01); *A23Y 2300/55* (2013.01); *A23Y 2300/59* (2013.01)

(58) Field of Classification Search
CPC .................................................. A61K 35/745
See application file for complete search history.

(56) References Cited

U.S. PATENT DOCUMENTS

2010/0260720 A1* 10/2010 Sprenger .............. A61K 31/702
424/93.4
2013/0149342 A1* 6/2013 Mogna ................... A61K 35/74
424/282.1

OTHER PUBLICATIONS

BLAST Results of SEQ ID No. 5 versus the GenBank non-redundant protein database, search done Jul. 6, 2016 at http://blast.ncbi.nlm.nih.gov/Blast.cgi.*
BLAST Results of SEQ ID No. 1 versus the GenBank non-redundant protein database, search done Jul. 6, 2016 at http://blast.ncbi.nlm.nih.gov/Blast.cgi.*
GenBank Bifidobacterium breve Genome Assembly and Annotation Report downloaded from http://www.ncbi.nlm.nih.gov/genome/genomes/1273? on Jul. 6, 2016.*
GenBank Bifidobacterium longum Genome Assembly and Annotation Report downloaded from http://www.ncbi.nlm.nih.gov/genome/genomes/183? on Jul. 6, 2016.*
H. Ashida et al., "Two distinct α-L-fucosidases from Bifidobacterium bifidum are essential for the utilization of fucosylated milk oligosaccharides and glycoconjugates", Glycobiology 19(9):1010-1017 (2009).*
T. Katayama et al. Molecular Cloning and Characterization of Bifidobacterium bifidum1,2-α-L-Fucosidase (AfcA), a Novel Inverting Glycosidase (Glycoside Hydrolase Family 95), J. Bacteriology 186(15):4885-4893. (Aug. 2004).*
M.O. Motherway et al., "Functional genome analysis of Bifidobacterium breve UCC2003 reveals type IVb tight adherence (Tad) pili as an essential and conserved host-colonization factor", PNAS 108(27):11217-11222. (Jul. 2011).*
D.A. Sela et al. "The genome sequence of *Bifidobacterium longum* subsp. infantis reveals adaptations for milk utilization within the infant microbiome", PNAS 105(48):18964-18969 plus supporting information pp. 1-17.*
UniProt Accession No. D6ZY13 (Aug. 2010).*
CAZy—GH95,Glycoside Hydrolase Family 95,http://www.cazy.org/GH95_bacteria.html? pp. 2 and 3, retrieved May 10, 2017.*
CAZy—GH29,Glycoside Hydrolase Family 29, http://www.cazy.org/GH29_bacteria.html?, pp. 3 and 4, retrieved May 10, 2017.*
Y. Wei et al. "Safety Assessment of Bifidobacterium longum JDM301 Based on Complete Genome Sequences", World J. Gastroenterology, 18(5):479-488 (Feb. 2012).*
GenBank Accession No. ADG99808 (May 2010).*
GenBank Accession No. ALE12777 (Sep. 2015).*
GenBank Accession No. ALE12778 (Sep. 2015).*
GenBank Accession No. BAQ29966 (Oct. 2016).*
GenBank Accession No. BAQ29849 (Oct. 2016).*
J.S. Lee et al. "In Vitro Evaluation of Antimicrobial Activity of Lactic Acid Bacteriaagainst Clostridium difficile" Toxicology Research 29(2):99-106. (Jun. 12, 2013).*
H. Morita et al. "*Bifidobacterium kashiwanohense* sp. nov., isolated from healthy infant faeces", International Journal of Systematic and Evolutionary Microbiology 61:2610-2615. (2011).*
Chaplin et al., "Intraspecies Genomic Diversity and Long-Term Persistence of *Bifidobacterium longum*," PLOS One, 10(8): Aug. 14, 2015, 1-33.
Odamaki, et al. "Comparative genomics revealed genetic diversity and species/strain-level differences in carbohydrate metabolism of three probiotic bifidobacterial species." International journal of genomics 2015 (2015), 1-13.

* cited by examiner

*Primary Examiner* — Rebecca E Prouty
(74) *Attorney, Agent, or Firm* — Kilpatrick Townsend & Stockton LLP

(57) ABSTRACT

Pre-biotic compositions containing oligosaccharides and probiotic compositions useful for treatment of a subject are provided herein. Also provided are methods for administering probiotic or pre-biotic compositions.

9 Claims, 7 Drawing Sheets
Specification includes a Sequence Listing.

METHODS AND COMPOSITIONS FOR IMPROVED DIGESTION OF MILK OLIGOSACCHARIDES

CROSS-REFERENCES TO RELATED APPLICATIONS

This application claims priority to U.S. Provisional Appl. No. 61/836,046, filed Jun. 17, 2013, the disclosure of which is incorporated by reference in its entirety.

STATEMENT AS TO RIGHTS TO INVENTIONS MADE UNDER FEDERALLY SPONSORED RESEARCH AND DEVELOPMENT

This invention was made with Government support under Grant Nos. ATT007079, HD061923, and HD065122, awarded by the National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -2150-1.TXT, created on Jul. 23, 2014, 81,920 bytes, machine format IBM-PC, MS-Windows operating system, is hereby incorporated by reference in its entirety for all purposes.

BACKGROUND OF THE INVENTION

In addition to essential nutrients such as lactose lipids and proteins, human milk contains a large concentration of oligosaccharides. Human milk oligosaccharides (HMO) are complex and diverse molecules. These molecules are composed of glucose (Glc), galactose (Gal), N-acetylglucosamine (GlcNAc), and often contain fucose (Fuc) and/or N-acetylneuraminic acid (NeuAc), linked via several glycosidic bonds. The simplest oligosaccharides in human milk are trisaccharides where lactose can be sialylated to form sialyllactose, or fucosylated to form fucosyllactose. More complex HMO are also based on a lactose core that is conjugated with repeats of lacto-N-biose I (Galβ1-3GlcNAc; LNB; type-1 chain) or N-acetyllactosamine (Galβ1-4GlcNAc; type-2 chain), producing molecules with a degree of polymerization larger than 4 (Bode et al. (2012) *Adv. Nutr.* 3:383 S). These core structures can be modified by fucose and sialic acid residues via different linkages (De Leoz et al. (2012) *J. Proteome Res.* 11:4662). Although a large number of different HMO structures have been determined, a few isomers can represent up to 70% of the total molecules.

Remarkably, the energetic value of HMO for the infant is minimal. HMO are resistant to enzymatic hydrolysis from intestinal brush border membrane and pancreatic juices, and therefore the majority of these molecules transit the intestinal tract reaching the colon in intact form. During their transit HMO are believed to prevent pathoge colonization, by serving as decoy binding sites for epithelial glycans (Newburg et al. (2005) *Annu Rev. Nutr.* 25:37).

Human milk oligosaccharides (HMO) influence the composition of the intestinal microbiota in the first years of life. While the microbial community in breast-fed infants is largely dominated by the genus *Bifidobacterium*, formula-fed infants show increased bacterial diversity (Roger et al. (2010) *Microbiol.* 156:3329; Yatsunenko et al. (2012) *Nature* 486:222). This indicates that both pro- and antimicrobial elements in breast-milk account for these differences. A conceptual basis for co-evolution between bifidobacteria and milk glycans is supported by recent definition of the molecular mechanisms by which these microbes catabolize HMO. In *Bifidobacterium longum* subsp. *infantis* (*B. infantis*) ATCC 15697, these mechanisms include oligosaccharide transporters and intracellular glycosyl hydrolases (GH) such as fucosidases, hexosaminidases and sialidases (Gamido et al. (2012) *Adv. Nutr.* 3:415 S).

BRIEF SUMMARY OF THE INVENTION

Provided herein are methods for promoting growth of beneficial gut bacteria and/or increasing oligosaccharide consumption in an individual, comprising administering to the individual a composition comprising a bacterium that expresses heterologous alpha-fucosidase, thereby promoting growth of beneficial gut bacteria in the individual. In some embodiments, the heterologous alpha-fucosidase is GH-29. In some embodiments, the heterologous alpha-fucosidase is GH-95. In some embodiments, the bacterium is not *Bifidobacterium longum* subsp. *infantis* (*B. infantis*), or *B. bifidum*.

In some cases, the bacteria further expresses a second heterologous alpha-fucosidase. The second alpha-fucosidase can be GH-95 or GH-29. In some embodiments, the bacterium is selected from the group consisting of *Lactobacillus* and *Bifidobacterium*. In some embodiments, the *Lactobacillus* is selected from the group consisting of *L. casei, L. paracasei*, and *L. rhamnosus*. The *Bifidobacterium* can be selected from the group consisting of *B. adolescentis, B. catenulatum, B. pseudocatenulatum, B. dentium, B. longum*, and *B. breve*. In some embodiments, the bacterium is *Bifidobacterium breve* (*B. breve*).

In some embodiments, the method further comprises administering an oligosaccharide, e.g., an exogenous oligosaccharide. The oligosaccharide can be administered at the same time (e.g., in the same composition) or at a different time from the bacteria. The oligosaccharide can be a fucosylated oligosaccharide. In some embodiments, the composition comprises a milk oligosaccharide, a fucosylated milk oligosaccharide, or a human milk oligosaccharide. In some embodiments, the composition does not include an oligosaccharide containing an N-glycolylneuraminic acid residue.

In some embodiments, the oligosaccharide is selected from the group consisting of: an oligosaccharide consisting of 3 Hexose (Hex) moieties and 6 N-acetyl hexosamine (HexNAc) moieties; an oligosaccharide consisting of 4 Hex moieties and 3 HexNAc moieties; an oligosaccharide consisting of 3 Hex moieties and 4 HexNAc moieties; an oligosaccharide consisting of 6 Hex moieties and 2 HexNAc moieties; an oligosaccharide consisting of 3 Hex moieties, 4 HexNAc moieties and 1 fucose (Fuc) moiety; an oligosaccharide consisting of 4 Hex moieties and 4 HexNAc moieties; an oligosaccharide consisting of 3 Hex moieties and 5 HexNAc moieties; an oligosaccharide consisting of 4 Hex moieties, 4 HexNAc moieties, and 1 Fuc moiety; an oligosaccharide consisting of 5 Hex moieties and 4 HexNAc moieties; an oligosaccharide consisting of 3 Hex moieties, 5 HexNAc moieties, and 1 Fuc moiety; an oligosaccharide consisting of 4 Hex moieties and 5 HexNAc moieties; an oligosaccharide consisting of 3 Hex moieties and 6 HexNAc moieties; an oligosaccharide consisting of 5 Hex moieties, 4 HexNAc moieties, and 1 Fuc moiety; an oligosaccharide consisting of 4 Hex moieties, 5 HexNAc moieties, and 1 Fuc moiety; and an oligosaccharide consisting of 3 Hex moieties, 6 HexNAc moieties, and 1 Fuc moiety.

Further provided are compositions comprising a beneficial gut bacterial strain that expresses a heterologous alpha-fucosidase. In some embodiments, the alpha-fucosidase is GH-29 or GH-95. In some embodiments, the bacterial strain is not *Bifidobacterium longum* subsp. *infantis* (*B. infantis*) or *B. bifidum*. In some embodiments, the composition further comprising at least one oligosaccharide, such as a fucosylated oligosaccharide, a milk oligosaccharide, or a human milk oligosaccharide. In some cases the beneficial gut bacterial strain expresses at least two heterologous alpha-fucosidases. For example, the beneficial gut bacterial strain can express both GH-29 and GH-95.

In some embodiments, the composition includes a beneficial gut bacterial strain selected from the group consisting of *Lactobacillus* and *Bifidobacterium*. The *Lactobacillus* can be selected from the group consisting of *L. casei, L. paracasei*, and *L. rhamnosus*. The *Bifidobacterium* can be selected from the group consisting of *B. adolescentis, B. catenulatum, B. pseudocatenulatum, B. dentium, B. longum*, and *B. breve*. In some embodiments, the beneficial gut bacterial strain is *Bifidobacterium breve* (*B. breve*).

In some embodiments, the composition does not include an oligosaccharide containing an N-glycolylneuraminic acid residue. In some embodiments, the at least one oligosaccharide includes a milk oligosaccharide, a fucosylated oligosaccharide, or a human milk oligosaccharide.

In some embodiments, the at least one milk oligosaccharide is selected from the group consisting of: an oligosaccharide consisting of 3 Hexose (Hex) moieties and 6 N-acetyl hexosamine (HexNAc) moieties; an oligosaccharide consisting of 4 Hex moieties and 3 HexNAc moieties; an oligosaccharide consisting of 3 Hex moieties and 4 HexNAc moieties; an oligosaccharide consisting of 6 Hex moieties and 2 HexNAc moieties; an oligosaccharide consisting of 3 Hex moieties, 4 HexNAc moieties and 1 fucose (Fuc) moiety; an oligosaccharide consisting of 4 Hex moieties and 4 HexNAc moieties; an oligosaccharide consisting of 3 Hex moieties and 5 HexNAc moieties; an oligosaccharide consisting of 4 Hex moieties, 4 HexNAc moieties, and 1 Fuc moiety; an oligosaccharide consisting of 5 Hex moieties and 4 HexNAc moieties; an oligosaccharide consisting of 3 Hex moieties, 5 HexNAc moieties, and 1 Fuc moiety; an oligosaccharide consisting of 4 Hex moieties and 5 HexNAc moieties; an oligosaccharide consisting of 3 Hex moieties and 6 HexNAc moieties; an oligosaccharide consisting of 5 Hex moieties, 4 HexNAc moieties, and 1 Fuc moiety; an oligosaccharide consisting of 4 Hex moieties, 5 HexNAc moieties, and 1 Fuc moiety; and an oligosaccharide consisting of 3 Hex moieties, 6 HexNAc moieties, and 1 Fuc moiety.

Also provided are compositions comprising beneficial gut bacteria, wherein the bacteria express more than one heterologous alpha-fucosidase, the composition further comprising at least one oligosaccharide. In some embodiments, the bacteria are not *Bifidobacterium longum* subsp. *infantis* (*B. infantis*), or *B. bifidum*. In some embodiments, the more than one alpha-fucosidase includes GH-29. In some embodiments, the more than one alpha-fucosidase further includes GH-95. In some embodiments, the at least one oligosaccharide includes a fucosylated oligosaccharide. In some embodiments, the at least one oligosaccharide includes a milk oligosaccharide. In some embodiments, the at least one oligosaccharide includes a human milk oligosaccharide or a fucosylated human milk oligosaccharide.

In some embodiments, the beneficial gut bacteria are a strain selected from the group consisting of *Lactobacillus* and *Bifidobacterium*. The *Lactobacillus* can be selected from the group consisting of *L. casei, L. paracasei*, and *L. rhamnosus*. The *Bifidobacterium* can be selected from the group consisting of *B. adolescentis, B. catenulatum, B. pseudocatenulatum, B. dentium, B. longum*, and *B. breve*. In some cases, the beneficial gut bacterial strain is *Bifidobacterium breve* (*B. breve*).

Further provided are methods of administering any of the foregoing compositions. Fore example, in some embodiments, a method of promoting growth of beneficial gut bacteria and/or increasing oligosaccharide consumption in an individual, comprising administering any of the foregoing compositions to the individual. In some embodiments, administration is oral. In some embodiments, administration is rectal.

In addition, provided herein are methods for isolating a beneficial strain of *Bifidobacterium*. In some embodiments, the method comprises: screening a population of *Bifidobacterium* for presence of a nucleic acid sequence encoding GH-29 or GH-95 alpha-fucosidase; detecting the presence or absence of the nucleic acid encoding GH-29 or GH-95 alpha-fucosidase; and selecting a *Bifidobacterium* strain where the presence of the GH-29 or GH-95 nucleic acid is detected, thereby isolating a beneficial strain of *Bifidobacterium*. In some embodiments, the method comprises: screening a population of *Bifidobacterium* for presence of GH-29 or GH-95 alpha-fucosidase polypeptide; detecting the presence or absence of the GH-29 or GH-95 alpha-fucosidase polypeptide; and selecting a *Bifidobacterium* strain where the presence of the GH-29 or GH-95 polypeptide is detected, thereby isolating a beneficial strain of *Bifidobacterium*.

Also provided are methods of making a beneficial strain of *Bifidobacterium* comprising: transfecting a *Bifidobacterium* with an expression cassette comprising a heterologous polynucleotide encoding GH-29 or GH-95 operably linked to a promoter; and selecting for and isolating *Bifidobacterium* containing the expression cassette. In some cases, the *Bifidobacterium* is not a strain of *Bifidobacterium longum* subsp. *infantis* (*B. infantis*), or *B. bifidum*. In some cases, the *Bifidobacterium* is a strain of *Bifidobacterium breve* (*B. breve*).

Further provided are methods for promoting growth of beneficial gut bacteria in an individual, comprising administering to the individual a composition comprising a bacterium that expresses a first heterologous alpha-fucosidase and a second heterologous alpha-fucosidase, thereby promoting growth of beneficial gut bacteria in the individual. In some embodiments, the first or second alpha-fucosidase is GH-29. In other cases, the first or second alpha-fucosidase is GH-95. In some embodiments, the first alpha-fucosidase is GH-29 and the second alpha-fucosidase is GH-95.

DETAILED DESCRIPTION

I. Introduction

Figure 1:
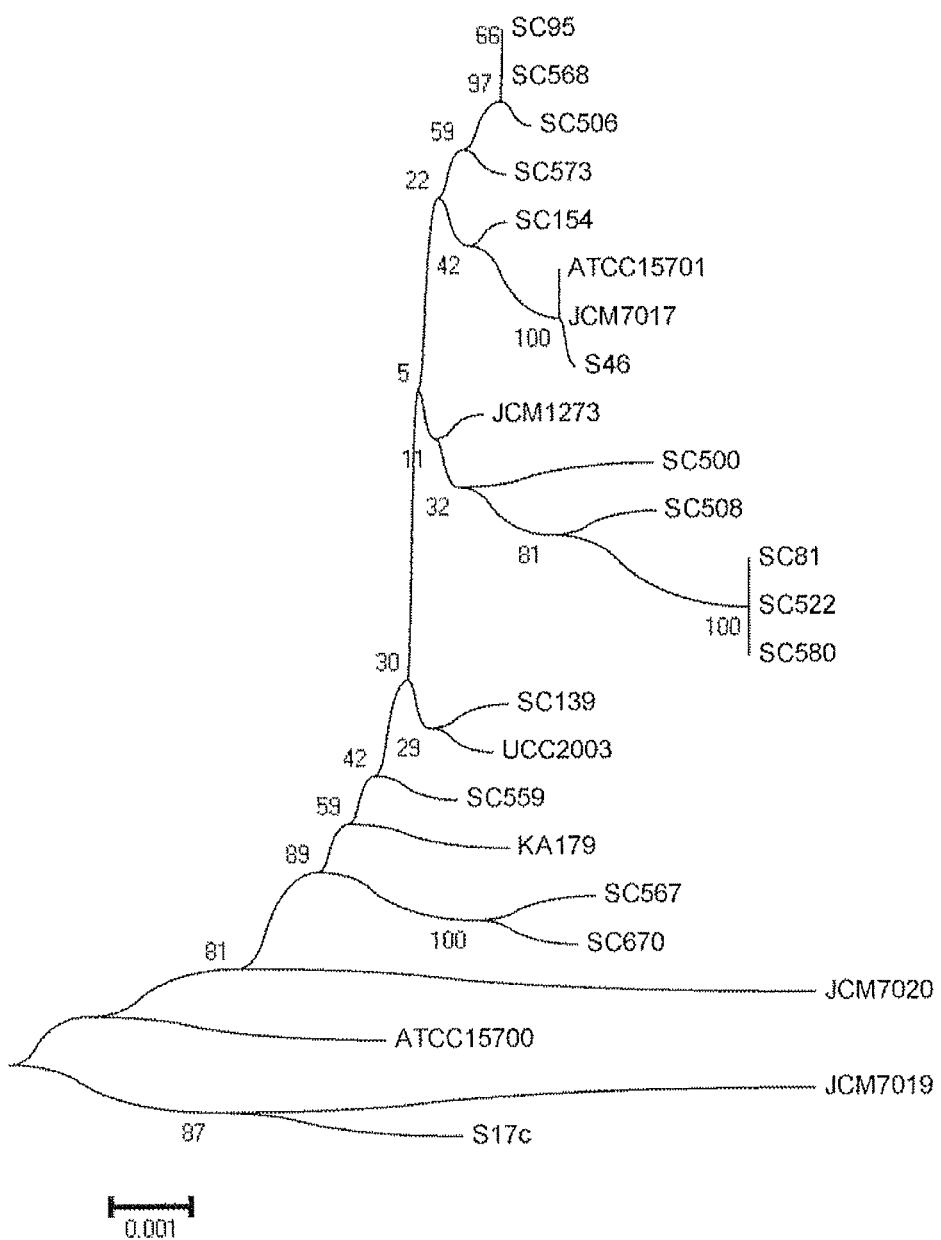
FIG. 1. Evolutionary relationship of *B. breve* strains used in the study. The tree is drawn to scale, with branch lengths in the same units (number of base substitutions per site) as those of the evolutionary distances used to infer the phylogenetic tree. The evolutionary history was inferred using the Minimum Evolution method, followed by 1000 bootstrap replicates.

Provided herein are strains of beneficial gut bacteria that express one or more glycohydrolases capable of hydrolyzing a human milk oligosaccharide, or structurally similar oligosaccharides. In some embodiments, the gut bacteria are genetically engineered, and express one or more heterologous polypeptides. In some embodiments, the gut bacteria express at least one heterologous glycohydrolase as described herein.

The present results show that certain glycohdrolases increase growth of beneficial gut bacteria on a human milk oligosaccharide (HMO) substrate. In some embodiments, alpha-fucosidases of the GH-29 family are associated with growth on HMO. In some embodiments, alpha-fucosidases of the GH-95 family are associated with growth on HMO. In some embodiments, bacteria that express multiple alpha-fucosidases (e.g., a GH-29 alpha-fucosidase and a GH-95 alpha-fucosidase) are capable of growing on human milk oligosaccharide, or structurally similar oligosaccharides.

The present results show that bacteria that express GH-29, express GH-95, or express multiple alpha-fucosidases (e.g., a GH-29 alpha-fucosidase and a GH-95 alpha-fucosidase), either endogenously or heterologously, can establish a beneficial microbiome in the gut of an individual to which HMO have been administered (e.g., a breastmilk-fed infant, or a human ingesting HMO). Alternatively, or in addition, administering HMO to a subject can be used to select for the establishment of a beneficial microbiome in the gut by selecting for beneficial bacteria that express GH-29, express GH-95, or express multiple alpha-fucosidases (e.g., a GH-29 alpha-fucosidase and a GH-95 alpha-fucosidase) in comparison to other microorganisms. Moreover, administering compositions of beneficial bacteria that express (e.g., heterologously) one or more of the glycohydrolases described herein, the composition further including a human milk oligosaccharide, can provide a therapeutic for, e.g. establishing a beneficial gut microbiome in a subject and selecting against for the growth of the beneficial gut bacteria in comparison to other microorganisms.

Disclosed herein is isolation of a representative number of strains of *Bifidobacterium*, and characterization of the molecular mechanisms for their consumption of milk oligosaccharides. *Bifidobacterium breve, B. infantis, B. longum* subsp. *longum* (*B. longum*), and *B. bifidum* are the species most frequently detected in breast-fed infant feces (Avershina et al. (2013) *Appl. And Env. Microbiol.* 79:497; Roger et al. (2010) *Microbiol.* 156:3329). In general, *B. breve* and *B. infantis* are more exclusively found in infants, and *B. longum* and *B. bifidum* are found in both infants and adults. While several strains of *B. bifidum* and *B. infantis* grow vigorously on HMO in vitro, this phenotype has been largely unexplored for larger numbers of *B. breve* and *B. longum* subsp. *longum* isolates. Only one strain of *B. breve*, ATCC 15700, was shown to utilize lacto-N-tetraose (LNT) primarily, contrasting with the versatility in HMO species consumption observed by *B. infantis* (Asakuma et al. (2011) *J. Biol. Chem.* 286:34583; LoCasio et al. (2007) *J. Agric. Food Chem.* 55:8914).

II. Definitions

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989); Any methods, devices and materials similar or equivalent to those described herein can be used in the practice of this invention.

The term "glycohydrolase" as used herein refers to an enzyme that catalyzes the hydrolysis of glycosides. Similarly, the term "alpha-fucosidase" as used herein refers to a glycohydrolase that is specific for, or substantially specific for, alpha-fucosides. Alpha-fucosidases include those enzymes found in glycoside hydrolase family 29 (GH-29) and glycoside hydrolase family 95 (GH-95). Exemplary glycohydrolases include SEQ ID NOs: 1-6, polypeptides encoded by SEQ ID NOs: 7-12, or polypeptides or nucleic acids substantially identical, or substantially similar, thereto.

As used herein, the term "oligosaccharide" refers to polymeric carbohydrates that contain 3 to 20 monosaccharides covalently linked through glycosidic bonds. In some embodiments, the oligosaccharides are purified from human milk, bovine milk, or the milk of any other suitable mammal. In some cases, the oligosaccharides are purified from whey, cheese, or other dairy products, e.g., purified away from oligosaccharide-degrading enzymes in milk, whey, cheese, or other dairy products. Purified oligosaccharides can be further modified as described herein. Alternatively, the oligosaccharides can be synthesized or partially synthesized (e.g., synthesized from a purified oligosaccharide starting material) as described herein. Compositions described herein can include a mixture of oligosaccharides that have been purified, partially synthesized, or synthesized.

The term human milk oligosaccharide (HMO) can refer to a number of complex oligosaccharides found in human milk, or oligosaccharides that are structurally similar to, or structurally identical to oligosaccharides found in human milk. Consequently, HMO need not be derived from human milk or human milk products and can be partially synthesized, synthesized de novo, or derived from the milk of another organism. HMO compositions can include mixtures of oligosaccharides that have been purified, partially synthesized, or synthesized. HMO compositions further include chemically modified oligosaccharides found in human milk, or oligosaccharides that are structurally similar to, or structurally identical to oligosaccharides found in human milk as described herein. Human milk oligosaccharides can, in some embodiments, include fucosyl oligosaccharides.

Among the monomers of milk oligosaccharides are D-glucose (Glc), D-galactose (Gal), N-acetylglucosamine (GlcNAC), L-fucose (Fuc), and sialic acid [N-acetylneuraminic acid (NeuAc)]. Elongation may be achieved by attachment of GlcNAc residues linked in β1-3 or β1-4 linkage to a Gal residue followed by further addition of Gal in a β-1-3 or β-1-4 bond. Most HMOs carry lactose at their reducing end. From these monomers, a large number of core structures may be formed. Further variations may occur due to the attachment of lactosamine, Fuc, and/or NeuAc. See, e.g., Kunz, C. et al., Annual. Rev. Nutri., 20:699-722 (2000) for a further description of HMOs. Human milk oligosaccharides can also be found in, or purified from, the milk of other mammals, provided that they are identical or substantially identical to the human milk oligosaccharides.

Hexose (Hex) represents a residue of glucose or galactose or mannose.

Fucose (Fuc) represents a residue of Deoxyhexose.

HexNAc represents a residue of N-acetylglucosamine or N-acetylgalactosamine.

NeuAc represents a residue of N-acetyl neuraminic acid (sialic acid).

The term "*Bifidobacterium*" and its synonyms refer to a genus of anaerobic bacteria having beneficial properties for humans. Bifidobacteria is one of the major genera of bacteria that make up the gut flora, the bacteria that reside in the gastrointestinal tract and have health benefits for their hosts. See, e.g., Guarner F and Malagelada J R. *Lancet* (2003) 361, 512-519, for a further description of *Bifidobacterium* in the normal gut flora.

The term "beneficial gut bacteria" or the like refers to live microorganisms that reside in the gut or can be introduced into the gut of an individual and confer a health benefit on the host. In some cases, the beneficial gut bacteria can aid in the digestion of carbohydrates, proteins, or fatty acids that are not efficiently digested, or not digested at all, by the host. In some cases, the beneficial gut bacteria generate metabolites that are beneficial to the host such as fatty acids, vitamins, or modulators of the immune system. In some cases, the beneficial gut bacteria inhibit the growth of pathogenic bacteria in the gut.

Exemplary embodiments of beneficial gut bacteria include lactobacilli (e.g., *L. casei, L. paracasei*, and *L. rhamnosus*) and bifidobacteria (e.g., *B. adolescentis, B. catenulatum, B. pseudocatenulatum, B. dentium, B. bifidum, B. longum, B. infantis*, and *B. breve*). Exemplary embodiments of beneficial gut bacteria further include, but are not limited to, the foregoing lactobacilli and bifidobacteria that express an alpha-fucosidase such as GH-29, or an alpha-fucosidase such as GH-95. In some cases, the beneficial gut bacteria further include, but are not limited to, the foregoing bifidobacteria and bifidobacteria that express at least two alpha-fucosidases. For example, beneficial gut bacteria further include, but are not limited to, Lactobacilli and Bifidobacteria that express GH-29 and GH-95.

A "prebiotic" or "prebiotic nutrient" is generally a non-digestible food ingredient that beneficially affects a host when ingested by selectively stimulating the growth and/or the activity of one or a limited number of bacteria in the gastrointestinal tract, e.g., beneficial gut bacteria. As used herein, the term "prebiotic" refers to the above described non-digestible food ingredients in their non-naturally occurring states, e.g., after purification, chemical or enzymatic synthesis as opposed to, for instance, in whole human milk. Pre-biotics can be administered separately from beneficial gut bacteria, or in conjunction with beneficial gut bacteria. As used herein, "in conjunction with" refers to at the same time as, substantially the same time as, about 1, 2, 3, 4, 5, 6, 7, 8, 9, 10, 15, 20, 30, 45, or 60 minutes before or after, about 1, 2, 3, 4, 5, 6, 7, 8, 9, 10, 15, 20, 30 hours before or after, or about 1 or 2 days before or after the administration of gut bacteria.

A "probiotic" refers to beneficial gut bacteria that when administered in adequate amounts confer a health benefit on the host.

An "expression cassette" refers to a nucleic acid construct, which when introduced into a host cell (e.g., a microorganism, such as a *Bifidobacterium* or a *Lactobacillus*), results in transcription and/or translation of a RNA or polypeptide, respectively. An expression cassette typically includes a sequence to be expressed, and sequences necessary for expression of the sequence to be expressed. The sequence to be expressed can be a coding sequence or a non-coding sequence (e.g., an inhibitory sequence). The sequence to be expressed is generally operably linked to a promoter. The promoter can be a heterologous promoter or a promoter that is derived from the host plant. Generally, an expression cassette is inserted into an expression vector to be introduced into a host cell. The expression vector can be viral or non-viral.

"Recombinant" refers to a human manipulated polynucleotide or a copy or complement of a human manipulated polynucleotide. For instance, a recombinant expression cassette comprising a promoter operably linked to a second polynucleotide may include a promoter that is heterologous to the second polynucleotide as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). A recombinant expression cassette may comprise polynucleotides combined in such a way that the polynucleotides are extremely unlikely to be found in nature. For instance, human manipulated restriction sites or plasmid vector sequences may flank or separate the promoter from the second polynucleotide. One of skill will recognize that polynucleotides can be manipulated in many ways and are not limited to the examples above. A recombinant protein is one that is expressed from a recombinant polynucleotide, and recombinant cells, tissues, and organisms are those that comprise recombinant sequences (polynucleotide and/or polypeptide).

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from naturally-occurring variants.

The term "exogenous," in reference to a polypeptide or polynucleotide, refers to polypeptide or polynucleotide which is introduced into a cell or organism (e.g., a microorganism, such as a *Bifidobacterium* or a *Lactobacillus*) by any means other than by mating.

The term "transgenic," e.g., a transgenic microorganism, such as a transgenic *Bifidobacterium* or *Lactobacillus*, refers to a recombinantly modified organism with at least one introduced genetic element. The term is typically used in a positive sense, so that the specified gene is expressed in the transgenic organism. However, a transgenic organism can be transgenic for an inhibitory nucleic acid, i.e., a sequence encoding an inhibitory nucleic acid is introduced. The introduced polynucleotide can be from the same species or a different species, can be endogenous or exogenous to the organism, can include a non-native or mutant sequence, or can include a non-coding sequence.

In the case of both expression of transgenes and inhibition of endogenous genes (e.g., by antisense, or sense suppression) one of skill will recognize that a polynucleotide sequence need not be identical and can be "substantially identical" to a sequence of the gene from which it was derived.

The term "promoter" refers to regions or sequence located upstream and/or downstream from the start of transcription and which are involved in recognition and binding of RNA polymerase and other proteins to initiate transcription. A "bacterial promoter" is a promoter capable of initiating transcription in bacterial cells (e.g., *Bifidobacterium* or *Lactobacillus*). In some cases, a bacterial promoter can originally derive from the same species of microorganism into which it is introduced. In other cases, a bacterial promoter may derived from another species of bacteria or from another organism (e.g., a viral, fungal, plant, animal, or mammalian promoter) that is capable of initiating transcription in bacterial cells.

A "constitutive promoter" refers to a promoter that is capable of initiating transcription under nearly all conditions, whereas an "inducible promoter" initiates transcription under specific conditions such as the presence of an inducer (e.g., allolactose, arabinose, tryptophan, IPTG) or a signal (e.g., heat, cold, low phosphate,). In some embodiments, a promoter is inducible if the transcription levels initiated by the promoter under a specific cellular condition are at least 2-fold, 3-fold, 4-fold, 5-fold, 6-fold, 7-fold, 8-fold, 9-fold, 10-fold, 50-fold, 100-fold, 500-fold, 1000-fold higher or more as compared to the transcription levels initiated by the promoter in the absence of that condition.

The term "express," "expresses," "expressing," or the like, as in "a bacterium that expresses" refers to a bacterium that has polynucleotide encoding a specific gene (e.g., a glycohydrolase such as an alpha-fucosidase, including GH-29 or GH-95) that is capable of being expressed. In some cases, the gene can express constitutively. In other cases, the gene can be expressed only under certain conditions (e.g., it is inducible).

The term "modulate" as in to "modulate a gene" or "modulate expression" of a gene refers to increasing or decreasing the expression, activity, or stability of a gene. For example, a gene may be modulated by increasing or decreasing the amount of RNA that is transcribed from the gene or altering the rate of such transcription. Decreased expression may include expression that is reduced by 5%, 10%, 15%, 20%, 25%, 30%, 50%, 75%, 80%, 90%, 95%, 99% or more. Increased expression, or over expression, includes expression that is increased by 1%, 1.5%, 2%, 3%, 4%, 5%, 6%, 7%, 8%, 9%, 10%, 12%, 15%, 17%, 20%, 25%, 30%, 35%, 40%, 50%, 60%, 70%, 80%, 90%, 100%, or more. In some cases expression may be increased by at least 2-fold, 3-fold, 4-fold, 5-fold, 6-fold, 7-fold, 8-fold, 9-fold, 10-fold, 50-fold, 100-fold, 500-fold, 1000-fold higher. Expression may be modulated in a constitutive or inducible manner as provided herein.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The term "substantial identity" of polynucleotide sequences means that a polynucleotide comprises a sequence that has at least 25% sequence identity. Alternatively, percent identity can be any integer from at least 25% to 100% (e.g., at least 25%, 26%, 27%, 28%, . . . , 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%), preferably calculated with BLAST using standard parameters, as described below. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Percent identity of polypeptides can be any integer from at least 40% to 100% (e.g., at least 40%, 41%, 42%, 43%, . . . , 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%). In some embodiments, substantially identical polypeptide share at least 70%, 75%, 80%, 85%, 90%, 95%, or 99%.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amidecontaining side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Unless otherwise indicated, the comparison window extends the entire length of a reference sequence. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions.

III. Glycohydrolases

Alpha-Fucosidases

Described herein are alpha-fucosidases (e.g., GH-29 or GH-95 family glycohydrolases) that are capable of hydrolyzing components of human milk oligosaccharides, and other saccharides of similar structure. The GH-95 and GH-29 alpha-fucosidases play a role in degrading α1,2- and α1,3/4-fucosylated milk oligosaccharides, respectively, and also glycoconjugates, in the gut of host organisms. The glycohydrolases can be expressed in bacteria (e.g., beneficial gut bacteria) and confer the ability of the bacteria to hydrolyze components of oligosaccharides (e.g., milk oligosaccharides, or human milk oligosaccharides). In some cases, the glycohydrolases can thus confer the ability of the bacteria to utilize oligosaccharides (e.g., milk oligosaccharides, or human milk oligosaccharides) as a carbon and/or nitrogen source. In some cases, this can provide a selective advantage as compared to other microorganisms present.

Alpha-fucosidases hydrolize fucosides to fucose. See, e.g., Levvy, G. A. and McAllan, A. Mammalian fucosidases. 2. alpha-L-Fucosidase. Biochem. J. 80 (1961) 435-439. Glycohydrolases of the GH-29 family are exo-acting alpha-fucosidases found in archaea, bacteria, and eukarya. In some cases, the GH-29 alpha-fucosidases herein are of bacterial origin. However, in other cases, they can be of from an organism of any phylogenetic kingdom as long as they can be expressed in a beneficial gut bacteria.

In some embodiments, GH-29 alpha-fucosidases (E.C. number 3.2.1.51) described herein can specifically release α-1,3- and α-1,4-linked fucosyl residues from 3-fucosyllactose, various Lewis blood group substances (a, b, x, and y types), and lacto-N-fucopentaose II and III. In some cases, GH-29 alpha-fucosidases described herein can cleave fucose from LNFPIII (α1-3). In some cases, GH-29 alpha-fucosidases described herein do not show activity on small oligosaccharides (2FL and 3FL), glycoconjugates containing α-1,2-fucosyl residue, or on synthetic α-fucoside (p-nitrophenyl-α-1-fucoside). In some cases, the GH-29 alpha-fucosidases described herein exhibit a greater activity against longer-chain fucosylated oligosaccharides. GH-29 alpha-fucosidases described herein can confer the ability of gut bacteria to utilize, e.g. oligosaccharides, milk oligosaccharides, human milk oligosaccharides, fucosyl oligosaccharides, 3-fucosyllactose, or lacto-N-fucopentaose II as a carbon source (e.g., as a sole carbon source).

Exemplary GH-29 alpha-fucosidases include a fucosidase domain. In some cases, the GH-29 alpha-fucosidases include additional domains such as a carbohydrate binding domain. In some cases, exemplary fucosidases can also include a FIVAR domain, and/or a transmembrane domain. Consequently, in some cases, the GH-29 alpha-fucosidases, can be expressed (e.g., heterologously expressed) as fragment polypeptides such that the catalytic activity and growth on HMO phenotype are preserved, but non-essential domains or fragments are removed or replaced. The essential features of GH-29 alpha-fucosidases are known in the art and are described in, e.g. Ashida et al., Glycobiology, 19(9), 1010-17 (2009); and Sela et al., Applied and Enviromental Microbiology, 78, 795-803 (2012).

Similarly, GH-95 glycohydrolases are 1,2-alpha-L-fucosidases which hydrolyze Fucα1-2Gal linkages at the non-reducing end of an oligosaccharide. In some cases, a GH-95 glycohydrolase as used herein cannot hydrolyze the fucoysl linkage when the Gal residue is further modified. In some cases, the GH-95 glycohydrolases provided herein are predicted to cleave α1-2, α1-3, 2FL, 3FL, and Fucα1-2Gal substrates. GH-95 alpha-fucosidases described herein can confer the ability of gut bacteria to utilize, e.g. oligosaccharides, milk oligosaccharides, human milk oligosaccharides, or fucosyl oligosaccharides as a carbon source (e.g., as a sole carbon source).

Exemplary GH-95 alpha-fucosidases can include an N-terminal domain, a catalytic domain and/or an Ig-like domain. Consequently, in some cases, the GH-95 alpha-fucosidases, are expressed (e.g., heterologously expressed) as fragment polypeptides such that the catalytic activity and growth on HMO phenotype are preserved, but non-essential domains or fragments are removed or replaced. The essential features of GH-95 alpha-fucosidases are known in the art and are described in, e.g., Katayama, et al., Journal of Bioscience and Bioengineering, 99(5), 457-65 (2005); and Sela et al., Applied and Enviromental Microbiology, 78, 795-803 (2012).

Provided herein are bacterial alpha-fucosidase polypeptides (e.g., any of GH-29: SEQ ID NOs: 1-4 or GH-95: SEQ ID NOs: 5 or 6) and polynucleotides encoding such polypeptides (e.g., any of SEQ ID NOs: 7-10, and 11 or 12 respectively).

Also described herein are polypeptides substantially identical to the sequences exemplified herein, polynucleotides and expression cassettes encoding such alpha-fucosidase polypeptides or a mutation or fragment thereof, and vectors or other constructs for alpha-fucosidase polypeptide expression in a microorganism (e.g., a *Bifidobacterium* or a *Lactobacillus*). Also described herein are polypeptides which are substantially similar to the exemplified sequences (e.g., SEQ ID NOs: 1-6). Polypeptides which are "substantially similar" share sequences as noted above except that residue positions which are not identical may differ by conservative amino acid changes.

Polynucleotides that selectively hybridize to, and/or are substantially identical to, one of SEQ ID NOs: 7-12 are also provided herein. The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA). Polynucleotides that selectively hybridize to any one of SEQ ID NOs: 7-12 can be of any length, e.g., at least 10, 15, 20, 25, 30, 50, 100, 200 500 or more nucleotides or having fewer than 500, 200, 100, or 50 nucleotides, etc.

Other Glycohydrolases

Provided herein are other glycohydrolases that are capable of hydrolyzing components of human milk oligosaccharides, and other saccharides of similar structure. The glycohydrolases can be expressed in bacteria (e.g., beneficial gut bacteria) and confer the ability of the bacteria to hydrolyze components of human milk oligosaccharides and other saccharides of similar structure. In some cases, the glycohydrolases can thus confer the ability of the bacteria to utilize the human milk oligosaccharides as a carbon and/or nitrogen source. In some cases, this can provide a selective advantage as compared to other microorganisms present.

For example, bacteria expressing glycohydrolases capable of hydrolyzing components of human milk oligosaccharides can grow more quickly, or become a larger portion of the microbiome in the gut of a subject that is consuming human milk oligosaccharides, as compared to bacteria that do not express such glycohydrolases. In some embodiments, this selective advantage can be utilized by providing glycohydrolases capable of hydrolyzing components of human milk oligosaccharides to bacteria known or suspected of being beneficial. In other cases, bacteria known or suspected of being beneficial can be assayed to determine their glycohydrolases and thus an pre-biotic composition or formulation can be applied to select for the beneficial bacteria.

Glycohydrolases described herein include alpha-sialidases, beta-galactosidases, beta-hexaminidases, and alpha-fucosidases. Alpha-sialidases (EC:3.2.1.18 COG4409) are enzymes which catalyze the hydrolysis of alpha-(2->3)-, alpha-(2->6)-, alpha-(2->8)-glycosidic linkages of terminal sialic acid residues in oligosaccharides, glycoproteins, glycolipids, colominic acid, and synthetic substrates. Members of this family contain multiple BNR (bacterial neuraminidase repeat) repeats or Asp-boxes. The repeats are short, however the repeats are never found closer than 40 residues together suggesting that the repeat is structurally longer. These repeats are found in a variety of non-homologous proteins, including bacterial ribonucleases, sulphite oxidases, reelin, netrins, sialidases, neuraminidases, some lipoprotein receptors, and a variety of glycosyl hydrolases. See, e.g., Schauer, R. Sialic acids. Adv. Carbohydr. Chem. Biochem. 40 (1982) 131-234.

Beta-galactosidase (EC: 3.2.1.23 COG1874) catalyzes hydrolysis of terminal non-reducing beta-D-galactose residues in beta-D-galactosides. This class comprises a widespread group of enzymes that hydrolyze the glycosidic bond between two or more carbohydrates, or between a carbohydrate and a non-carbohydrate moiety. A classification system for glycosyl hydrolases, based on sequence similarity, has led to the definition of 85 different families. See, e.g., Kuby, S. A. and Lardy, H. A. Purification and kinetics of beta-D-galactosidase from *Escherichia coli*, strain K-12. J. Am. Chem. Soc. 75 (1953) 890-896.

N-acetyl-beta-hexosaminidase (EC:3.2.1.52 COG3525) catalyzes the hydrolysis of terminal non-reducing N-acetyl-D-hexosamine residues in N-acetyl-beta-D-hexosaminides. This class comprises a widespread group of enzymes that hydrolyze the glycosidic bond between two or more carbohydrates, or between a carbohydrate and a non-carbohydrate moiety. See, e.g., Isolation of beta-N-acetylhexosaminidase, beta-N-acetylglucosaminidase, and beta-N-acetylgalactosaminidase from calf brain. Biochemistry. 6 (1967) 2775-82.

IV. Beneficial Gut Bacteria

As described herein, beneficial gut bacteria include those that reside in the gut of an individual or can be introduced into the gut of an individual (e.g., are capable of growth in the gut without pathogenesis) and confer a health benefit. In some embodiments, the beneficial gut bacteria express an alpha-fucosidase, such as GH-29. In other embodiments, the beneficial gut bacteria express a GH-95 alpha-fucosidase. In some cases, the beneficial bacteria express at least two alpha-fucosidases, such as a GH-29 and a GH-95 alpha-fucosidase. The alpha-fucosidases can be endogenous glycohydrolases, i.e., the glycohydrolases occur naturally in the strain. In other cases, at least one (e.g., 1, 2, 3, or 4) of the alpha-fucosidases are heterologous. In some cases, the heterologous gene is introduced as a recombinant expression cassette, and the beneficial gut bacteria is transgenic. In other cases, the heterologous gene is introduced by a natural process, such as bacterial mating, and the beneficial gut bacteria expresses a heterologous gene and yet the bacteria is not transgenic.

In general, beneficial gut bacteria are selected from species that are normally found in the gut of a human infant, a breast-fed human infant, a formula-fed human infant (e.g., a milk, soy, or corn based formula), an adolescent, an adult, or a cow or other animal. Beneficial gut bacteria are selected from species of bacteria that do not cause pathogenesis in the host organism. In some embodiments, the beneficial gut bacteria are selected from species of bacteria that are only opportunistically pathogenic in cases of immune-deficiency or autoimmune disease. Beneficial gut bacteria include lactobacilli and bifidobacteria.

In some embodiments, the beneficial gut bacteria can metabolize carbohydrates that cannot be digested by the host, such as one or more oligosaccharides (e.g., milk oligosaccharides, or human milk oligosaccharides). For example, the beneficial gut bacteria can express a GH-29 alpha-fucosidase, a GH-95 alpha-fucosidase, or multiple alpha-fucosidases (e.g., a GH-29 and a GH-95 alpha-fucosidase) and thus be capable of digesting one or more oligosaccharides (e.g., milk oligosaccharides, or human milk oligosaccharides). In some embodiments, the beneficial gut bacteria can generate metabolites that serve as nutrients for the host, serve an immunomodulatory function (e.g., reduce inflammation or stimulate mucosal epithelium), or signal the enteric nervous system. In still other embodiments, the beneficial gut bacteria regulate epithelial cell turnover, promote epithelial restitution, and/or reorganize tight junctions in the gut epithelium.

In some cases, the beneficial bacteria produce a conjugated linoleic acid or convert a conjugated linoleic acid. Conjugated linoleic acids are a family of linoleic acid isomers. Conjugated linoleic acids can be converted to linoleic acid or alpha-L-linoleic acid by bacterial strains in the gut. Inability of the gut microbiome to convert conjugated linoleic acids has been associated with digestive diseases, gluten sensitivity and/or dysbiosis. Dysbiosis is associated with inflammatory bowel disease and chronic fatigue syndrome. Described herein are methods of providing a gut microbiome (or a component thereof) to a subject in need thereof that is capable of producing or converting a conjugated linoliec acid.

V. Oligosaccharides

In some embodiments, GH-29 and/or GH-95 expressing bacteria as described herein are formulated with or administrated in conjunction with an oligosaccharide. Oligosaccharides described herein include human milk oligosaccharides (HMO) and oligosaccharides of a similar structure. In some embodiments, the oligosaccharides include those that are not digestible, or not substantially digestible, in a human gut without the aid of beneficial gut bacteria. Oligosaccharides herein include galacto-oligosaccharides (GOS) and oligosaccharides derived from a mammal such as a cow, a goat, a sheep, a horse, a buffalo, or a yak. In some embodiments, oligosaccharide containing compositions are administered to a subject in order to select for the growth and/or colonization of beneficial bacteria in the gut.

Human milk oligosaccharides (HMO) include, e.g., those described in U.S. Pat. No. 8,197,872. Human milk oligosaccharide compositions include compositions containing one or more of the following: Lacto-N-Tetraose, Lacto-N-Neotetraose, Lacto-N-Fucopentaose I, Lacto-N-Fucopentaose II, Lacto-N-Fucopentaose III, Lacto-N-Fucopentaose V, Lacto-N-Hexaose, Para-Lacto-N-Hexaose, Lacto-N-Neohexaose, Para-Lacto-N-Neohexaose, Monofucosyllacto-N-Hexaose II, Isomeric Fucosylated Lacto-N-Hexaose (1), Monofucosyllacto-N-Hexaose, Isomeric Fucosylated Lacto-N-Hexaose (3), Isomeric Fucosylated Lacto-N-Hexaose (2), Difucosyl-Para-Lacto-N-Neohexaose, Difucosyl-Para-Lacto-N-Hexaose, Difucosyllacto-N-Hexaose, Lacto-N-

Neoocataose, Para-Lacto-N-Octanose, Iso-Lacto-N-Octaose, Lacto-N-Octaose, Monofucosyllacto-Nneoocataose, Monofucosyllacto-N-Ocataose, Difucosyllacto-N-Octaose I, Difucosyllacto-N-Octaose II, Difucosyllacto-N-Neoocataose II, Difucosyllacto-N-Neoocataose I, Lacto-N-Decaose, Trifucosyllacto-N-Neooctaose, Trifucosyllacto-N-Octaose, and Trifucosyl-Iso-Lacto-N-Octaose. In some cases, HMO compositions can contain at least two or more of the foregoing oligosaccharides (e.g., 3, 4, 5, 6, 7, 8, 9, or more).

The HMOs described herein can be derived using any of a number of sources and methods known to those of skill in the art. For example, HMOs can be purified from human milk using methods known in the art. One such method for extraction of oligosaccharides from pooled milk entails the centrifugation of milk at 5,000×g for 30 minutes at 4° C. and fat removal. Ethanol can then be added to precipitate proteins. After centrifugation to sediment precipitated protein, the resulting solvent can be collected and dried by rotary evaporation. The resulting material can be adjusted to the appropriate pH (e.g., 6.8) with, for example, a phosphate buffer, and β-galactosidase can be added. After incubation, the solution can be extracted with chloroform-methanol, and the aqueous layer collected. Monosaccharides and disaccharides can removed by selective adsorption of HMOs using solid phase extraction with graphitized nonporous carbon cartridges. The retained oligosaccharides can be eluted with, e.g., water-acetonitrile (60:40) with 0.01% trifluoroacetic acid. (See, e.g., Ward et al., Appl. Environ. Microbiol. (2006), 72: 4497-4499; Gnoth et al., J. Biol. Chem. (2001), 276:34363-34370; Redmond and Packer, Carbohydr. Res., (1999), 319:74-79.) Individual HMOs can be further separated using methods known in the art such as capillary electrophoresis, HPLC (e.g., high-performance anion-exchange chromatography with pulsed amperometric detection; HPAEC-PAD), and thin layer chromatography. See, e.g., Splechtna et al., J. Agricultural and Food Chemistry (2006), 54: 4999-5006.

Alternatively, enzymatic methods can be used to synthesize the HMOs described herein. In general, any oligosaccharide biosynthetic enzyme or catabolic enzyme (with the reaction running in reverse) that converts a substrate into any of the HMO oligosaccharides (or their intermediates) may be used. For example, prebiotic galacto-oligosaccharides have been synthesized from lactose using the β-galactosidase from L. reuteri (See, Splechtna et al., J. Agricultural and Food Chemistry (2006), 54: 4999-5006). The reaction employed is known as transgalactosylation, whereby the enzyme β-galactosidase hydrolyzes lactose, and, instead of transferring the galactose unit to the hydroxyl group of water, the enzyme transfers galactose to another carbohydrate to result in oligosaccharides with a higher degree of polymerization (Vandamme and Soetaert, FEMS Microbiol. Rev. (1995), 16:163-186). The transgalactosylation reaction can proceed intermolecularly or intramolecularly. Intramolecular or direct galactosyl transfer to D-glucose yields regioisomers of lactose. Through intermolecular transgalactosylation di-, tri-, and tetra saccharides and eventually higher oligosaccharides specific to Bifidobacteria are produced. A related method utilizes the β-galactosidase of Bifidobacterium bifidum NCIMB 41171 to synthesize prebiotic galacto-oligosaccharides (See, Tzortzis et al., Appl. Micro. and Biotech. (2005), 68:412-416).

Another approach to the synthesis of the carbohydrates of the invention that combines elements of the methods outlined above entails the chemical or enzymatic synthesis of or isolation of oligosaccharide backbones containing Lacto-N-biose, or Lacto-N-tretrose from non-human mammalian milk sources (e.g., cows, sheep, buffalo, goat, horse, yak, etc.) and enzymatically adding Lacto-N-biose, Fucose and Sialic Acid units as necessary to arrive at the HMO. For this purpose, a variety of bifidobacterial carbohydrate modifying enzymes, such as those disclosed in PCT Publication WO 2008/033520 can be utilized. Examples of such oligosaccharide modifying enzymes include sialidases, silate O-Acetylesterases, N-Acetylneuraminate lyases, N-acetyl-beta-hexosaminidase, beta-galactosidases, N-acetylmannosamine-6-phosphate 2-epimerases, alpha-L-fucosidases, and fucose dissimilation pathway proteins, among others, which may be used to catalyze a biosynthetic reaction under the appropriate conditions.

Alternatively, conventional chemical methods may be used for the de novo organic synthesis of or conversion of pre-existing oligosaccharides into the HMO oligosaccharides described herein. See, e.g., March's Advanced Organic Chemistry: Reactions, Mechanisms, and Structure, 5th Edition.

Galacto-oligosaccharide (GOS) compositions include, e.g., those described in U.S. Pat. No. 8,425,930. GOS are naturally occurring in human milk, however, commercial GOS preparations are often produced by enzymatic treatment of lactose with β-galactosidases from different sources such as fungi, yeast and/or bacteria, yielding a mixture of oligomers with varied chain lengths (Angus, F., Smart, S, and Shortt, C. 2005. In Probiotic Dairy Products ed. Tamine, A. pp. 120-137. Oxford: Blackwell Publishing). Thus, the basic structure of GOS includes a lactose core at the reducing end which is elongated typically with up to six galactose residues. GOS structural diversity dependents on the enzyme used in the trans-galactosylation reaction, and the experimental conditions such as pH and temperature (Dumortier, V., et al. 1990. Carbohydr Res 201:115-23.).

In some embodiments, GOS compositions herein include those with a relatively high degree of polymerization (DP). The "DP" of a GOS refers to the total number of sugar monomer units that are part of a particular oligosaccharide. For example, a tetra GOS has a DP of 4, having 3 galactose moieties and one glucose moiety. In some cases, the GOS compositions include a GOS that has been enriched for DP 4-5 galacto-oligosaccharides, a GOS that has been enriched for DP 6-8 galacto-oligosaccharides, and a GOS that has been enriched for DP 3 galacto-oligosaccharides. Exemplary levels of enrichment can include GOS that contains at least 20%, 25%, 30%, 35%, 40%, 45%, or 50% of the particular DP galacto-oligosaccharides by weight. Other exemplary levels of enrichment can include GOS that contains at least 20%, 25%, 30%, 35%, 40%, 45%, or 50% of the particular galacto-oligosaccharides of a particular DP or higher by weight. In some cases, the enriched GOS compositions have less than 10% or less than 5% of sugar monomers (e.g., galactose) and optionally less than 10% or less than 5% of dimeric galacto-oligosaccharides. In some embodiments, the enriched compositions of the invention also have less than 10% or less than 5% of trimeric (DP3) galacto-oligosaccharides. In some cases, the GOS compositions contain a mixed population of galacto-oligosaccharides, for example a composition containing a mix of galacto-oligosaccharides of DP 3, 4, 5, 6, 7, 8, 9, or 10, or other combinations thereof. Methods of purifying or preparing GOS compositions are known in the art (see, e.g., U.S. Pat. No. 8,425,930).

VI. Formulations

In general, any food or beverage that can be consumed by human infants or adults or animals may be used to make formulations containing the probiotic compositions described herein (e.g., compositions containing a bacteria expressing a GH-29 alpha-fucosidase, a GH-95 alpha-fucosidase, or expressing multiple alpha-fucosidases such as GH-29 and GH-95 fucosidases). Preferable foods include those with a semi-liquid consistency to allow easy and uniform dispersal of the prebiotic or probiotic compositions described herein. Accordingly, such food items include, without limitation, dairy-based products such as cheese, cottage cheese, yogurt, and ice cream. Fruits and vegetables targeted for infants/toddlers, such as apple sauce or strained peas and carrots (e.g., those from Gerber Products Company; Fremont, Mich.) are also suitable for use in the present invention. Both infant cereals such as rice- or oat-based cereals (e.g., Gerber) and adult cereals such as Musilix may also be suitable for use in this invention. In addition to foods targeted for human consumption, animal feeds may also be supplemented with the prebiotic and probiotic compositions of the invention.

Alternatively, the prebiotic and probiotic compositions of the invention may be used to supplement a beverage. Examples of such beverages include, without limitation, infant formula, follow-on formula, toddler's beverage, milk, fermented milk, fruit juice, fruit-based drinks, and sports drinks Many infant and toddler formulas are known in the art and are commercially available, including, for example, Carnation Good Start (Nestle Nutrition Division; Glendale, Calif.) and Nutrish A/B produced by Mayfield Dairy Farms (Athens, Term.). Other examples of infant or baby formula include those disclosed in U.S. Pat. No. 5,902,617. Other beneficial formulations of the compositions of the present invention include the supplementation of animal milks, such as cow's milk, which are normally lacking in HMOs.

Alternatively, the prebiotic and probiotic compositions of the present invention can be formulated into pills or tablets or encapsulated in capsules, such as gelatin capsules. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge or candy forms can comprise the compositions in a flavor, e.g., sucrose, as well as pastilles comprising the compositions in an inert base, such as gelatin and glycerin or sucrose and acacia emulsions, gels, and the like containing, in addition to the active ingredient, carriers known in the art. The inventive prebiotic or probiotic formulations can also contain conventional food supplement fillers and extenders such as, for example, rice flour.

In some embodiments, the prebiotic or probiotic composition can further comprise a non-human protein, non-human lipid, non-human carbohydrate, or other non-human component. For example, in some embodiments, the compositions of the invention comprise a bovine (or other non-human) milk protein, a soy protein, betalactoglobulin, whey, soybean oil or starch.

Alternatively, the prebiotic and probiotic compositions of the present invention can be administered to the subject in a manner that administers the composition to the gut, but bypass the oral cavity (e.g., the mouth or esophagus) or the stomach. For example, the compositions can be administered rectally, directly to the colon, or directly to the small intestine. In some cases, the method may include techniques to deliver the composition to the colon without delivering the composition to the small intestine.

The dosages of the prebiotic and probiotic compositions of the present invention can be varied depending upon the requirements of the individual and will take into account factors such as age (infant versus adult), weight, and reasons for the need for administration of or selection for beneficial gut bacteria (e.g., antibiotic therapy, chemotherapy, disease, or age). The amount administered to an individual, in the context of the present invention should be sufficient to establish colonization of the gut with beneficial bacteria over time. The size of the dose also will be determined by the existence, nature, and extent of any adverse side-effects that may accompany the administration of a prebiotic or probiotic composition of the present invention. The dosage range, effective as a food supplement and for reestablishing beneficial bacteria in the intestinal tract, ranges from about 1 micrograms/L to about 25 grams/L. A further advantageous range is about 100 micrograms/L to about 15 grams/L. Another useful range is 1 gram/L to 10 grams/L. In one embodiment, a concentration of 8 grams/L is preferred. (See, e.g., Knol et al., *J. Pediatric Gastro. and Nutr.* (2005) 40:36-42.) When used, Bifidobacteria may be included in the formulations of the invention in an amount of $10^6$ to $10^{12}$ colony forming units (CFU). A further advantageous range is $10^8$ to $10^{12}$ CFU. In one advantageous embodiment, $10^{10}$ CFU of Bifidobacteria may be included in the formulations of the invention.

It will be appreciated that it may be advantageous for some applications to include other pre-biotic factors in the formulations of the present invention. Such additional components may include, but are not limited to, fructooligosaccharides such as Raftilose (Rhone-Poulenc, Cranbury, N.J.), inulin (Imperial Holly Corp., Sugar Land, Tex.), and Nutraflora (Golden Technologies, Westminister, Colo.), as well as xylooligosaccharides, galactooligosaccharides, soyoligosaccharides, lactulose/lactitol, among others.

The present invention includes methods of making any of the above-described compositions. For example, the invention provides for methods of combining at least one or more oligosaccharides described herein with a non-human protein, non-human lipid, non-human carbohydrate, or other non-human component to produce a synthetic prebiotic or probiotic food. For example, in some embodiments, 1, 2, 3, 4, 5, 6, 7, 8, 9, 10 or more of the oligosaccharides described herein are combined with a non-human protein, non-human lipid, non-human carbohydrate, or other non-human component. In some embodiments, at least one or more oligosaccharide of the present invention are combined with a bovine (or other non-human) milk protein, a soy protein, beta-lactoglobulin, whey, soybean oil or starch.

VII. Examples

Introduction

Human milk contains a high concentration of complex oligosaccharides that influence the composition of the intestinal microbiota in breast-fed infants. Select species such as *Bifidobacterium longum* subsp. *infantis* and *B. bifidum* can utilize human milk oligosaccharides (HMO) in vitro as the sole carbon source, while *B. longum* subsp. *longum* and *B. breve* are less adapted to these substrates. We sought to examine the adaptations of a more representative number of *B. breve* strains to human milk oligosaccharides. For this purpose, a number of *B. breve* isolates from breast-fed infant feces were characterized for the presence of different glycosyl hydrolases that participate in HMO utilization, as well as by their ability to grow on HMO or specific HMO species such as lacto-N-tetraose (LNT) and fucosyllactose. All *B. breve* strains showed a vigorous growth on lacto-N-tetraose and lacto-N-neotetraose (LNnT), and in general growth on total HMO was moderate for most of the strains, with several strain differences. Growth and consumption of fucosylated HMO was strain-dependent, primarily in isolates possessing a Glycosyl Hydrolase family 29 α-fucosidase. Glycoprofiling of the spent supernatant after HMO fermentation by select strains revealed that all *B. breve* can utilize sialylated HMO to a certain extent, especially sialyl-lacto-N-tetraose. Interestingly, this oligosaccharide was depleted before neutral lacto-N-tetraose by strain SC95. The present results indicate that the HMO consumption phenotype in *B. breve* is variable. Specific strains, however, display adaptations to substrates including fucosylated and sialylated HMO. The present results provide a rationale for the predominance of this species in breast-fed infant feces, and a more accurate picture of the ecology of the developing infant intestinal microbiota.

Example 1: Isolation and Identification of *Bifidobacterium* from Breast-Fed Infant Feces Materials and Methods Subjects.

Fecal samples were collected from 40 exclusively breast-fed term infants at 3 and 4 months of age. None of the infants enrolled in this study had received antibiotic treatment, infant-formula or solid food. Parents transferred their infant fecal samples into sterile plastic tubes and were instructed to immediately store the samples in −20° C. until transported by study personnel. Fecal samples were transported on dry ice and stored at −80° C. before processing.

Microbial Isolations.

For isolation of *Bifidobacterium*, 100 mg of each fecal sample was taken aseptically, transferred to a sterile tube, diluted tenfold with 1% peptone water (Becton Dickinson, Sparks, Md.), and homogenized by vortexing. Ten-fold dilutions were prepared with 1% peptone water and inoculated on modified BSM agar (mBSM). Modified BSM agar was prepared by supplementing de Man Rogosa Sharpe (MRS) media (Becton Dickinson, Sparks, Md.) with 15 g/L agar, 500 mg/L L-cysteine-HCl, 100 mg/L mupirocin, 25 mg/L kanamycin, 4.28 mg/L polymixin B, 25 mg/L iodoacetate, 20 mg/L nalidixic acid and 25 mg/mL of 2,3,5-triphenyltetrazoliumclhoride (Sigma). The plates were incubated for 48 h at 37° C. in an anaerobic chamber (Coy Laboratory Products, Grass Lake, Mich.), in an atmosphere containing 5% carbon dioxide, 5% hydrogen, and 90% nitrogen. Resulting colonies were streaked onto mBSM agar, and after two passages they were grown in MRS broth supplemented with 0.05% L-cysteine-HCl and stored at −80° C. in 25% glycerol. Prior to each assay all bacteria strains were subcultured twice in MRS broth supplemented with 0.05% L-cysteine-HCl and incubated at 37° C. for 18 h in an anaerobic chamber.

Additional *B. breve* strains were obtained from the Japanese Collection of Microorganism (RIKEN BioResource Center, Japan), the American Type Culture Collection (Manassas, Va.), and the University of California-Davis Viticulture and Enology Culture Collection (Table 1).

TABLE 1

List of *Bifidobacterium* strains used in this study.

| Code | Species | Additional strain information[a] | Source |
|---|---|---|---|
| UCC2003 | B. breve | O'Connell et al., 2011 | Infant nursing stool |
| ATCC15700 | B. breve | JCM1192; DSM20213 | Infant feces |
| ATCC15698 | B. breve | JCM1273; DSM20091 | Infant feces |
| ATCC15701 | B. breve | JCM7016 | Infant feces |
| JCM7017 | B. breve | | Human feces |
| JCM7019 | B. breve | | Infant feces |
| JCM7020 | B. breve | | Infant feces |
| S-17c | B. breve | Roy et al. 1996 | Infant feces |
| S-46 | B. breve | Roy et al. 1996 | Infant feces |
| SC81 | B. breve | This study | Infant feces |
| SC95 | B. breve | This study | Infant feces |
| SC139 | B. breve | This study | Infant feces |
| SC154 | B. breve | This study | Infant feces |
| SC500 | B. breve | This study | Infant feces |
| SC506 | B. breve | This study | Infant feces |
| SC508 | B. breve | This study | Infant feces |
| SC522 | B. breve | This study | Infant feces |
| SC559 | B. breve | This study | Infant feces |
| SC567 | B. breve | This study | Infant feces |
| SC568 | B. breve | This study | Infant feces |
| SC573 | B. breve | This study | Infant feces |
| SC580 | B. breve | This study | Infant feces |
| SC670 | B. breve | This study | Infant feces |
| KA179 | B. breve | This study | Infant feces |
| ATCC15697 | B. longum subsp. infantis | JCM1222; DSM20088 | Infant feces |
| JCM 10602 | B. animalis subsp. lactis | DSMZ 10140 | Dairy product |

[a]The original strain numbers are also noted, if known. JCM, Japan Collection of Microorganisms, ATCC, American Type Culture Collection; DSMZ, German Collection of Microorganisms and Cell Culture.

Identification of Bifidobacteria by 16S rDNA Sequencing.

Genomic DNA was obtained from 1 ml of each culture, and centrifuged for 5 min at 2000×g. The bacterial pellet was resuspended and incubated for 30 min at 37° C. with enzymatic lysis buffer 20 mM Tris-Cl pH 8.0, 2 mM sodium EDTA, 1.2% Triton X-100, and 40 mg/ml lysozyme (Sigma, Mo.). After enzymatic lysis, bacterial DNA was isolated from the samples using the DNeasy tissue kit (Qiagen, Valencia, Calif.) according to the manufacturer instructions. DNA quality and yield was checked using a Nanodrop spectrophotometer (Wilmington, Del.); the DNA was then stored at −20° C. until further use. To identify the isolates at species level, the 16S rDNA gene was amplified by PCR using the universal primers 27F 5'-AGAGTTTGATCCTG-GCTCAG (SEQ ID NO:13) and 1492R 5'-TACGGTTAC-CTTGTTACGA (SEQ ID NO:14) on an Applied Biosystems 2720m Thermal Cycler (Applied Biosystems, Mountain View, Calif.). One μl of extracted DNA was added to 50 μl reaction mixture containing 50 pmol of primers, 500 mM of each dNTP, 0.1 vol of 10× PCR buffer, 2.5 mM MgCl2, and 1 U AmpliTaq gold polymerase (Applied Biosystems). Amplification mixtures were subjected to 4 min of denaturation at 94° C., 30 cycles of 94° C. for 30 s, 55° C. for 40 s, and 72° C. for 1 min 30 s, followed by a final extension period of 7 min at 72° C. The resulting amplicons were separated on a 1% agarose gel, followed by GelRed staining (Phenix Research Products, Candler, N.C.), and purification using a QIAquick PCR Purification Kit (Qiagen, Valencia, Calif.). Sequencing was performed on an ABI 3730 Capillary Electrophoresis Genetic Analyzer using BigDye Terminator chemistries at the University of California Davis DNA Sequencing Facility. The sequences were analyzed using BioEdit 7.0 (available at the website at mbio.ncsu.edu/BioEdit/BioEdit.html), and checked by nucleotide-nucleotide BLAST comparison at the NCBI database for species identification.

Multilocus Sequence Typing (MLST) of Strains.

MLST analysis of *B. breve* isolates targeted intragenic regions of seven housekeeping genes clpC, purF, gyrB, fusA, Iles, rplB, rpoB. The PCR reaction was prepared as above and cycling conditions were optimized for every primer set (Table 2). The reaction included an initial denaturation at 95° C. for 4 min, followed by 35 cycles of 95° C. for 30 s, annealing at 60-67° C. for 30 s, elongation at 72° C. for 60 s, final extension at 72° C. for 7 min, and holding at 4° C. The PCR products were separated and sequenced as above.

TABLE 2

MLST genes and primers.

| PCR primer (5'-3') (SEQ ID NO:)*,a | Expected Amplicon size (bp) | Anneling Temp. (° C.) |
|---|---|---|
| GAG TAC CGC AAG TAC ATC GAG (15)<br>CAT CCT CAT CGT CGA ACA GGA AC (16) | 748 | 63 |
| CAT TCG AAC TCC GAC ACC GA (17)<br>GTG GGG TAG TCG CCG TTG (18) | 977 | 62 |
| AGC TGC ACG CBG GCG GCA AGT TCG (19)<br>GTT GCC GAG CTT GGT CTT GGT CTG (20) | 811 | 66 |
| ATC GGC ATC ATG GCY CAC ATY GAT (21)<br>CCA GCA TCG GCT GMA CRC CCT T (22) | 784 | 66 |
| ATC CCG CGY TAC CAG ACS ATG (23)<br>CGG TGT CGA CGT AGT CGG CG (24) | 789 | 66 |
| GGA CAA GGA CGG CRT SCC SGC CAA (25)<br>ACG ACC RCC GTG CGG GTG RTC GAC (26) | 498 | 67 |
| GGC GAG CTG ATC CAG AAC CA (27)<br>GCA TCC TCG TAG TTG TAS CC (28) | 1057 | 62 |

*Upper sequence, forward primer; Lower sequence, reverse primer.
aIn the primer sequence R indicates (A/G), S (C/G), Y (C/T), B(G/T/C), M(A/C).

Sequencing data for all loci was edited using BioEdit 7.0 and aligned using CLUSTAL W. Phylogenetic analysis and concatenations of the sequenced loci were performed using the Molecular Evolutionary Genetic Analysis (MEGA) software version 5 (megasoftware.net). Descriptive evolutionary analysis including mol % G+C content, number of polymorphic sites, nucleotide diversity it/site, average number of nucleotide differences k were calculated using DnaSP version 5.10 (Table 3). Allelic sequences were assigned (see Cai et al. (2007) *Microbiol.* 153:2655) (Table 4). A minimum evolution tree of the concatenated loci was calculated using MEGA 5.0 (FIG. 1).

TABLE 3

Descriptive evolutionary analysis of MLST data.

| Gene | Fragment analyzed (bp)* | G + C (mol %) | polymorphic sites | Allele frequencies | π | k |
|---|---|---|---|---|---|---|
| clpC | 678 (0.25) | 61.97 | 14 | 8 | 0.00404 | 2.739 |
| purF | 855 (0.56) | 62.33 | 65 | 11 | 0.01308 | 11.18116 |
| gyrB | 688 (0.33) | 60.17 | 14 | 12 | 0.00335 | 2.30435 |
| fusA | 753 (0.35) | 60.35 | 14 | 8 | 0.00319 | 2.4058 |
| Iles | 743 (0.22) | 61.51 | 41 | 12 | 0.0148 | 10.78986 |
| rplB | 428 (0.51) | 64.75 | 8 | 5 | 0.00273 | 1.16667 |
| rpoB | 965 (0.27) | 62.89 | 16 | 11 | 0.00353 | 3.4058 |

*Percentage of the gene is given in parenthesis.
π = mean pairwise nucleotide difference per site.
k = mean pairwise nucleotide difference per sequence.

TABLE 4

Allelic profiles of 24 *B. breve* strains analyzed by MLST.

| Strains | STa | clpC | purF | gyrB | fusA | Iles | rplB | rpoB |
|---|---|---|---|---|---|---|---|---|
| UCC2003 | 1 | 1 | 1 | 1 | 1 | 1 | 1 | 1 |
| ATCC15700 | 2 | 1 | 2 | 2 | 1 | 2 | 2 | 2 |
| ATCC15698 | 3 | 1 | 3 | 3 | 1 | 3 | 3 | 3 |
| ATCC15701 | 4 | 2 | 4 | 4 | 1 | 4 | 3 | 4 |
| JCM7017 | 4 | 2 | 4 | 4 | 1 | 4 | 3 | 4 |
| JCM7019 | 5 | 3 | 5 | 5 | 7 | 5 | 3 | 5 |
| JCM7020 | 6 | 4 | 6 | 5 | 8 | 6 | 3 | 6 |
| S-17c | 7 | 1 | 7 | 6 | 1 | 4 | 3 | 2 |
| S-46 | 8 | 2 | 4 | 4 | 1 | 4 | 3 | 7 |
| SC81 | 9 | 5 | 8 | 7 | 2 | 7 | 3 | 8 |
| SC95 | 10 | 6 | 9 | 8 | 1 | 3 | 3 | 3 |
| SC139 | 11 | 7 | 3 | 8 | 1 | 8 | 3 | 4 |
| SC154 | 12 | 2 | 1 | 8 | 1 | 3 | 3 | 1 |
| SC500 | 13 | 1 | 10 | 3 | 2 | 3 | 4 | 9 |
| SC506 | 14 | 6 | 9 | 8 | 3 | 3 | 1 | 3 |
| SC508 | 15 | 1 | 1 | 9 | 1 | 9 | 5 | 2 |
| SC522 | 9 | 5 | 8 | 7 | 2 | 7 | 3 | 8 |
| SC559 | 16 | 1 | 1 | 10 | 1 | 10 | 3 | 10 |
| SC567 | 17 | 1 | 11 | 8 | 6 | 11 | 3 | 1 |

TABLE 4-continued

Allelic profiles of 24 B. breve strains analyzed by MLST.

| Strains | ST[a] | Allele | | | | | | |
|---|---|---|---|---|---|---|---|---|
| | | clpC | purF | gyrB | fusA | Iles | rplB | rpoB |
| SC568 | 10 | 6 | 9 | 8 | 1 | 3 | 3 | 3 |
| SC573 | 18 | 2 | 4 | 11 | 1 | 3 | 3 | 3 |
| SC580 | 9 | 5 | 8 | 7 | 2 | 7 | 3 | 8 |
| SC670 | 19 | 1 | 1 | 12 | 5 | 11 | 3 | 11 |
| KA179 | 20 | 8 | 3 | 8 | 4 | 12 | 3 | 9 |

[a]ST Indicates specific sequence type.

Results

Around 500 isolates were identified by 16S rDNA sequencing, and a total of 461 isolates were identified as *Bifidobacterium*. Seven species of bifidobacteria were detected, and the species *longum*, which includes subspecies *longum* and *infantis*, was found to be more represented, followed by *B. breve* with 77 strains (Table 5).

TABLE 5

Distribution of isolates of bifidobacteria from breast-fed infants identified by 16S DNA.

| Species | Number of isolates identified |
|---|---|
| B. longum/B. infantis | 297 |
| B. breve | 77 |
| B. pseudocatenulatum | 45 |
| B. bifidum | 22 |
| B. dentium | 8 |
| B. adolescentis | 7 |
| B. animalis | 5 |

We further investigated the identity of the *B. breve* isolates at the strain level by MLST (Deletoile et al. (2010) *Res Microbiol.* 161:82). The analysis also included nine strains from culture collections (Table 1). A total of 172 single nucleotide polymorphisms (SNPs) were found in seven loci, and they generated between 8 rplB and 65 purF polymorphic sites (Table 3). Twenty different allelic profiles were identified in the 86 *B. breve* isolates analyzed (Table 4). Some strains isolated from the unrelated infants in the study shared similar profiles, and we conservatively considered them as different strains. This resulted in a library of 24 strains of *B. breve* (Table 1), for which a consensus phylogenetic tree of the concatenated MLST data is shown in FIG. 1.

Example 2: Characterization of Glycosyl Hydrolases from Isolated Strains

Materials and Methods

In order to study the potential adaptations of the *B. breve* isolates for growth on HMO, we first determined the presence of three key GH classes required to cleave HMO into its constituent monosaccharides. β-galactosidase activity was not observed because it is widespread in the *Bifidobacterium* genus. α-fucosidases (Blon_2336, Blon_2335, Blon_0248/0426, Blon_0346), α-sialidases (Blon_2348, Blon_0646), and β-hexosaminidase Blon_0459 protein sequences identified in the genome of *B infantis* ATCC 15697 were aligned with homolgous sequences from the GeneBank database (Accession numbers showed in Table 6) using Bioedit 7.0 and degenerated primers were designed to amplify conserved regions (Table 7). To differentiate between Blon_0248 and Blon_0426, strains positive for fucosidase Blon_0248/0426 were also amplified with the primers designed to amplify the complete gene in *B. infantis* ATCC 15697 (Table 7). PCR reactions were prepared as above with 200 pmol of primers. Cycling conditions were optimized for every primer set (Table 7), and consisted of an initial denaturation at 95° C. for 4 min, followed by 35 cycles of 95° C. for 30 s, annealing at 45-55° C. for 30 s, elongation at 72° C. for 60 s, final extension at 72° C. for 7 min; and holding at 4° C. The resulting amplicons were separated and sequenced as above. *B. infantis* ATCC 15697 and *B. animalis* JCM 10602 were used as positive and negative control strains, respectively.

TABLE 6

Genebank accession numbers for glycosyl hydrolase.

| Glycosyl hydrolase name | Protein sequences accession numbers |
|---|---|
| Blon_2335 | YP_002323771.1; ZP_06596922.1; ZP_03742645.1; ZP_03167824.1; NP_241708.1; ZP_03474775.1; YP_003010680.1; ZP_04552485.1; ZP_07812017.1 |
| Blon_2336 | YP_002323772.1; WP_003795385.1; WP_007588699.1; YP_001297867.1; WP_006775425.1; YP_003822597.1; WP_008706707.1; WP_009776262.1 |
| Blon_0248/0426 | YP_002321754.1; ZP_08285605.1; ZP_08026776.1; ZP_06607921.1; ZP_06184004.1; YP_002533924.1; ZP_05989289.1; ZP_02477566.1; YP_001851141.1; ZP_03212758.1; ZP_05280631.1 |
| Blon_0346 | YP_002321848.1; ZP_02040503.1; ZP_02079496.1; ZP_08131039.1; ZP_05718978.1; YP_004456548.1; P_003242853.1;YP_002547035.1 |
| Blon_2348 | YP_002323784.1; WP_003818390.1; ACH92844.1; WP_003796112.1; ACH92824.1; BAD66680.2 |
| Blon_0646 | YP_002322131.1; YP_007554019.1 |
| Blon_0459 | YP_002321953.1., YP_007555353.1 |

TABLE 7

Glycosyl hydrolase gene and qPCR primers.

| Primer name | Primer sequence (5'-3') (SEQ ID NO:)[a] | amplicon size (bp) | Anneling Temp. (° C.) |
|---|---|---|---|
| Blon_2335F | GARATGAAYTAYTGGATG (29) | 960 | 56° C. |
| Blon_2335R | TTNCCRTCDATYTGRAANGGNGG (30) | | |
| Blon_2336F | AARCAYCAYGAYGGNTTYTG (31) | 600 | 55° C. |
| Blon_2336R | ACYTCNGCNGGRTACCA (32) | | |

TABLE 7-continued

Glycosyl hydrolase gene and qPCR primers.

| Primer name | Primer sequence (5'-3') (SEQ ID NO:)[a] | amplicon size (bp) | Anneling Temp. (° C.) |
|---|---|---|---|
| Blon_0248/ 0426F | TAYGCNGARTGGTAY (33) | 210 | 45° C. |
| Blon_0248/ 0426R | TCRTGRTGYTTNGTNGT (34) | | |
| Blon_0346F | YTNGAYTTYCAYACNWS (35) | 740 | 48° C. |
| Blon_0346R | TCRTGRTGYTTNGTNGT (36) | | |
| Blon_2348F | ATHACNGCNGAYATHAC (37) | 250 | 45° C. |
| Blon_2348R | TCNACNACYTTRTTYTCRTC (38) | | |
| Blon_0646F | CCACCAGACATGGAACAGTG (39) | 220 | 60° C. |
| Blon_0646R | AAATCGCCGAAGGTGATATG (40) | | |
| Blon_0459F | CCCCACCCTCGACTGGCTCA (41) | 510 | 62° C. |
| Blon_459R | CTTCGAGGTGGCACAGG (42) | | |
| 0248WF | ACCAACAACCAGCAACCAAT (43) | 135 | 56° C. |
| 0248WR | ATCGAATACGGCACCTTCAG (44) | | |
| 0426WF | ACCAACAACCAGCAACCAAT (45) | 135 | 56° C. |
| 0426WR | GACCGCCTTCATGGATAAGA (46) | | |
| RNP-F | AACCTGATGATCGGACGACG (47) | 182 | 60° C. |
| RNP-R | GGCAAACTGCTCATCCAACG (48) | | 60° C. |
| GH29-F | GGACTGAAGTTCGGCGTGTA (49) | 160 | 60° C. |
| GH29-R | TCGTTGTCCTCCTCCGAGAT (50) | | 60° C. |
| GH95-F | CGCGGACTACCGCAGATATT (51) | 163 | 60° C. |
| GH95-R | ATCGAACATTGCCTCTGCCA (52) | | 60° C. |

[a]In the primer sequence R indicates (A/G), W (A/T), S (C/G), Y (C/T), H (A/C/T), D (A/G/T), N (A/C/G/T).

Results

Figure 2:
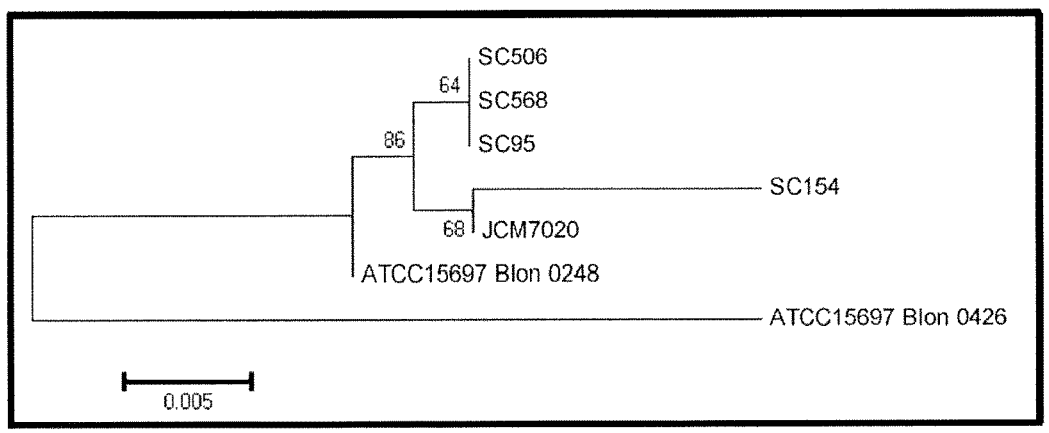
FIG. 2. Phylogenetic relationship of homologous fucosidase Blon_0248 in *B. breve* strains. The tree is drawn to scale, with branch lengths in the same units (number of amino acid substitutions per site) as those of the evolutionary distances used to infer the phylogenetic tree The evolutionary history was inferred using the Minimum Evolution method, followed by 1000 bootstrap replicates.

The genome of *B. breve* UCC2003 (O'Connell et al. (2011) *PNAS* 108:11217) contains an α-fucosidase, an α-sialidase and a β-hexosaminidase with significant homology to cognate enzymes in *B. infantis* ATCC 15697. No homology was found to the same glycosyl hydrolases in *B. bifidum* genomes. Based on this, we used degenerate primers to look for genes encoding these GH in the assembled *B. breve* strains (Table 8). All of the *B. breve* strains possessed a gene homologous to β-hexosaminidase Blon_0459 in *B. infantis* (Gamido et al. (2012) *Mol Cell Proteomics* 11:775), an α-fucosidase similar to Blon_2335 in *B. infantis* ATCC 15697 (Sela et al. (2012) *Appl. Env. Microbiol.* 78:795) and all strains excepting JCM 7020 possessed an α-sialidase, related to Blon_0646 in *B. infantis* (Sela et al. (2011) *J. Biol. Chem.* 286:11909). Moreover, five strains possessed a second α-fucosidase, homolog to locus tag Blon_0248 in *B. infantis* ATCC 15697 (Sela et al. (2012) *Appl. Env. Microbiol.* 78:795) that belongs to GH family 29 (Table 8 and FIG. 2).

TABLE 8

Presence of glycosyl hydrolases and growth in different HMO by *B. breve* strains

| | Glycosyl hydrolases[a] | | | | Bacterial growth | | | | | | |
|---|---|---|---|---|---|---|---|---|---|---|---|
| | α-fucosidase | | α-sialidase | β-hexosaminidase | | | | | | | |
| Strain | GH95 | GH29 | GH33 | GH20 | HMO[b] | LNT | LNnT | 2FL | 3FL | 3SL | 6SL |
| UCC2003 | + | − | + | + | + | +++ | +++ | − | + | − | − |
| ATCC15700 | + | − | + | + | + | +++ | +++ | − | − | − | − |
| ATCC15698 | + | − | + | + | ++ | +++ | +++ | − | − | − | − |
| ATCC15701 | + | − | + | + | +++ | +++ | +++ | − | − | − | − |
| JCM7017 | + | − | + | + | ++ | +++ | +++ | − | − | − | − |
| JCM7019 | + | − | + | + | ++ | +++ | +++ | + | + | − | − |

TABLE 8-continued

Presence of glycosyl hydrolases and growth in different HMO by B. breve strains

| | Glycosyl hydrolases[a] | | | Bacterial growth | | | | | | |
|---|---|---|---|---|---|---|---|---|---|---|
| | α-fucosidase | α-sialidase | β-hexosaminidase | | | | | | | |
| Strain | GH95 | GH29 | GH33 | GH20 | HMO[b] | LNT | LNnT | 2FL | 3FL | 3SL | 6SL |
| JCM7020 | + | + | − | + | ++ | +++ | +++ | − | − | − | − |
| S-17c | + | − | + | + | + | +++ | +++ | − | + | − | − |
| S-46 | + | − | + | + | ++ | +++ | +++ | − | + | − | − |
| SC81 | + | − | + | + | ++ | +++ | +++ | − | − | − | − |
| SC95 | + | + | + | + | +++ | +++ | +++ | +++ | + | − | − |
| SC139 | + | − | + | + | ++ | +++ | +++ | − | − | − | − |
| SC154 | + | + | + | + | +++ | +++ | +++ | − | − | − | − |
| SC500 | + | − | + | + | ++ | +++ | +++ | − | − | − | − |
| SC506 | + | + | + | + | ++ | +++ | +++ | − | − | − | − |
| SC508 | + | − | + | + | + | +++ | +++ | − | − | − | − |
| SC522 | + | − | + | + | ++ | +++ | +++ | − | + | − | − |
| SC559 | + | − | + | + | ++ | +++ | +++ | − | − | − | − |
| SC567 | + | − | + | + | ++ | +++ | +++ | − | − | − | − |
| SC568 | + | + | + | + | ++ | +++ | +++ | +++ | + | − | − |
| SC573 | + | − | + | + | + | +++ | +++ | − | + | − | − |
| SC580 | + | − | + | + | ++ | +++ | +++ | − | + | − | − |
| SC670 | + | − | + | + | + | +++ | +++ | − | − | − | − |
| KA179 | + | − | + | + | ++ | +++ | +++ | + | − | + | + |
| ATCC15697 | + | + | + | + | +++ | +++ | +++ | +++ | +++ | +++ | +++ |
| JCM10602 | − | − | − | − | − | − | − | − | − | − | − |

[a]Positive amplification + indicates that the sequence of the PCR product is >55% homologous at the aminoacid level to the respective GH gene in B. infantis ATCC15697.
[b]Level of growth was classified as Negative −: OD <0.200; Low +: OD 0.200-0.550; Moderate ++: OD 0.550-0.750; High +++: OD >0.750

Example 3: Characterization of the Growth of Isolated Strains on Human Milk Oligosaccharides Materials and Methods The 24 B. breve strains in Table 1 were tested for growth in the presence of seven different substrates: HMO (Ward et al. (2006) Appl. Env. Microbiol. 72:4497), LNT, lacto-N-neotetraose (LNnT), 2'-fucosyllactose (2FL), 3'-fucosyllactose (3FL) (Glycom, Denmark), 3'-sialyllactose (3SL), and 6'-sialyllactose (6SL) (GenChem. Inc. Korean). B. infantis ATCC 15697, and B. animalis JCM 10602 were included as positive and negative control for growth in HMO, respectively. Two µl of each resulting overnight culture was used to inoculate 200 µl of modified MRS (mMRS) medium supplemented with 2% (w/v) of each sterile-filtered substrate as the sole carbohydrate source, and another 2 µl inoculated into mMRS without added sugar. The media was supplemented with 0.05% (w/v) L-cysteine, and in all the cases the cultures in the wells of the microliter plates were covered with 30 µl of sterile mineral oil to avoid evaporation. The incubations were carried out at 37° C. in an anaerobic chamber (Coy Laboratory Products, Grass Lake, Mich.). Cell growth was monitored in real time by assessing optical density (OD) at 600 nm using a BioTek PowerWave 340 plate reader (BioTek, Winoosky, Vt.) every 30 min preceded by 15 seconds shaking at variable speed. Two biological replicates and three technical replicates each were performed for every studied strain. Maximum ODs and growth rates were calculated and expressed as the mean of all replicates with the respective standard deviation. These calculations were performed as described in Breidt et al. (1994) J. Rapid Meth. Autom. Microbiol. 3:59) The OD obtained for each strain grown on the different substrates, was compared with the OD obtained in the absence of sugar source. This difference in OD (ΔOD) was used as a parameter to evaluate the strain's ability for growing on the different substrates.

Results

Growth behavior on HMO and maximum OD values obtained were parameters to classify this panel in three groups (Table 8).

Figure 3:
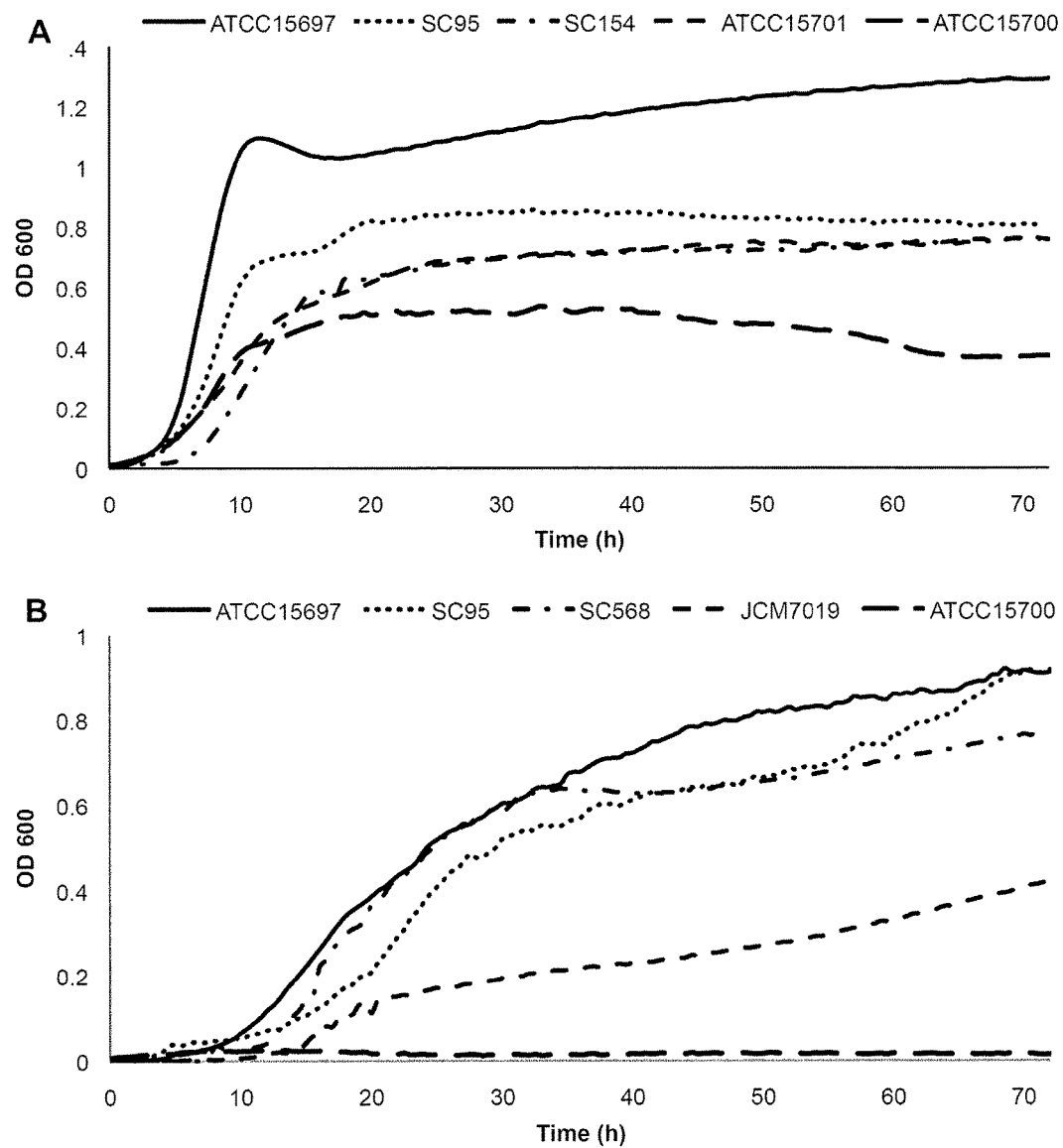
FIG. 3. Growth of *B. breve* on HMO. *B. breve* isolates were inoculated on semi-synthetic MRS medium supplemented with 2% w/v HMO (A) and 2FL (B). *B. infantis* ATCC 15697 and *B. breve* ATCC 15700 were included as high and low growth controls respectively. Fermentations were carried out in triplicate.

In general, a moderate growth on HMO was witnessed for all the strains (Table 8 and Table 9), with some strain level differences (Table 8). Interestingly, three strains (SC95, SC154 and ATCC 15701) exhibited remarkable growth on HMO compared to the type strain B. breve ATCC 15700, but still lower overall growth and growth rate relative to B. infantis ATCC 15697 (FIG. 3A and Table 9).

TABLE 9

Kinetic analysis of bacterial growth in 2% HMO.

| | Kinetic parameters in 2% HMO | | | | | | | |
|---|---|---|---|---|---|---|---|---|
| Strain | Growth rate (1/h) | SD | Lag time (h) | SD | Generation time (h) | SD | Max. OD (600 nm) | SD |
| UCC2003 | 6.70E−02 | ±7.55E−03 | 3.070 | ±0.132 | 4.531 | ±0.543 | 0.524 | ±0.055 |
| ATCC15700 | 6.16E−02 | ±1.12E−02 | 5.420 | ±0.042 | 5.007 | ±1.001 | 0.538 | ±0.025 |
| ATCC15698 | 7.98E−02 | ±2.14E−03 | 4.260 | ±0.118 | 3.772 | ±0.102 | 0.656 | ±0.065 |
| ATCC15701 | 5.77E−02 | ±2.22E−03 | 2.445 | ±0.881 | 5.225 | ±0.206 | 0.779 | ±0.040 |
| JCM7017 | 7.19E−02 | ±4.50E−03 | 5.549 | ±0.096 | 4.199 | ±0.257 | 0.656 | ±0.021 |

TABLE 9-continued

Kinetic analysis of bacterial growth in 2% HMO.

Kinetic parameters in 2% HMO

| Strain | Growth rate (1/h) | SD | Lag time (h) | SD | Generation time (h) | SD | Max. OD (600 nm) | SD |
|---|---|---|---|---|---|---|---|---|
| JCM7019 | 9.94E−02 | ±4.55E−03 | 7.653 | ±0.310 | 3.033 | ±0.135 | 0.655 | ±0.014 |
| JCM7020 | 8.51E−02 | ±2.08E−03 | 4.016 | ±0.083 | 3.538 | ±0.087 | 0.661 | ±0.015 |
| S-17c | 7.26E−02 | ±7.21E−03 | 6.161 | ±0.237 | 4.170 | ±0.398 | 0.540 | ±0.013 |
| S-46 | 8.36E−02 | ±9.27E−03 | 4.413 | ±0.073 | 3.627 | ±0.378 | 0.71 | ±0.033 |
| SC81 | 1.07E−01 | ±4.81E−03 | 6.331 | ±0.108 | 2.825 | ±0.129 | 0.715 | ±0.033 |
| SC95 | 1.20E−01 | ±6.43E−03 | 4.655 | ±0.047 | 2.523 | ±0.131 | 0.859 | ±0.029 |
| SC139 | 9.41E−02 | ±9.16E−03 | 5.390 | ±0.204 | 3.219 | ±0.297 | 0.667 | ±0.015 |
| SC154 | 7.54E−02 | ±5.22E−03 | 6.295 | ±0.166 | 4.007 | ±0.281 | 0.768 | ±0.031 |
| SC500 | 5.24E−02 | ±3.65E−03 | 13.512 | ±0.362 | 5.759 | ±0.404 | 0.558 | ±0.026 |
| SC506 | 5.92E−02 | ±2.66E−03 | 3.806 | ±0.050 | 5.088 | ±0.222 | 0.731 | ±0.0007 |
| SC508 | 4.26E−02 | ±2.37E−03 | 5.157 | ±0.070 | 7.086 | ±0.390 | 0.277 | ±0.054 |
| SC522 | 4.88E−02 | ±1.14E−02 | 1.050 | ±0.223 | 6.439 | ±1.715 | 0.698 | ±0.047 |
| SC559 | 6.26E−02 | ±1.27E−03 | 6.311 | ±0.137 | 4.807 | ±0.098 | 0.612 | ±0.0015 |
| SC567 | 5.76E−02 | ±5.49E−03 | 9.953 | ±0.765 | 5.256 | ±0.529 | 0.567 | ±0.042 |
| SC568 | 6.26E−02 | ±2.91E−03 | 6.216 | ±0.524 | 4.815 | ±0.220 | 0.680 | ±0.034 |
| SC573 | 3.31E−02 | ±3.45E−03 | 3.419 | ±0.123 | 9.168 | ±0.933 | 0.306 | ±0.014 |
| SC580 | 6.34E−02 | ±3.82E−03 | 2.045 | ±0.204 | 4.762 | ±0.284 | 0.727 | ±0.028 |
| SC670 | 3.38E−02 | ±5.98E−03 | 9.886 | ±0.234 | 9.083 | ±1.505 | 0.332 | ±0.054 |
| KA179 | 1.13E−01 | ±2.83E−03 | 6.990 | ±1.144 | 2.673 | ±0.066 | 0.606 | ±0.038 |
| ATCC15697 | 2.07E−01 | ±3.29E−03 | 3.930 | ±0.051 | 1.452 | ±0.022 | 1.295 | ±0.015 |
| JCM10602 | 1.10E−02 | ±1.45E−03 | 14.919 | ±2.389 | 27.578 | ±3.368 | 0.180 | ±0.025 |

All *B. breve* strains grew on LNT and LNnT to high cell densities and at levels comparable to *B. infantis* ATCC 15697 (Table 8). Interestingly, a few strains were able to grow on fucosylated HMO (FIG. 3B and Table 8). The isolates SC95 and SC568 grew well on 2FL, to a similar extent than *B. infantis* ATCC 15697. Using 3FL as the sole carbon source, only the strains SC95 and JCM 7019 showed growth (Table 8). Finally, growth on 3SL and 6SL was only observed for one strain (Table 8).

Example 4: Glycoprofiling and Gene Expression Analysis of Isolated Strains

Materials and Methods

Glycoprofiling.

Bacterial cultures in mMRS with 2% HMO were collected at the end of the exponential phase and centrifuged at 12000×g for 30 min. In the case of *B. breve* SC95, the samples were collected at three different points in the growth curve, approximately $OD_{600nm}$=0.2, 0.5 and 0.8. At least two biological replicates were performed in triplicate. Supernatants were filtered using a multiscreen 96-well filtration plate 0.22 µm (Millipore, Billerica, Mass.) prior to storage at −80° C. Remaining oligosaccharides were recovered from the supernatants (25 µl) and reduced to their alditol forms with 1M $NaBH_4$ at 65° C. for 1.5 h. Each replicate was desalted by solid-phase extraction on graphitized carbon cartridges. Salts were removed with 6 mL of deionized water and oligosaccharides were eluted with 20% acetonitrile in water (v/v) and with 40% acetonitrile in 0.01% trifluoroacetic acid (v/v). SPE fractions were combined and dried under vacuum. Samples were reconstituted in 100 µl of deionized water and diluted 50-fold for LC-MS analysis.

An Agilent high performance liquid chromatography chip time of flight (HPLC-Chip/TOF) mass spectrometer equipped with a capillary pump for sample loading and a nano pump for chromatographic separation was used for HMO analysis. Separation was performed on a microfluidic chip equipped with an enrichment and nano-LC analytical column, both packed with porous graphitized carbon. Briefly, HMO were separated by a 65 min gradient using a binary solvent system consisting of 3% acetonitrile/water in 0.1% formic acid (v/v) solvent A and 90% acetonitrile/water in 0.1% formic acid (v/v) solvent B. HMO were analyzed in positive ion mode, with a mass range between 300-2000 m/z. Agilent's Masshunter software version B.03.01 was used for data acquisition and data analysis.

HMO monosaccharide composition was determined using accurate mass within ±20 ppm mass error of theoretically calculated masses. Specific structures were assigned to HMO peaks by matching the reproducible retention time to that reported in annotated HMO libraries. Percent consumption was calculated using a label-free method, employing the un-inoculated HMO pool as an external standard. Total HMO consumption was calculated with respect to the un-inoculated control by normalizing the summed abundance of all identified oligosaccharide spectra in ion counts in the bacterial supernatant to that of the control using the following equation:

$$\left[1 - \left(\frac{\sum_{i=1}^{n} API \text{ bacteria sample}}{\sum_{i=1}^{n} API \text{ un-incoluated control}}\right)\right] \times 100$$

where API is absolute peak intensity and n is the number of identified HMO. The consumption of individual HMO species was quantitated in the same manner, in which the absolute peak intensity of a specific HMO structure was normalized to the peak intensity of the corresponding structure in the un-inoculated control.

Gene Expression Analysis.

The full nucleotide sequences of the genes encoding a GH95 and a GH29 α-fucosidase in the strain *B. breve* SC95 generated were used to design qPCR primers using the primer-BLAST tool at NCBI (Table 7). For relative quantification, the rnpA gene protein component of ribonuclease P complex was used. *B. breve* SC95 was grown as described above in mMRS supplemented with either 2% lactose, 2%

HMO or 2% 2FL in a microplate reader, and cultures were taken at mid-exponential phase OD 0.6-1.0. Samples were immediately pelleted at 12000×g for 1 min and stored in RNA later Ambion. RNA extraction, cDNA conversion and qPCR were performed (Gamido et al. (2012) *Anaerobe* 18:430).

Results

Based on their growth kinetic parameters and ability to utilize certain glycans, six strains of *B. breve* were selected to examine the consumption of 22 different oligosaccharides during growth on total HMO. This included strains SC95, SC154, SC568, SC580, ATCC15701, and JCM7019, as well as *B. infantis* ATCC 15697 and *B. breve* ATCC 15700 as positive and negative controls respectively. The supernatant was collected at the end of the exponential phase during growth on HMO, and remaining oligosaccharides were purified and reduced, and later detected and quantified by nano HPLC/CHIP TOF MS. Specific oligosaccharide and isomers were identified using two oligosaccharide structures libraries (Wu et al. (2011) *J. Proteome Res.* 10:856; Wu et al. (2010) *J. Proteome Res.* 9:4138). The oligosaccharides quantified include the most abundant neutral and sialylated HMO, and Table 10 shows their names, masses, chemical structure, and degree of polymerization (DP).

Figure 4:
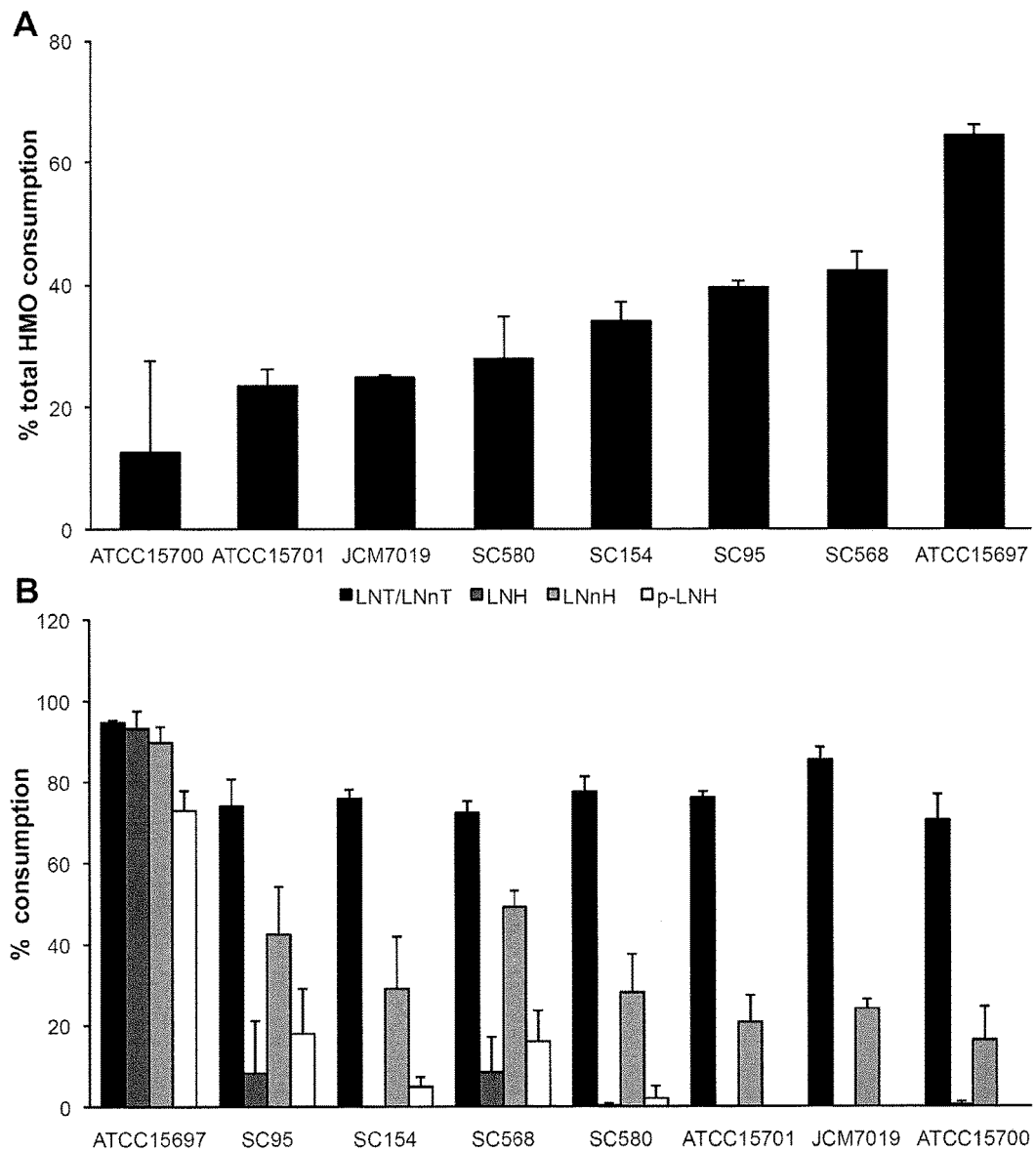
FIG. 4. Glycoprofiling of the HMO consumption by selected *B. breve* strains. (A) Total utilization of HMO. Consumption is calculated as the percent difference in HMO between the start and the end of exponential phase. (B) Glycoprofiles of the consumption of neutral non-fucosylated HMO by seven *B. breve* strains. *B. infantis* ATCC 15697 was included as positive control.

Among the six strains selected, total consumption of HMO ranged between 23 and 42%. These values are lower compared to *B. infantis* ATCC 15697 (64% consumption) but clearly higher than *B. breve* ATCC 15700 (FIG. 4A). FIG. 4B shows the consumption of neutral non-fucosylated HMO in more detail. We observed that for the *B. breve* strains the consumption patterns were similar. All strains were able to deplete LNT/LNnT from the culture media to a high extent. Among three major hexaoses found in HMO, a preference for lacto-N-neohexaose (LNnH) was observed, over lacto-N-hexaose (LNH) and para-lacto-N-hexaose (p-LNH).

Figure 5:
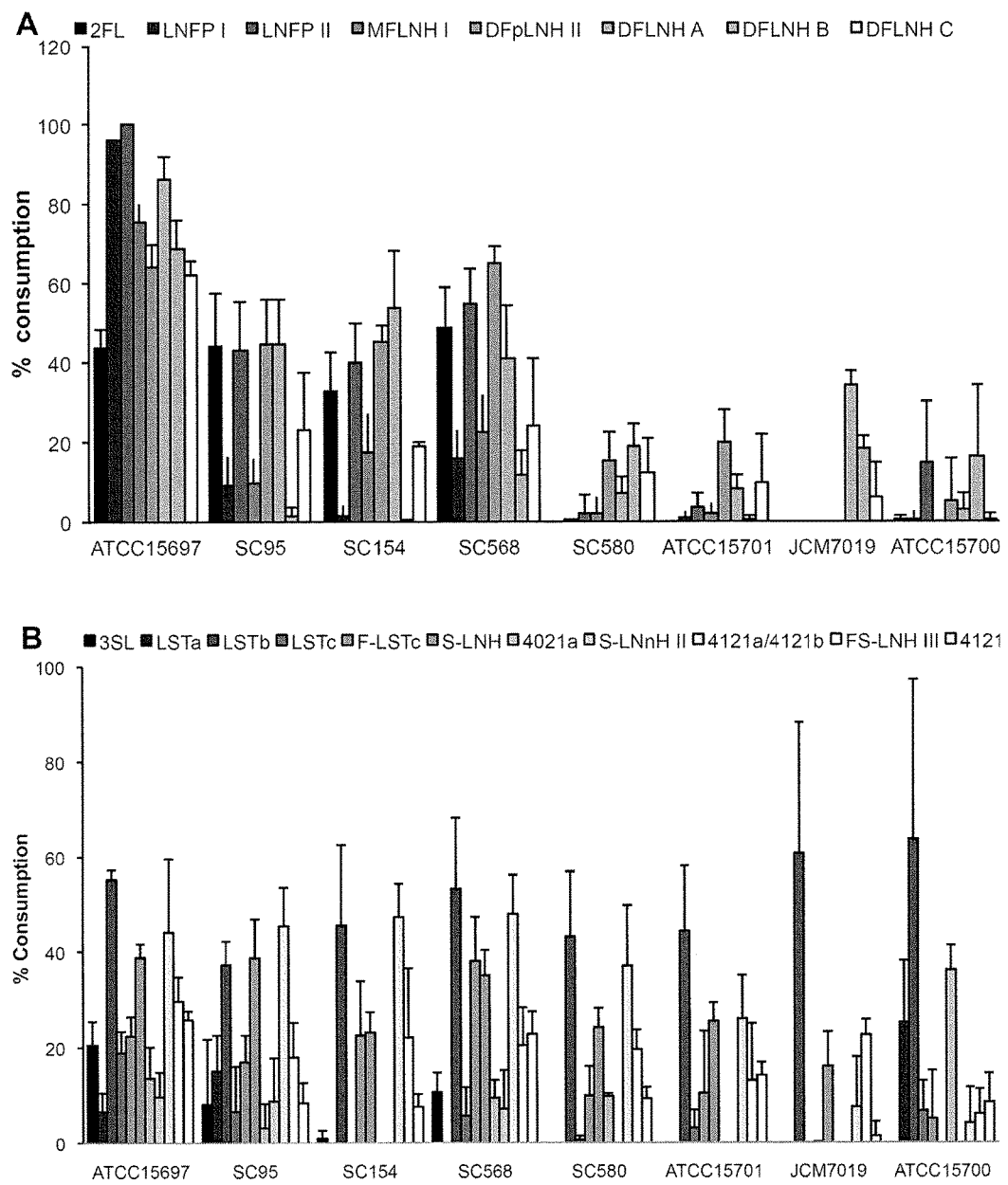
FIG. 5. Glycoprofiling of the consumption of fucosylated and acidic HMO by select *B. breve* strains. Consumption of eight fucosylated HMO (A), and eleven sialylated HMO (B) was calculated. *B. infantis* ATCC 15697 was included as positive control. HMO consumption is represented as the percent difference in HMO between the start and the end of exponential phase.

In general, the ability of *B. breve* to metabolize fucosylated HMO was lower compared to *B. infantis*, which showed high consumption levels for all the HMO tested (FIG. 5A). However, strains SC95, SC154 and SC568 showed a significant consumption of monofucosylated 2FL and LNFPII and difucosylated DFpLNHII and DFLNH-A HMO (FIG. 5A). Interestingly, even though 2FL cannot support the growth in vitro of strain SC154 (Table 8), this strain utilizes larger fucosylated HMO.

Figure 6:
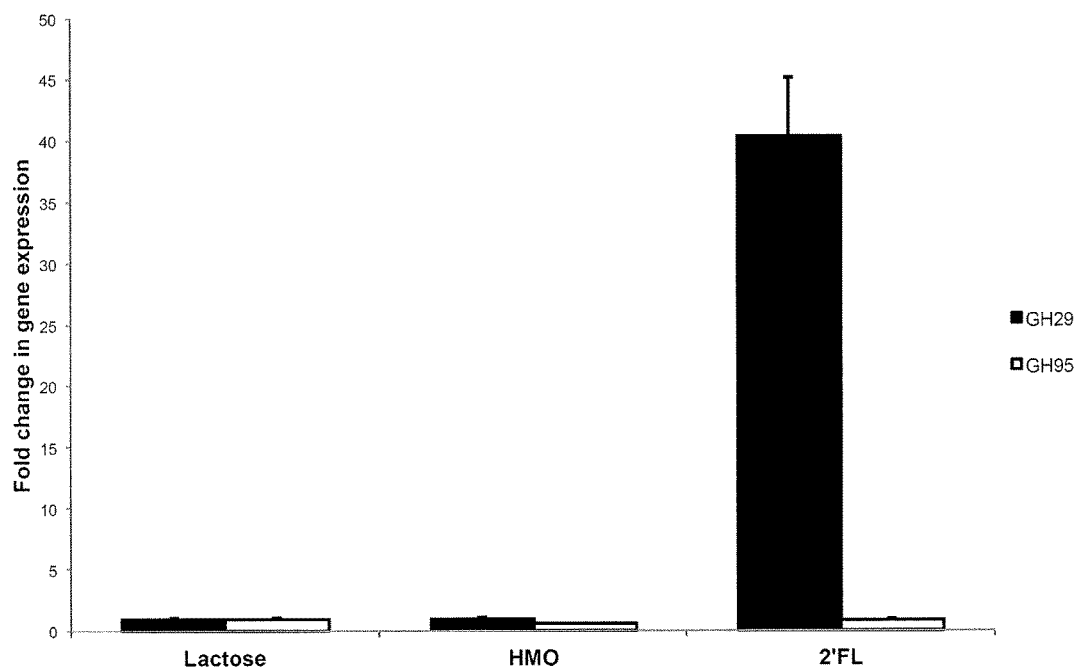
FIG. 6. Fold in change expression for genes encoding α-fucosidases from GH families 95 and 29 in *B. breve* SC95, during mid-exponential growth on HMO and 2FL. Growth on lactose was used as a control.

We observed that growth on fucosylated HMO was more prominent in strains which possessed an additional GH29 α-fucosidase (FIG. 5A and Table 8). We evaluated the relative gene expression of this gene in strain SC95. Growth on 2FL as the sole carbon source up-regulated 40-fold the expression of the GH29 fucosidase gene (FIG. 6). The expression of a GH95 fucosidase was not altered by growth on 2FL, suggesting that the presence of the GH29 fucosidase gene endows these strains with the ability to consume fucosylated oligosaccharides. In contrast, growth on total HMO did not affect the expression of these genes.

Acidic HMO represents approximately 15% of total HMO. We thus screened the consumption of eleven sialylated HMO in the spent supernatants of the listed strains during growth on total HMO (FIG. 5B). The levels of consumption were very similar among the strains tested, and comparable to *B. infantis*. In particular LSTb (sialyl-LNT b), sialyl-lacto-N-hexaose and mass 4121a/4121b were preferentially utilized by *B. breve* (FIG. 5B).

Figure 7:
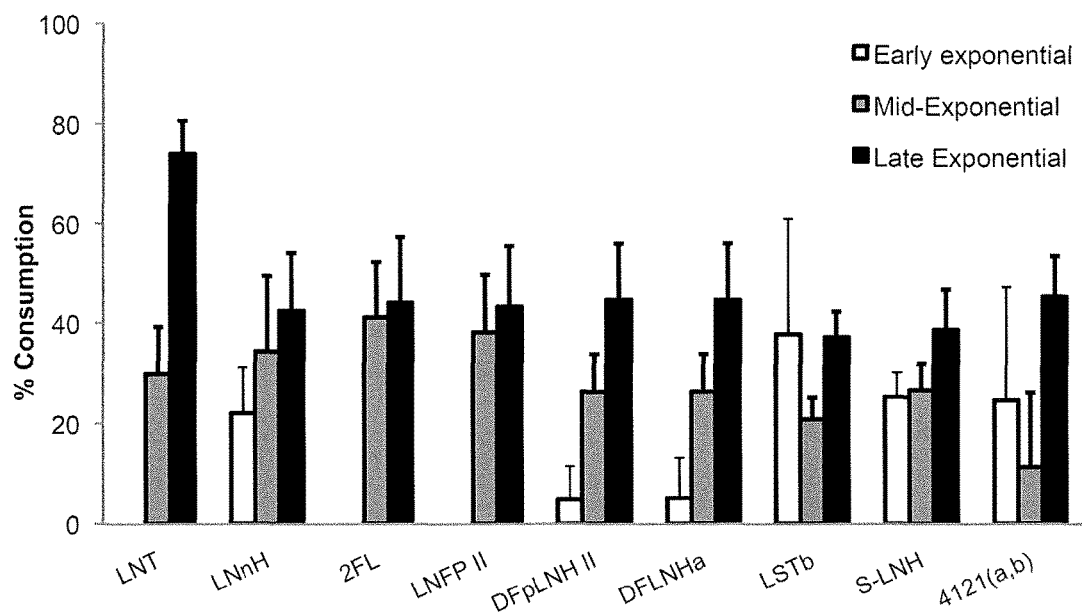
FIG. 7. Temporal glycoprofile of the consumption of select neutral and acidic HMO by *Bifidobacterium breve* SC95 at different stages in the exponential phase.

Finally, to elucidate possible substrate preferences in a *B. breve* strain with high HMO consumption, we monitored the consumption of nine representative oligosaccharides at different points during the fermentation of HMO by strain SC95 (FIG. 7). These HMO correspond to neutral and acid HMO that were consumed at levels higher than 40%. Remarkably, glycoprofiling of early exponential growth revealed that acidic HMO disappeared from the media first, together with LNnH. In contrast, LNT was metabolized first during the mid-exponential phase, and is majorly depleted at the end of the growth on HMO. We also observed that, while monofucosylated HMOs 2FL and LNFP II are depleted from the media at the mid-exponential phase and not later, difucosylated HMO appear to be steadily consumed during the three growth points (FIG. 7).

SUMMARY AND CONCLUSION

*B. breve* is one of the most representative species of bifidobacteria found in the infant intestinal microbiota. In order to determine whether free HMO contribute to the persistence of *B. breve* in the infant intestinal microbiota, we evaluated in detail the adaptations of a significant number of strains of *B. breve* to HMO.

The dominance of *B. breve* in this community has been supported by several studies, especially in breast-fed infants, where this species together with *B. longum* and *B. infantis* can largely outnumber other microorganisms. Breast milk itself is another habitat for this species, which, in addition to the vaginal and fecal microbiota of the mother, contribute to intestinal colonization of the infant. Some strains of this species are currently studied by their probiotic properties, for example in the production of conjugated linoleic acid or important immunomodulatory activities.

Since the predominance of bifidobacteria in breast-fed infants can be attributed in part to bioactive agents in milk such as HMO, the utilization of these substrates in vitro and in vivo is an important reflection of the adaptations of intestinal microorganisms to the environmental conditions prevalent in the infant gut. HMO utilization has only been shown for the type strain of *B. breve* ATCC 15700 (JCM 1192), and results indicate that this microorganism has a limited ability to consume HMO, almost exclusively LNT. Here we have expanded these observations and concluded that several infant-associated strains of *B. breve* can readily utilize HMO, consuming significantly larger amounts of total HMO compared to the type strain ATCC 15700. The HMO consumption in *B. breve* is however moderate by comparison to *B. infantis* ATCC 15697.

Mass spectrometry-based analysis of the HMO remaining after growth provides a detailed representation of the preferences of these strains for different oligosaccharide subsets present in the HMO pool. For example, all strains showed a vigorous growth on LNT and LNnT as a sole carbon source, and the molecular mass representing both oligosaccharide species (709) was the most consumed in pooled HMO. The utilization of LNnT is interesting since this oligosaccharide is not readily fermented by all species of *Bifidobacterium* found in the infant gut. Moreover growth on LNnT was shown to enable *B. infantis* to outcompete *Bacteroides fragilis* in a mouse model.

HMO with mass 1074 Da represent approximately 10% of the total HMO, and includes three neutral isomers, LNH, LNnH and p-LNH (Table 10). Interestingly, LNnH is the most abundant of the three isomers and it was selectively cleared from the growth media compared to the other two isomers. This indicates structure-based preferences in HMO consumption in *B. breve* (FIG. 4B and Table 10).

Strain-dependent differences were more evident in growth of *B. breve* on fucosylated HMO. Fucosidase activity has not been described previously in *B. breve*, and while all the strains studied possessed a gene encoding a GH95 α-fucosidase, we observed that the presence of a second α-fucosidase from GH29 in isolates SC95, SC568 and SC154 correlated with their consistent growth and consumption of fucosylated HMO (FIG. 5A and Table 8). Some strains with this additional GH29 α-fucosidase did not, however, grow on 2FL and 3FL. These smaller HMO are imported by different transport mechanisms. For example, in *B. infantis*, 2FL and larger fucosylated HMO are likely imported by different solute binding proteins.

Remarkably, all *B. breve* strains consume pooled acidic HMO to a significant extent, and an α-sialidase was identified. All strains glycoprofiled showed a preferential consumption of select acidic HMO such as LSTb and S-LNH, but not smaller HMO, which might additionally explain why growth on 3SL and 6SL was negligible (Table 8).

The present results indicate that the mechanisms of HMO consumption in *B. breve* are very similar to *B. infantis*, with a preference to import intact oligosaccharides followed by intracellular degradation, rather than the extracellular degradation observed by *B. bifidum*. For example, *B. breve* strain ATCC 15700 can quickly deplete LNT from the spent media and the absence of intermediate monosaccharides indicates that this strain imports this substrate. Moreover, the GH genes identified in this study lacked signal peptides, indicating intracellular localization. Finally, the sequences obtained are homologous to previously characterized enzymes in *B. infantis*, including β-hexosaminidases Blon_0459, two α-fucosidases Blon_2335 and Blon_0248 and an α-sialidase Blon_0646, indicating a common origin.

The present results provide a rationale for the predominance of *B. breve* in the infant intestinal microbiota, improving our understanding about the ecology of this unique environment. The genetic variation of these strains and the strain-dependent character of the HMO utilization are factors to consider in probiotic and prebiotic studies. Better characterization of the diversity and physiology of beneficial strains of bifidobacteria, and more selective substrates that allow their implantation in the intestine, can be used to design selective synbiotic preparations.

VIII. Informal sequence listing

GH-29, *Bifidobacterium longum* subsp. *infantis* (*B. infantis*), Blon_0248, Genbank Accession YP_002321754 (AfcB); SEQ ID NO: 1:

```
  1 mvlfmanpqr pkmyekfvhd tpewfkgagl gifahwgsys vpawaepiga lgtfddpvyw
 61 nthcpyaewy wntmsikgsp aaehqkevyg dmpyedfidm wkaeafdpad madlfaraga
121 ryfvpttkhh egitlwkapd ndgwntvdrg phrdlvkefa damrdkglkf gvyyssgldw
181 hkepnmpilg dgeygpqsed yarymyshvm dlideyqpsi lwgdidvpki seedndfsva
241 rlfehyydvv pdgvvndrwg lthwdfrtve yeqgkelmgk gmwemtrgig ysfgynqmed
301 adsymtgpea vklladvvsm ggnllldigp daagripelq rqclegmadw mdvnspsihd
361 vepvpeasps gegdgepwvr wtgdgksvya vvdaagrvpl riaadavdad savtlggsav
421 avdadgdvlt advpasevag pqvvhfvrr
```

GH-29, *Bifidobacterium longum* subsp. *infantis* (*B. infantis*), Blon_0426, Genbank Accession YP_002321924 (AfcB); SEQ ID NO: 2:

```
  1 mvlfmanpqr pkmyekfvhd tpewfkgagl gifahwgsys vpawaepiga lgtfddpvyw
 61 nthcpyaewy wntmsikgsp aaehqkevyg dmpyedfidm wkaeafdpad madlfaraga
121 ryfvpttkhh egitlwkapd ndgwntvdrg phrdlvkefa damrdkglkf gvyyssgldw
181 hkepnmpilg dgeygpqsed yarymyshvm dlideyqpsi lwgdidvpki seedndfsva
241 rlfehyydvv pdgvvndrwg lthwdfrtve yeqgkelmgk gmwemtrgig ysfgynqmed
301 adsymtgpea vklladvvsm ggnllldigp daagripelq rqclegmadw mdvnspsihd
361 vepvpeasps gegdgepwvr wtgdgksvya vvdaagrvpl ridagavdvd satilgggnv
421 vveadgdmlt veipatdvag pqvvrfarh
```

GH-29, *Bifidobacterium breve* (*B. breve*) SC95, (AfcB); SEQ ID NO: 3:

```
  1 mvlfmanpqr pkmyekfvhd tpewfkgagl gifahwgsys vpawaepiga lgtfddpvyw
 61 nthcpyaewy wntmsikgsp aaehqkevyg dmpyedfidm wkaeafdpad madlfaraga
121 ryfvpttkhh egitlwkapd ndgwntvdrg phrdlvkefa damrdkglkf gvyyssgldw
181 hkepnmpilg dgeygpqsed yarymyshvm dlidkyqpsi lwgdidvpki seedndfsva
241 rlfehyydvv pdgvvndrwg lthwdfrtve yeqgkelmgk gmwemtrgig ysfgynqmed
301 adsymtgpea vklladvvsm ggnllldigp daagripelq rqclegmadw myvnspsihd
361 vepvpeasps gegdgepwvr wtgdgksvya vvdaagrvpl riaadavdad savtlggsav
421 avdadgdvlt advpasevag pqvvhfvrr*
```

| VIII. Informal sequence listing |
| --- |

GH-29, *Bifidobacterium bifidum*, Genbank Accession BAH80310.1 (AfcB);
SEQ ID NO: 4:

```
   1 mlhtasrgcs rswlrrltal iaysalafva lpnvavaadp meyldvsfgg tfaadtyttg
  61 gdevakgpvt khgsiptkld gggitlaggt ngvtftstas fsesgkvnkg fraemeyrtt
 121 qtpsnlatlf samgnifvra ngsnleygfs tnpsgstwnd ytksvtlpsn nvkhiiqlty
 181 lpgadgaast lqlsvdgvag etatsaagel aaysdsvgnk fgigyevnpa sgaasrglag
 241 dvfrarvads dapweildas qllhvnfngt fsgtsytaas geqmlgslvs rsanpsisns
 301 avtlgggtag fdftptdftl gdneaitrpl vaelrftptq tgdnqtlfga ggnlflryes
 361 nklvfgastk sgdnwtdhki esaaatgaeh vvsvayvpnk agtgaklvmr vdggdaqtkd
 421 itglaylnss ikgkvgfgnd vhtdalsrgf vgslseirla etsanfttne fklvysqvsc
 481 dtsgikeant fdvepaecea alktklsklr pteggqadyid wgqigflhyg intyynqewg
 541 hgnedpsrin ptgldtdqwa ksfadggfkm imvtvkhhdg felydsrynt ehdwantava
 601 krtgekdlfr kivasakkyg lkvgiyyspa dsymerkgvw gnnsarvert iptivenddr
 661 agkvasgklp tfkykatdyg aymlnqlyel lteygdisev wfdgaqgnta gtehydygvf
 721 yemirrlqpq aiqanaayda rwvgnedgwa rqtewspqaa yndgvdkvsl kpgqmapdgk
 781 lgsmssvlse irsgaanqlh wypaevdakn rpgwfyrasq spasvaevvk yyeqstgrns
 841 qyllnvppsd tgkladadaa glkglgeela rrygtdlalg ksatvaasan dtavaapklt
 901 dgsklssdka vgntptytid lgstvavdav kisedvrnag qqiesatlqg rvngtwtnla
 961 tmttvgqqrd lrftsqnida irlvvnssrg pvrlsrlevf hteseiqtga rayyidptaq
1021 tagdgftkdk pmtsieqlhd vtvapgsvif vkagteltgd favfgygtkd epitvttyge
1081 sdkattasfd gmtagltlkq alkalgkdda gwvvadsata pasrvyvpqd eisvhaqssq
1141 nsgaeaaral dgdsstswhs qyspttasap hwvtldlgks renvayfdyl aridgnnnga
1201 akdyevyvsd dpndfgapva sgtlknvayt qrikltpkng ryvkfviktd ysgsnfgsaa
1261 emnvellpta veedkvatpq kptvdddadt ytipdiegvv ykvdgkvlaa gsvvnvgded
1321 vtvtvtaepa dgyrfpdgvt spvtyeltft kkggekppte vnkdklhati tkaqaidrsa
1381 ytdeslkvld dklaaalkvy dddkvsqddv daaeaalsaa idalktkptt pggegekpge
1441 gekpgdgnkp gdgkkpgdvi aktgastmgv vfaalamvag avvtleakrk snr
```

GH-95, *Bifidobacterium longum* subsp. *infantis* (*B. infantis*), Blon_2335, Genbank Accession YP_002323771.1 (AfcA); SEQ ID NO: 5:

```
   1 mkltfdgiss hweegipfgn grmgavlcse pdadvlylnd dtlwsgypha etspltpeiv
  61 akarqassrg dyvsatriiq datqrekdeq iyepfgtaci rysseagerk hvkrsldlar
 121 alagesfrlg aadvhvdawc sapddllvye msssapvdas vsvtgtflkq trisssgsdsd
 181 arqativvmg qmpglnvgsl ahvtdnpwed erdgigmaya gafsltvtgg eitviddvlq
 241 csgvtglslr frslsgfkgs aeqperdmtv ladrlgetia awpsdsraml drhvadyrrf
 301 fdrvgvrlgp andddeevpf aeilrskedt phrletlsea mfdfgrylli sssrphtqps
 361 nlqgiwnhkd fpnwysaytt niniemnywm tgpcalkeli eplvamnrel lepghdaaga
 421 ilgcggsavf hnvdiwrral pangeptwaf wpfgqawmcr nlfdeylfnq desylasiwp
 481 imrdsarfcm dflsdtehgl apapatspen yfvvdgetia vahtsentta ivrnllddli
 541 haaqtmpdld dgdkalvrea estraklaav rvgsdgrile wndelveadp hhrhlshlye
 601 lhpgagitan tprleeaark slevrgddgs gwsivwrmim warlrdaeha eriigmflrp
 661 veadaetdll gggvyasgmc ahppfqidgn lgfpaalaem lvqshdgmvr ilpalpedwh
```

| VIII. Informal sequence listing |
| --- |

```
 721 egsfhglrar gglsvdaswt ddaieytlrc tkpatitliv dgtdatqvrl spdepfkglv
 781 rr
```

GH-95, *Bifidobacterium bifidum*, Genbank Accession AAQ72464.1 (AfcA); SEQ ID NO: 6:

```
    1 mkhramssrl mplvascatv gmllaglpvs avavgttraa asdassstta titpsadttl
   61 qtwtseknss maskpyigtl qgpsqgvfge kfestdaadt tdlktglltf dlsaydhapd
  121 satfemtylg yrgnptatdt dtikvtpvdt tvctnnatdc ganvatgatk pkfsindssf
  181 vaeskpfeyg ttvytgdait vvpantkkvt vdvteivrqq faegkkvitl avgetkktev
  241 rfassegtts lngatadmap kltvsystkd dlkpsadttl qawaseknek kntaayvgal
  301 qpegdygdfg ekfkstdvhd vtdakmglmt fdlsdytaap ehsiltltyl gyagadktat
  361 atdkvkvvav dtsrctgtap cdtnnatwan rpdfevtdtt ktatshafay gskkysdgmt
  421 vesgnakkvl ldvsdvikae fakfsagate kkitlalgel nksdmrfgsk evtsltgate
  481 amqptlsvtk kpkaytlsie gptkvkyqkg eafdkaglvv katstadgtv ktltegnged
  541 nytidtsafd sasigvypvt vkynkdpeia asfnayvias vedggdgdts kddwlwykqp
  601 asqtdatata ggnygnpdnn rwqqttlpfg ngkiggtvwg evsrervtfn eetlwtggpg
  661 sstsynggnn etkgqngatl ralnkqlang aetvnpgnit ggenaaeqgn ylnwgdiyld
  721 ygfndttvte yrrdlnlskg kadvtfkhdg vtytreyfas npdnvmvarl taskagklnf
  781 nvsmptntny sktgetttvk gdtltvkgal gnngllynsq ikvvldngeg tlsegsdgas
  841 lkvsdakavt lyiaaatdyk qkypsyrtge taaevntrva kvvqdaankg ytavkkahid
  901 dhsaiydrvk idlgqsghss dgavatdall kayqrgsatt aqkreletiv ykygryltig
  961 ssrensqlps nlqgiwsvta gdnahgntpw gsdfhmnvnl qmnywptysa nmgelaepli
 1021 eyveglvkpg rvtakvyaga ettnpettpi gegegymaht entaygwtap gqsfswgwsp
 1081 aavpwilqnv yeayeysgdp alldrvyall keeshfyvny mlhkagsssg drlttgvays
 1141 peqgplgtdg ntyesslvwq mlndaieaak akgdpdglvg nttdcsadnw akndsgnftd
 1201 ananrswsca ksllkpievg dsgqikewyf egalgkkkdg stisgyqadn qhrhmshllg
 1261 lfpgdlitid nseymdaakt slryrcfkgn vlqsntgwai gqrinswart gdgnttyqlv
 1321 elqlknamya nlfdyhapfq idgnfgntsg vdemllqsns tftdtagkky vnytnilpal
 1381 pdawaggsys glvargnftv gttwkngkat evrltsnkgk qaavkitagg aqnyevkngd
 1441 tavnakvvtn adgasllvfd ttagttytit kkasanvpvt gvtvtganta tagdtvtlta
 1501 tvapanatdk svtwstsdaa vatvnangvv ttkkagkvti tatsngdktk fgsieitvsa
 1561 atvpvtsvtv agdaamtvdg eqtltatvap atatdktvtw kssdatvatv dangkvvakk
 1621 agevtitata ggvsgtlkit vsdkaptvip vqsvtvtgkq elvegasttl tatvapadat
 1681 dktvtwkssd esvatvdkdg vvtakkagtv titataggvs gtlhitvtak pvetvpvtsv
 1741 evtveagttv svgktlqata tvkpgnatnk kvtwkssdes iatvdangvi takkagkvvi
 1801 tatstdgtdk sgsveitvvd etkptpdhks vkadtgdvta gktgtvtepk dvagwksrsi
 1861 ikqgklgkae iadgtivyaa gdktgddsfv vqytmadgtv idvtysvtvk aaetgkndgd
 1921 gkgdgvaktg aavgalaglg lmllavgvsv vmirrkhsa
```

-continued

| VIII. Informal sequence listing |
|---|

GH-29, *Bifidobacterium longum* subsp. *infantis* (*B. infantis*), Blon_0248, derived from Genbank Accession NC_011593, (AfcB); SEQ ID NO: 7:

```
   1 atggtgttgt tcatggccaa tccacagcgt cccaagatgt atgagaagtt cgtgcacgat
  61 acacccgaat ggttcaaggg cgccggtctc ggcatcttcg cccactgggg ttcgtattcg
 121 gtgccggcat gggcggagcc gatcggtgcg cttggcacct ttgacgatcc ggtgtactgg
 181 aacacccact gcccgtatgc ggaatggtat tggaacacga tgagcatcaa gggctcgccg
 241 gcggccgagc atcagaagga agtctacggt gacatgccgt atgaggactt catcgacatg
 301 tggaaggccg aggcgttcga ccccgcggac atggccgacc tgttcgcacg cgccggtgcc
 361 cggtacttcg tgccgaccac gaagcatcac gaaggcatca cgctgtggaa ggcccccgac
 421 aacgatgggt ggaataccgt ggaccgtggt ccgcatcgcg atctggtcaa ggaattcgcc
 481 gacgccatgc gcgacaaggg actgaagttc ggcgtgtact actcctcggg cctcgactgg
 541 cacaaggagc ccaacatgcc gattctcggc gacggggaat acgggccgca gagcgaggac
 601 tacgcccgct atatgtactc gcatgtgatg gacctcatcg acgaatacca gccgtccatc
 661 ctgtggggag atatcgacgt gccgaagatc tcggaggagg acaacgattt cagcgtggcc
 721 cgactgttcg agcattacta cgacgtggtg ccggatggtg tggtcaacga ccgctggggc
 781 ctgacccatt gggacttccg caccgtcgaa tacgaacagg caaggagct catgggcaag
 841 ggcatgtggg agatgacccg aggcatcggc tactccttcg gctacaacca gatggaggac
 901 gccgactcct acatgaccgg tccggaggcg gtgaagttgc tcgccgacgt ggtctccatg
 961 ggcggcaacc tgctgctcga catcggcccc gacgccgccg gacgcatccc cgaactgcag
1021 cgtcagtgcc tcgagggcat ggccgactgg atggacgtga actcgccgag tatccatgat
1081 gtcgaaccgg tgccggaagc ctcgccttcc ggagaggggg acggcgagcc atgggtccgt
1141 tggaccggag acgcaagag cgtctatgcc gtcgtcgatg ctgcgggcag ggttccgctg
1201 cgcatcgccg ccgatgctgt ggacgcggat tccgccgtga cgcttggcgg atccgcagtc
1261 gccgtggacg ccgacggcga cgtgctgacc gccgatgttc cggcctcgga agtggcgggg
1321 ccgcaggtcg tgcacttcgt ccgtcgctga
```

GH-29, *Bifidobacterium longum* subsp. *infantis* (*B. infantis*), Blon_0426, derived from Genbank Accession NC_011593, (AfcB); SEQ ID NO: 8:

```
   1 atggtgttgt tcatggccaa tccacagcgt cccaagatgt atgagaagtt cgtgcacgat
  61 acacccgaat ggttcaaggg cgccggtctc ggcatcttcg cccactgggg ttcgtattcg
 121 gtgccggcat gggcggagcc gatcggtgcg cttggcacct ttgacgatcc ggtgtactgg
 181 aacacccact gcccgtatgc ggaatggtat tggaacacga tgagcatcaa gggctcgccg
 241 gcggccgagc atcagaagga agtctacggt gacatgccgt atgaggactt catcgacatg
 301 tggaaggccg aggcgttcga ccccgcggac atggccgacc tgttcgcacg cgccggtgcc
 361 cggtacttcg tgccgaccac gaagcatcac gaaggcatca cgctgtggaa ggcccccgac
 421 aacgatgggt ggaataccgt ggaccgtggt ccgcatcgcg atctggtcaa ggaattcgcc
 481 gacgccatgc gcgacaaggg actgaagttc ggcgtgtact actcctcggg cctcgactgg
 541 cacaaggagc ccaacatgcc gattctcggc gacggggaat acgggccgca gagcgaggac
 601 tacgcccgct atatgtactc gcatgtgatg gacctcatcg acgaatacca gccgtccatc
 661 ctgtggggag atatcgacgt gccgaagatc tcggaggagg acaacgattt cagcgtggcc
 721 cgactgttcg agcattacta cgacgtggtg ccggatggtg tggtcaacga ccgctggggc
```

-continued

VIII. Informal sequence listing

```
 781 ctgacccatt gggacttccg caccgtcgaa tacgaacagg gcaaggagct catgggcaag 841 ggcatgtggg agatgacccg aggcatcggc tactccttcg gctacaacca gatggaggac 901 gccgactcct acatgaccgg tccggaggcg gtgaagttgc tcgccgacgt ggtctccatg 961 ggcggcaacc tgctgctcga catcggcccc gacgccgccg gacgcatccc cgaactgcag 1021 cgtcagtgcc tcgagggcat ggccgactgg atggacgtga actcgccgag tatccatgat 1081 gtcgaaccgg tgccggaagc ctcgccttcc ggagaggggg acggcgagcc atgggttcgt 1141 tggaccggag acggcaagag cgtctatgcc gtcgtcgatg ctgcgggcag ggttccgctg 1201 cgcatagatg cgggtgcggt cgatgtggat tccgcaacca ttcttggcgg tggcaacgtt 1261 gtcgtggagg cggacggcga tatgctgacc gtggagattc ccgcgacaga cgtcgccggc 1321 cctcaggtcg tgcgttttgc tcgacactaa
```

GH-29, *Bifidobacterium breve* SC95, (AfcB), SEQ ID NO: 9:

```
   1 atggtgctgt tcatggccaa tccgcagcgt cccaagatgt atgagaagtt cgtgcacgat 61 acacccgaat ggttcaaggg cgccggtctc ggcatcttcg cccactgggg ttcgtattcg 121 gtgccggcat gggcggagcc gatcggtgcg cttggcacct ttgacgatcc ggtgtactgg 181 aacacccact gcccgtatgc ggaatggtat tggaacacga tgagcatcaa gggctcgccg 241 gcggccgagc atcagaagga agtctacggt gacatgccgt atgaggactt catcgacatg 301 tggaaggccg aggcgttcga ccccgcggac atggccgacc tgttcgcacg cgccggtgcc 361 cggtacttcg tgccgaccac gaagcatcac gaaggcatca cgctgtggaa ggcccccgac 421 aacgatgggt ggaataccgt ggaccgtggt ccgcatcgcg atctggtcaa ggaattcgcc 481 gacgccatgc gcgacaaggg actgaagttc ggcgtgtact actcctcggg cctcgactgg 541 cacaaggagc ccaacatgcc gattctcggc gacggggaat acgggccgca gagcgaggac 601 tacgcccgct atatgtactc gcatgtgatg gacctcatcg acaaatacca gccgtccatc 661 ctgtggggag atatcgacgt gccgaagatc tcggaggagg acaacgattt cagtgtggcc 721 cgactgttcg agcattacta tgacgtggtg ccggatggtg tggtcaacga ccgctggggc 781 ctgacccatt gggacttccg caccgtcgaa tacgaacagg gcaaggagct catgggcaag 841 ggcatgtggg agatgacccg aggcatcggc tactccttcg gctacaacca gatggaggac 901 gccgactcct acatgaccgg tccggaggcg gtgaagttgc tcgccgacgt ggtctccatg 961 ggcggcaacc tgctgctcga catcggcccc gacgccgccg gacgcatccc cgaactgcag 1021 cgtcagtgcc tcgagggcat ggccgactgg atgtacgtga actcgccgag tatccatgat 1081 gtcgaaccgg tgccggaagc ctcgccttcc ggagaggggg acggcgagcc atgggtccgt 1141 tggaccggag acggcaagag cgtctatgcc gtcgtcgatg ctgcgggcag ggttccgctg 1201 cgcatcgccg ccgatgctgt ggacgcggat tccgccgtga cgcttggcgg atccgcagtc 1261 gccgtggacg ccgacggcga cgtgctgacc gccgatgttc cggcctcgga agtggcgggg 1321 ccgcaggtcg tgcacttcgt ccgtcgctga
```

GH-29, *Bifidobacterium bifidum*, Genbank Accession, AB474964.1 (AfcB); SEQ ID NO: 10:

```
   1 atgctacaca cagcatcaag aggatgctcg cgttcgtggc tgcgcagact caccgcattg 61 atagcggtct cggcgctcgc gttcgtggca ttgccgaacg tcgcggtggc ggcggatccg 121 atggaatacc tcgatgtgtc gttcggcggc acgttcgctg cagacaccta caccacaggt 181 ggcgacgagg tggcgaaggg ccccgtgacc aagcacggca gcataccgac caagcttgac
```

VIII. Informal sequence listing

```
 241 ggcggcggca tcaccctcgc tggcggcacc aacggcgtga cattcacctc gaccgcgagc
 301 ttcagcgaga gtgggaaggt gaacaaggga ttccgcgccg aaatggagta ccgtacgacg
 361 cagacgccca gcaacctcgc cacattgttc tccgccatgg caacatctt cgtgcgggcg
 421 aacggcagca acctcgaata cggcttctcc acgaacccttc ccggcagtac atggaacgac
 481 tacacaaagt ccgtgacgct gccttccaac aatgtgaagc acatcatcca gctgacatat
 541 ctgccgggag ccgacggcgc tgcctcgacg ttgcagttgt cggtggatgg cgtggccggc
 601 gagaccgcca cctccgcggc cggcgagctc gcggccgtca gcgattccgt cgggaacaag
 661 ttcgggatcg gctacgaggt gaaccccgct tccggcgcgg cgagccgcgg tcttgccggt
 721 gacgtgttcc gcgcgcgtgt cgccgattcg gacgccccgt gggagattct tgacgcatcc
 781 cagctgctgc atgtcaattt caacggcacg ttcagcggca cctcatatac cgcggcgagc
 841 ggcgagcaga tgctgggctc gctggtgtcg cgctcggcca atccgtccat ctcgaactcc
 901 gccgtcacgc tgggcggcgg cacggccgga ttcgatttca cgcccacgga cttcacccctc
 961 ggtgacaacg aggccatcac ccgcccgctg gtcgcggagc tgcgcttcac cccgacgcag
1021 accggcgaca accagaccct gttcggcgcg ggcggcaacc tgttcctgcg ctacgagtcg
1081 aacaagctcg tgttcggcgc ctccaccaag tccggcgata attggaccga ccacaagatc
1141 gagtccgcgg ccgccacggg tgcggagcac gtcgtgtcgg tggcgtacgt gcccaataag
1201 gccggcaccg gcgcgaagct tgtcatgcgc gtggatggcg cgacgccca gaccaaggac
1261 atcactggtc tggcttacct gaattcgagc atcaagggca aggtcggctt cggcaacgac
1321 gtgcataccg acgcgctcag ccgcggcttc gtcggctcgc tgagcgagat ccgcctggcc
1381 gaaacctccg cgaacttcac caccaacgaa ttcaagctgg tctactctca ggtcagctgc
1441 gacacgtcgg gcatcaagga ggcgaatacc ttcgacgtgg agcccgccga gtgcgaggcc
1501 gcgcttaaga ccaagctgtc caagctgcgt ccgaccgaag gcaggccga ctacatcgac
1561 tggggtcaga tcggattcct ccattacggc atcaacacgt actacaacca ggagtggggt
1621 cacggtaacg aggatccctc ccgcatcaac ccgaccggcc tcgacaccga ccagtgggcg
1681 aagtccttcg ccgacggtgg cttcaagatg atcatggtga cggtcaagca ccatgacggt
1741 ttcgagctgt acgactcgcg gtacaacacc gagcacgact gggcaaacac cgccgtcgcc
1801 aagcgcacgg gggagaagga cctgttccgc aagattgtcg cctcggcgaa gaaatacggc
1861 ctgaaggtcg gcatctacta ttcgccggcc gattcctaca tggagaggaa gggcgtctgg
1921 ggcaacaact ccgcacgcgt cgagcgcacg atccccacgc tggtggagaa cgacgaccgc
1981 gccggcaagg tggcttccgg caaactgccc acgttcaagt acaaggccac ggattacggc
2041 gcctacatgc tcaaccagct ctatgagctg ctgactgagt acggcgacat ctccgaggtc
2101 tggttcgacg tgcccaagg caacaccgca ggcactgagc attacgacta tggcgtgttc
2161 tacgagatga tccgccggct tcagccccag gcaattcagg ccaacgccgc atacgatgcc
2221 cgatgggtgg gcaacgagga cggctgggcc cgtcagaccg agtggagccc gcaggcggca
2281 tacaacgacg cgtggacaa ggtgtcgctc aagcctggcc agatggcccc cgacggtaag
2341 cttggcagca tgtcgagcgt gctgtccgag atccgcagcg gcgccgccaa ccagctgcac
2401 tggtatccgg ccgaagtcga cgccaagaac cggcccggat ggttctaccg tgccagccaa
2461 tcgccggcgt ccgtagccga agtcgtgaag tactacgagc agtccacggg acgcaactcg
2521 cagtatctgc tgaacgtccc accgtccgat accggcaagc tcgccgatgc ggatgccgcg
```

VIII. Informal sequence listing

```
2581 ggacttaagg ggctgggcga ggagctcgcc cgacgctacg gcaccgatct tgccctgggc 2641 aagagcgcga ccgtcgccgc gtccgcgaac gacactgcgg tagcggcccc gaagctgacc 2701 gacggttcga agctctcctc cgacaaggcc gtgggcaata cgccgacgta caccatcgat 2761 ctgggcagca ctgtcgccgt ggatgcagtg aagatctccg aggacgtgcg caatgccggc 2821 cagcagatcg aaagcgccac tctgcaggga cgagtcaatg aacatggac gaatctggcg 2881 actatgacga cggtcgggca gcagcgcgac cttcgcttca cgtcccagaa catcgatgcc 2941 atccgtctgg tggtcaactc ctcccgcggt ccggtgcgtc tgagccgtct tgaggtgttc 3001 cacaccgaat ccgagattca gaccggcgcc cgcgcctact acatcgatcc gacggcgcag 3061 accgcgggag atggattcac gaaggacaag cccatgacgt cgatcgagca gctgcacgat 3121 gtgaccgtcg cgccaggctc cgtgatcttc gtcaaggcgg gcaccgagct gaccggggac 3181 ttcgccgtct tcggctacgg caccaaggac gagcccatca ccgtgacgac atacggcgaa 3241 agcgacaaag ccaccaccgc gagcttcgac ggcatgaccg ccgggctgac gctgaagcag 3301 gcgctgaagg cgctcggcaa ggacgacgcc ggctgggtcg tggccgattc cgccactgca 3361 ccggcctccc gcgtgtatgt cccgcaggat gagatcagcg tgcacgccca gtcgtcgcag 3421 aactccggcg cagaggcggc gagggcgctc gacggcgact cgtcgacgag ctggcactcc 3481 cagtacagcc cgaccaccgc gtctgctccg cattgggtga ctctcgatct cggcaaatcg 3541 cgtgagaacg tcgcctactt cgactacctc gcccgtatcg acggcaacaa taacggtgcc 3601 gccaaggatt acgaggtgta tgtctccgac gatcccaacg attttggagc ccctgtggcc 3661 tcgggcacgt tgaagaacgt cgcctacacg cagcgcatca agctgacccc caagaacgga 3721 cggtacgtca agttcgtcat caagaccgat tattccggat cgaacttcgg ctccgcggcg 3781 gaaatgaatg tcgagttgct gcccacggcc gtagaggagg acaaggtcgc caccccgcag 3841 aagccgacag tggacgatga tgccgataca tacaccatcc ccgacatcga gggagtcgtg 3901 tacaaggtcg acggcaaggt gttggccgct ggttccgtag tgaacgtggg cgatgaggac 3961 gtgaccgtca cggtcaccgc cgagcccgcc gacggatacc gcttcccgga tggtgtgacg 4021 tcccccagtca cgtatgagct gacgttcacc aagaagggtg gcgagaagcc tccgaccgaa 4081 gtcaacaagg acaagctgca cgccacgatc accaaggctc aggcgatcga ccgttccgcc 4141 tatacggacg agtcgctcaa ggtgcttgat gacaagctcg ccgcagcgct caaggtctat 4201 gacgatgaca aggtgagcca ggatgatgtc gatgccgccg aggcggctct gtctgcggcg 4261 atcgacgcgc tgaagaccaa gccgacgacc cccggcggtg aaggtgagaa gcctggtgaa 4321 ggtgaaaagc ccggtgacgg caacaagccc ggtgacggca agaagcccgg cgacgtgatc 4381 gcaaagaccg gcgcctccac aatgggcgtt gtcttcgctg cactcgcgat ggtagcgggt 4441 gcggtcgtga cgcttgaagc caagcgtaag tccaaccggt aa
```

GH-95, *Bifidobacterium longum* subsp. *infantis* (*B. infantis*), Blon_2335, derived from Genbank Accession NC_011593 (AfcA); SEQ ID NO: 11:

```
  1 ctacctgcgg acaagcccct tgaacggctc gtcgggagac agtcggacct gcgtcgcgtc 61 ggtgccatcg acgatcaggg tgatcgtcgc gggcttcgtg cagcgcagcg tgtattcgat 121 ggcgtcgtcc gtccaggagg cgtccaccga aaggcctccc ctggcgcgca ggccatggaa 181 gctgccttca tgccaatcct cgggcaacgc gggcaggatg cgcaccatgc cgtcatgact 241 ctggacgagc atctccgcca gagccgcggg gaagcccaga ttgccgtcga tctggaatgg
```

```
301 gggatgcgcg cacatgccgc tggcatacac gccgccgcca agcagatcgg tttcggcgtc 361 ggcttcgacc gggcggagga acatgccgat gatgcgttcg gcgtgctcag cgtcccgcag 421 acgcgcccac atgatcatgc gccacacgat gctccagccg gaaccgtcgt cgccacgcac 481 ttcgagggac ttcctggcgg cctcctccag acgcggggtg ttcgcggtga tgcctgcgcc 541 cggatgcagt tcgtacaggt gggacaggtg acggtgatgc ggatccgcct cgacgagttc 601 atcgttccat tcgagaatcc tgccatcgga tcccacgcgg acagccgcca gcttcgcgcg 661 ggtggattcc gcctcccgca ccaaggcctt gtcgccgtca tccaggtcgg gcatggtttg 721 cgccgcgtgg atcagatcat cgagcagatt gcgcacgatg gccgtggtgt tttcgctggt 781 gtgggcgacg gcgatcgttt cgccgtccac gacgaagtag ttttccggcg atgtcgccgg 841 agccggggcc agaccgtgtt ccgtatccga cagaaaatcc atgcagaatc gcgcgctgtc 901 ccgcatgatc ggccagatgg aagccagata cgactcatcc tggttgaaca ggtactcatc 961 gaacaggttc cggcacatcc acgcctggcc gaacggccag aacgcccacg tcggctctcc 1021 gttcgccggc agcgccctgc gccagatatc gacattgtgg aagaccgcgg aaccaccgca 1081 tccgaggatg gcgccggccg catcatgccc cggttccagc agctccctgt tcatggcgac 1141 gagcggttcg atgagctcct gagggcgca tgggccggtc atccaatagt tcatctcgat 1201 gttgatgttc gtcgtgtagg cgctatacca gttcgggaag tccttatggt tccagattcc 1261 ctgcagattc gacggctggg tatgcggcct ggacgaggag atcagcaggt atcggccgaa 1321 atcgaacatc gcctcggaga gcgtctccag acggtgcggc gtatcctcct ggagcgcag 1381 gatctcggcg aacggcacct cctcatcgtc gtcatgggcc gggccgagac gcacgccgac 1441 ccggtcgaag aaccggcggt agtcggcgac gtgacggtca agcatcgccc gcgaatcgga 1501 cggccatgcg gcgatggtct cgcccagccg atcggcgagc accgtcatgt cccgctccgg 1561 ctgttcggcg cttcccttga acccgctcag gctgcggaac cgaagcgaca gccggtgac 1621 gcccgagcac tgcagaacat catcgatcac cgtgatctcg ccgcccgtga cggtgaggga 1681 gaaggcgccg gcatacgcca tcccgatgcc gtcccgttcg tcctcccatg gattatcggt 1741 gacatgggcc aatgatccga cattgagtcc gggcatctgc cccatgacga cgagggtggc 1801 ctggcgcgca tcggaatcag accccgacga tatccgggtc tgcttgagaa agtgccggt 1861 gacgctcacg ctcgcatcga ccggcgcgct cgacgacatc tcatacacca gcagatcatc 1921 gggagcgctg caccatgcgt cgacatggac gtcggcggcg cccagccgga acgattcgcc 1981 ggcgagggcc ctggcgaggt ccaggctgcg cttcacatgc ttccgttcgc cggcctccga 2041 cgagtaccgg atgcaagccg tgccgaacgg ctcgtatatc tgctcgtcct tctcccgctg 2101 cgtggcgtcc tggatgatcc gcgtggccga cacgtaatcg ccgcgagacg acgcctgacg 2161 ggctttggcc acgatttcgg gcgtcaacgg cgaggtctcc gcatgcggat agcccgacca 2221 gagggtgtcg tcgttgaggt acagcacatc cgcgtccggt tcggagcaca ggaccgcccc 2281 catgcgaccg ttgccgaacg ggattccttc ctcccaatgc gaagaaatcc catcgaaagt 2341 gagtttcat
```

GH-95, *Bifidobacterium bifidum*, Genbank Accession AY303700, (AfcA); SEQ ID NO: 12:

```
  1 aacggtatcc agggactctc tgagagctgt ggttccaatt gaagacacaa gtcgccgacg 61 gacttgattc ttttagtaaa caatgtatat attaatatga accggcaaag ctgctggctg 121 tcctatagga gaaagaacca aatatgaaac atagagcgat gtcatcgcgt ctgatgccac
```

VIII. Informal sequence listing

```
 181 tggtggcgtc ctgcgcgacg gtcggcatgc tgctggccgg actacctgtg tcggccgtcg
 241 cggtcggcac gacgagagcg gcagcgtccg acgcctcgtc ctccaccaca gcaaccatca
 301 cccccctccgc cgataccacg ttgcagacat ggacgagcga gaagaattcc tcaatggcgt
 361 ccaagccgta catcggcaca ctgcaagggc cctcgcaagg cgtgttcggc gagaagttcg
 421 agtccacgga tgccgcggac accaccgatc tgaagaccgg cctgctgacg ttcgacctga
 481 gcgcctacga ccatgccccc gattccgcaa cgttcgagat gacgtacctc ggctaccgcg
 541 gcaacccgac ggccaccgac accgacacca tcaaggtgac ccccgtcgac accaccgtgt
 601 gcaccaataa cgccacagac tgcggcgcga atgtcgcgac cggcgcgacc aagccgaagt
 661 tcagcatcaa cgactcctca ttcgtcgccg agtccaagcc gttcgagtac ggtacgacgg
 721 tttacacggg cgacgccatc accgtggttc ccgccaatac caagaaggtc accgtagatg
 781 tgaccgaaat cgtgcgccag cagttcgccg aaggcaagaa ggtcatcacc ctggccgtgg
 841 gcgagaccaa gaagaccgag gttcgtttcg ccagttccga aggcacgacg tccctgaacg
 901 gcgcgaccga agacatggct ccgaagctga ccgtttccgt gtccaccaag gacgatctca
 961 agccctccgc cgacaccacg ttgcaggcat gggccagcga agaacgag aagaagaaca
1021 ctgcggccta tgtcggcgcg ctgcagccgg aaggcgatta cggcgacttc ggtgagaagt
1081 tcaagtccac cgacgtccac gatgtcacag acgccaagat gggtctgatg acgttcgacc
1141 tgtccgatta caccgcggcg cccgagcact ccatcctcac cttgacgtat ctgggctacg
1201 ccggtgcaga caagaccgcc acggccaccg ataaggtcaa ggtggtcgct gttgacacgt
1261 cgcggtgcac cggcaccgct ccctgcgaca ccaacaatgc cacgtgggcg aaccgcccgg
1321 acttcgaggt gaccgatacc acgaagaccg cgacgtccca tgcgttcgct tatggatcta
1381 agaagtattc cgatggcatg accgtcgaat cgggcaacgc caagaaggtc ctgctcgacg
1441 tgtccgatgt catcaaggca gagttcgcca agttcagcgc cggcgccacc gagaagaaga
1501 tcacgctggc cctgggcgag ctcaacaagt ccgacatgcg tttcggcagc aaggaagtca
1561 cctcgctgac cggcgccacc gaagccatgc agccgacctt gtccgtcacc aagaagccga
1621 aggcatacac gctgagcatc gaaggcccga ccaaggtcaa gtaccagaag ggcgaggcgt
1681 tcgacaaggc cggactcgtg gtcaaggcca ccagcacggc tgacggcacg gtcaagacgc
1741 tgaccgaagg caacggtgag gataactaca ccatcgacac cagcgctttc gatagtgcca
1801 gcatcggcgt ataccctgtt accgtgaagt acaacaagga ccccgaaatc gccgcttcgt
1861 tcaacgccta tgtcatcgcc agtgtcgagg acggcggaga cggcgacacc agcaaagacg
1921 actggctgtg gtacaagcag cccgcgtcgc agaccgacgc caccgccacc gccggcggca
1981 attacggcaa ccccgacaac aaccgttggc agcagaccac cttgccgttc ggcaacggca
2041 agatcggcgg caccgtctgg ggcgaggtca gccgtgaacg cgtcaccttc aacgaggaga
2101 cgctgtggac cggcggcccc ggatcctcga ccagctacaa cggcggcaac aacgagacca
2161 agggtcagaa cggcgccacg ctgcgcgcgc tcaacaagca gctcgcgaac ggcgccgaga
2221 cggtcaatcc cggcaacctg accggcggcg agaacgcggc cgagcagggc aactacctga
2281 actggggcga catctacctc gactacgggt tcaacgatac gaccgtcacc gaataccgcc
2341 gcgacctgaa cctgagcaag ggcaaggccg acgtcacgtt caagcatgac ggcgtcacct
2401 acacgcgcga atacttcgcg tcgaaccccg acaatgtcat ggtcgcccgc ctcacggcca
```

| VIII. Informal sequence listing |
| --- |
| 2461 gcaaagccgg caagctgaac ttcaacgtca gcatgccgac caacacgaac tactccaaga |
| 2521 ccggcgaaac cacgacggtc aagggtgaca cgctcaccgt caagggcgct ctcggcaaca |
| 2581 acggcctgct gtacaactcg cagatcaagg tcgtcctcga caacggtgag ggcacgctct |
| 2641 ccgaaggctc cgacggcgct tcgctgaagg tctccgacgc gaaggcggtc acgctgtaca |
| 2701 tcgccgccgc gacggactac aagcagaagt atccgtccta ccgcaccggc gaaaccgccg |
| 2761 ccgaggtgaa cacccgcgtc gccaaggtcg tgcaggacgc cgccaacaag ggctacaccg |
| 2821 ccgtcaagaa agcgcacatc gacgatcatt ccgccatcta cgaccgcgtg aagatcgatt |
| 2881 tgggccagtc cggccacagc tccgacggcg ccgtcgccac cgacgcgctg ctcaaggcgt |
| 2941 accagagagg ctccgcaacc accgcgcaga agcgcgagct ggagacgctg gtgtacaagt |
| 3001 acggccgcta cttgaccatc ggctcctccc gtgagaacag ccagctgccc agcaacctgc |
| 3061 agggcatctg gtcggtcacc gcgggcgaca acgcccacgg caacacgcct tgggctccg |
| 3121 acttccacat gaacgtgaac ctccagatga actactggcc gacctattcg gccaacatgg |
| 3181 gagagctcgc cgagccgctc atcgagtatg tggagggtct ggtcaagccc ggccgtgtga |
| 3241 ccgccaaggt ctacgcgggc gcggagacga cgaaccccga ccacgccg atcggcgagg |
| 3301 gcgagggcta catggcccac accgagaaca ccgcctacgg ctggaccgca cccggtcaat |
| 3361 cgttctcgtg gggttggagc ccggccgccg tgccgtggat cctgcagaac gtgtacgagg |
| 3421 cgtacgagta ctccggcgac cctgccctgc ttgatcgcgt gtacgcgctg ctcaaggagg |
| 3481 aatcgcactt ctacgtcaac tacatgctgc acaaggccgg ctccagctcc ggtgaccgcc |
| 3541 tgactaccgg cgtcgcgtac tcgcccgaac agggcccgct gggcaccgac ggcaacacgt |
| 3601 acgagagctc gctcgtgtgg cagatgctca acgacgccat cgaggcggcc aaggccaagg |
| 3661 gagatccgga cggtctggtc ggcaatacca ccgactgctc ggccgacaac tgggccaaga |
| 3721 atgacagcgc caacttcacc gatgcgaacg ccaaccgttc ctggagctgc gccaagagcc |
| 3781 tgctcaagcc gatcgaggtc ggcgactccg gccagatcaa ggaatggtac ttcgaaggtg |
| 3841 cgctcggcaa gaagaaggat ggatccacca tcagcggcta ccaggcggac aaccagcacc |
| 3901 gtcacatgtc ccacctgctc ggactgttcc ccggtgattt gatcaccatc gacaactccg |
| 3961 agtacatgga tgcggccaag acctcgctga ggtaccgctg cttcaagggc aacgtgctgc |
| 4021 agtccaacac cggctgggcc attggccagc gcatcaattc gtgggctcgc accggcgacg |
| 4081 gcaacaccac gtaccagctg gtcgagctgc agctcaagaa cgcgatgtat gcaaacctgt |
| 4141 tcgattacca tgcgccgttc cagatcgacg gcaacttcgg caacacctcc ggtgtcgacg |
| 4201 aaatgctgct gcagtccaac tccaccttca ccgacaccgc cggcaagaag tacgtgaact |
| 4261 acacgaacat cctgcccgcc ctgcccgatg cctgggcggg cggctcggtg agcggcctcg |
| 4321 tggcccgcgg caacttcacc gtcggcacga catggaagaa cggcaaggcc accgaagtca |
| 4381 ggctgaccct caacaagggc aagcaggcgg ccgtcaagat caccgccggc ggcgcccaga |
| 4441 actacgaggt caagaacggt gacaccgccg tgaacgccaa ggtcgtgacc aacgcggacg |
| 4501 gcgcctcgct gctcgtgttc gataccaccg caggcaccac gtacacgatc acgaagaagg |
| 4561 cgagcgccaa cgtgcccgtc accggcgtga ccgtgaccgg cgccaacacc gccaccgcag |
| 4621 gcgacaccgt cactcttacg gctaccgtcg ccccggccaa tgcgaccgac aagtccgtca |
| 4681 cctggtcgac ctccgacgcc gccgtagcta cggtcaacgc caacgcgtg gtgaccacga |
| 4741 agaaggccgg caaggtgacc atcaccgcca cgtcgaacgg cgacaagacg aagttcggtt |

-continued

| VIII. Informal sequence listing |
|---|

```
4801 ccatcgagat caccgtctcc gccgcgaccg tgcccgtcac cagcgtcacc gttgccggcg 4861 acgccgcgat gaccgtcgat ggagagcaga ccctgacggc gaccgtcgcc ccggccactg 4921 cgaccgacaa gacggtcacg tggaagtcct ccgacgccac tgtggcgacg gttgacgcca 4981 acggcaaggt cgtcgcgaag aaggccggcg aagtgacgat caccgccacg gccggtggcg 5041 tgtccggcac gctgaagatc acggtgagcg acaaggcccc gaccgtcatc ccggtccagt 5101 ccgtgaccgt gacaggcaag caggagctcg tcgaaggcgc ctccacgacc ctgacggcga 5161 ccgtcgcccc ggctgacgcg accgacaaga cggttacgtg gaagtcgagc gacgagtccg 5221 tcgccacggt cgacaaggac ggcgtcgtga ccgccaagaa ggccggcacg gtgaccatca 5281 ccgccacggc cggtggcgtg tccggcacgc tccacatcac cgtgacggcc aagcccgtcg 5341 agaccgtccc cgtcaccagc gtggaggtca ccgtcgaggc cggcaccacc gtctccgtcg 5401 gcaagacact ccaggccacc gcgaccgtca agcccggcaa cgccaccaac aagaaggtga 5461 cgtggaagtc gagcgacgaa tccatcgcga cggtcgacgc caacggcgtc atcaccgcga 5521 agaaggccgg caaggtcgtc atcacggcca cctcgaccga cggcacggac aagtccggca 5581 gcgtcgagat caccgtcgtg gatgagacca gccgacgcc cgaccacaag tccgtcaagg 5641 ccgataccgg cgacgtgacc gccggcaaga ccggtacggt caccgagccg aaggacgtgg 5701 cgggctggaa gagccgctcc atcatcaagc aaggcaagct cggcaaggcc gaaatcgccg 5761 acggcacgct cgtgtatgcg gccggcgaca agaccggtga cgacagcttc gtcgtgcagt 5821 acacgatggc cgacggcacg gtcatcgacg tgacctacag cgtcacggtc aaggccgccg 5881 aaaccggcaa gaacgacggc gacggcaagg gcgacggtgt cgcgaagacc ggcgccgccg 5941 tcggcgcgct cgccggcctc ggcttgatgc tgctcgccgt cggagtgagc gtggtgatga 6001 ttcgccgcaa gcactccgcc tgatccccag tcagaccggc cagtcgtgac cggtcggcct 6061 gactgactct ttctccaccg tccccgtcg gataaacccc ggcggggac ggtggcttgt
```

40

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and database entries cited herein are hereby incorporated by reference in their entireties for all purposes.

What is claimed is:

1. A method for promoting growth of beneficial gut bacteria in an individual having fucosylated oligosaccharides in the gut, comprising administering to the individual a composition comprising the beneficial gut bacteria, wherein the beneficial gut bacteria express a GH-29 family alpha-fucosidase and a GH-95 family alpha-fucosidase, wherein the beneficial gut bacteria are selected from *B. adolescentis, B. catenulatum, B. pseudocatenulatum, B. dentium*, and *B. breve*, thereby promoting growth of beneficial gut bacteria in the individual.

2. The method of claim 1, wherein at least one of the GH-29 family alpha-fucosidase and the GH-95 family alpha-fucosidase is heterologous to the beneficial gut bacteria.

3. The method of claim 1, wherein the beneficial gut bacteria is *B. pseudocatenulatum*.

4. The method of claim 1, wherein the beneficial gut bacteria are *Bifidobacterium breve* (*B. breve*).

5. The method of claim 1, wherein the composition further comprises an oligosaccharide.

6. The method of claim 5, wherein the oligosaccharide is a fucosylated oligosaccharide.

7. The method of claim 5, wherein the oligosaccharide is a milk oligosaccharide.

8. The method of claim 5, wherein the oligosaccharide is a human milk oligosaccharide (HMO).

9. The method of claim 5, wherein the composition does not include an oligosaccharide containing an N-glycolylneuraminic acid residue.

* * * * *

SEQUENCE LISTING

<160> NUMBER OF SEQ ID NOS: 52

<210> SEQ ID NO 1
<211> LENGTH: 449
<212> TYPE: PRT
<213> ORGANISM: Bifidobacterium longum
<220> FEATURE:
<223> OTHER INFORMATION: Bifidobacterium longum subspecies infantis
      (B. infantis) strain ATCC 15697 = JCM 1222 = DSM 20088 alpha-L-
      fucosidase, glycoside hydrolase family 29 (GH29), afcB, Blon_0248

<400> SEQUENCE: 1

Met Val Leu Phe Met Ala Asn Pro Gln Arg Pro Lys Met Tyr Glu Lys
 1               5                  10                  15

Phe Val His Asp Thr Pro Glu Trp Phe Lys Gly Ala Gly Leu Gly Ile
            20                  25                  30

Phe Ala His Trp Gly Ser Tyr Ser Val Pro Ala Trp Ala Glu Pro Ile
        35                  40                  45

-continued

Gly Ala Leu Gly Thr Phe Asp Asp Pro Val Tyr Trp Asn Thr His Cys
 50                  55                  60

Pro Tyr Ala Glu Trp Tyr Trp Asn Thr Met Ser Ile Lys Gly Ser Pro
 65                  70                  75                  80

Ala Ala Glu His Gln Lys Glu Val Tyr Gly Asp Met Pro Tyr Glu Asp
                 85                  90                  95

Phe Ile Asp Met Trp Lys Ala Glu Ala Phe Asp Pro Ala Asp Met Ala
            100                 105                 110

Asp Leu Phe Ala Arg Ala Gly Ala Arg Tyr Phe Val Pro Thr Thr Lys
            115                 120                 125

His His Glu Gly Ile Thr Leu Trp Lys Ala Pro Asp Asn Asp Gly Trp
130                 135                 140

Asn Thr Val Asp Arg Gly Pro His Arg Asp Leu Val Lys Glu Phe Ala
145                 150                 155                 160

Asp Ala Met Arg Asp Lys Gly Leu Lys Phe Gly Val Tyr Tyr Ser Ser
                165                 170                 175

Gly Leu Asp Trp His Lys Glu Pro Asn Met Pro Ile Leu Gly Asp Gly
            180                 185                 190

Glu Tyr Gly Pro Gln Ser Glu Asp Tyr Ala Arg Tyr Met Tyr Ser His
            195                 200                 205

Val Met Asp Leu Ile Asp Glu Tyr Gln Pro Ser Ile Leu Trp Gly Asp
210                 215                 220

Ile Asp Val Pro Lys Ile Ser Glu Glu Asp Asn Asp Phe Ser Val Ala
225                 230                 235                 240

Arg Leu Phe Glu His Tyr Tyr Asp Val Val Pro Asp Gly Val Val Asn
                245                 250                 255

Asp Arg Trp Gly Leu Thr His Trp Asp Phe Arg Thr Val Glu Tyr Glu
            260                 265                 270

Gln Gly Lys Glu Leu Met Gly Lys Gly Met Trp Glu Met Thr Arg Gly
            275                 280                 285

Ile Gly Tyr Ser Phe Gly Tyr Asn Gln Met Glu Asp Ala Asp Ser Tyr
            290                 295                 300

Met Thr Gly Pro Glu Ala Val Lys Leu Leu Ala Asp Val Val Ser Met
305                 310                 315                 320

Gly Gly Asn Leu Leu Leu Asp Ile Gly Pro Asp Ala Ala Gly Arg Ile
                325                 330                 335

Pro Glu Leu Gln Arg Gln Cys Leu Glu Gly Met Ala Asp Trp Met Asp
            340                 345                 350

Val Asn Ser Pro Ser Ile His Asp Val Glu Pro Val Pro Glu Ala Ser
            355                 360                 365

Pro Ser Gly Glu Gly Asp Gly Glu Pro Trp Val Arg Trp Thr Gly Asp
370                 375                 380

Gly Lys Ser Val Tyr Ala Val Val Asp Ala Ala Gly Arg Val Pro Leu
385                 390                 395                 400

Arg Ile Ala Ala Asp Ala Val Asp Ala Asp Ser Ala Val Thr Leu Gly
                405                 410                 415

Gly Ser Ala Val Ala Val Asp Ala Asp Gly Asp Val Leu Thr Ala Asp
            420                 425                 430

Val Pro Ala Ser Glu Val Ala Gly Pro Gln Val Val His Phe Val Arg
            435                 440                 445

Arg

<210> SEQ ID NO 2

```
<211> LENGTH: 449
<212> TYPE: PRT
<213> ORGANISM: Bifidobacterium longum
<220> FEATURE:
<223> OTHER INFORMATION: Bifidobacterium longum subspecies infantis
      (B. infantis) strain ATCC 15697 = JCM 1222 = DSM 20088 alpha-L-
      fucosidase, glycoside hydrolase family 29 (GH29), afcB, Blon_0426

<400> SEQUENCE: 2

Met Val Leu Phe Met Ala Asn Pro Gln Arg Pro Lys Met Tyr Glu Lys
 1               5                  10                  15

Phe Val His Asp Thr Pro Glu Trp Phe Lys Gly Ala Gly Leu Gly Ile
                20                  25                  30

Phe Ala His Trp Gly Ser Tyr Ser Val Pro Ala Trp Ala Glu Pro Ile
            35                  40                  45

Gly Ala Leu Gly Thr Phe Asp Asp Pro Val Tyr Trp Asn Thr His Cys
        50                  55                  60

Pro Tyr Ala Glu Trp Tyr Trp Asn Thr Met Ser Ile Lys Gly Ser Pro
65                  70                  75                  80

Ala Ala Glu His Gln Lys Glu Val Tyr Gly Asp Met Pro Tyr Glu Asp
                85                  90                  95

Phe Ile Asp Met Trp Lys Ala Glu Ala Phe Pro Ala Asp Met Ala
            100                 105                 110

Asp Leu Phe Ala Arg Ala Gly Ala Arg Tyr Phe Val Pro Thr Thr Lys
            115                 120                 125

His His Glu Gly Ile Thr Leu Trp Lys Ala Pro Asp Asn Asp Gly Trp
        130                 135                 140

Asn Thr Val Asp Arg Gly Pro His Arg Asp Leu Val Lys Glu Phe Ala
145                 150                 155                 160

Asp Ala Met Arg Asp Lys Gly Leu Lys Phe Gly Val Tyr Tyr Ser Ser
                165                 170                 175

Gly Leu Asp Trp His Lys Glu Pro Asn Met Pro Ile Leu Gly Asp Gly
            180                 185                 190

Glu Tyr Gly Pro Gln Ser Glu Asp Tyr Ala Arg Tyr Met Tyr Ser His
        195                 200                 205

Val Met Asp Leu Ile Asp Glu Tyr Gln Pro Ser Ile Leu Trp Gly Asp
    210                 215                 220

Ile Asp Val Pro Lys Ile Ser Glu Glu Asp Asn Asp Phe Ser Val Ala
225                 230                 235                 240

Arg Leu Phe Glu His Tyr Tyr Asp Val Val Pro Asp Gly Val Val Asn
                245                 250                 255

Asp Arg Trp Gly Leu Thr His Trp Asp Phe Arg Thr Val Glu Tyr Glu
            260                 265                 270

Gln Gly Lys Glu Leu Met Gly Lys Gly Met Trp Glu Met Thr Arg Gly
        275                 280                 285

Ile Gly Tyr Ser Phe Gly Tyr Asn Gln Met Glu Asp Ala Asp Ser Tyr
    290                 295                 300

Met Thr Gly Pro Glu Ala Val Lys Leu Leu Ala Asp Val Val Ser Met
305                 310                 315                 320

Gly Gly Asn Leu Leu Leu Asp Ile Gly Pro Asp Ala Ala Gly Arg Ile
                325                 330                 335

Pro Glu Leu Gln Arg Gln Cys Leu Glu Gly Met Ala Asp Trp Met Asp
            340                 345                 350

Val Asn Ser Pro Ser Ile His Asp Val Glu Pro Val Pro Glu Ala Ser
        355                 360                 365
```

```
Pro Ser Gly Glu Gly Asp Gly Glu Pro Trp Val Arg Trp Thr Gly Asp
    370             375             380

Gly Lys Ser Val Tyr Ala Val Asp Ala Ala Gly Arg Val Pro Leu
385             390             395             400

Arg Ile Asp Ala Gly Ala Val Asp Val Asp Ser Ala Thr Ile Leu Gly
                405             410             415

Gly Gly Asn Val Val Glu Ala Asp Gly Asp Met Leu Thr Val Glu
            420             425             430

Ile Pro Ala Thr Asp Val Ala Gly Pro Gln Val Val Arg Phe Ala Arg
            435             440             445

His
```

<210> SEQ ID NO 3
<211> LENGTH: 449
<212> TYPE: PRT
<213> ORGANISM: Bifidobacterium breve
<220> FEATURE:
<223> OTHER INFORMATION: Bifidobacterium breve strain SC95 glycoside
      hydrolase family 29 (GH29), afcB

<400> SEQUENCE: 3

```
Met Val Leu Phe Met Ala Asn Pro Gln Arg Pro Lys Met Tyr Glu Lys
1               5                   10                  15

Phe Val His Asp Thr Pro Glu Trp Phe Lys Gly Ala Gly Leu Gly Ile
                20                  25                  30

Phe Ala His Trp Gly Ser Tyr Ser Val Pro Ala Trp Ala Glu Pro Ile
            35                  40                  45

Gly Ala Leu Gly Thr Phe Asp Asp Pro Val Tyr Trp Asn Thr His Cys
50                  55                  60

Pro Tyr Ala Glu Trp Tyr Trp Asn Thr Met Ser Ile Lys Gly Ser Pro
65                  70                  75                  80

Ala Ala Glu His Gln Lys Glu Val Tyr Gly Asp Met Pro Tyr Glu Asp
                85                  90                  95

Phe Ile Asp Met Trp Lys Ala Glu Ala Phe Asp Pro Ala Asp Met Ala
            100                 105                 110

Asp Leu Phe Ala Arg Ala Gly Ala Arg Tyr Phe Val Pro Thr Thr Lys
        115                 120                 125

His His Glu Gly Ile Thr Leu Trp Lys Ala Pro Asp Asn Asp Gly Trp
130                 135                 140

Asn Thr Val Asp Arg Gly Pro His Arg Asp Leu Val Lys Glu Phe Ala
145                 150                 155                 160

Asp Ala Met Arg Asp Lys Gly Leu Lys Phe Gly Val Tyr Tyr Ser Ser
                165                 170                 175

Gly Leu Asp Trp His Lys Glu Pro Asn Met Pro Ile Leu Gly Asp Gly
            180                 185                 190

Glu Tyr Gly Pro Gln Ser Glu Asp Tyr Ala Arg Tyr Met Tyr Ser His
        195                 200                 205

Val Met Asp Leu Ile Asp Lys Tyr Gln Pro Ser Ile Leu Trp Gly Asp
210                 215                 220

Ile Asp Val Pro Lys Ile Ser Glu Glu Asp Asn Asp Phe Ser Val Ala
225                 230                 235                 240

Arg Leu Phe Glu His Tyr Tyr Asp Val Val Pro Asp Gly Val Val Asn
                245                 250                 255

Asp Arg Trp Gly Leu Thr His Trp Asp Phe Arg Thr Val Glu Tyr Glu
            260                 265                 270
```

```
Gln Gly Lys Glu Leu Met Gly Lys Gly Met Trp Glu Met Thr Arg Gly
            275                 280                 285

Ile Gly Tyr Ser Phe Gly Tyr Asn Gln Met Glu Asp Ala Asp Ser Tyr
        290                 295                 300

Met Thr Gly Pro Glu Ala Val Lys Leu Leu Ala Asp Val Val Ser Met
305                 310                 315                 320

Gly Gly Asn Leu Leu Leu Asp Ile Gly Pro Asp Ala Ala Gly Arg Ile
                325                 330                 335

Pro Glu Leu Gln Arg Gln Cys Leu Glu Gly Met Ala Asp Trp Met Tyr
            340                 345                 350

Val Asn Ser Pro Ser Ile His Asp Val Glu Pro Val Pro Glu Ala Ser
        355                 360                 365

Pro Ser Gly Glu Gly Asp Gly Glu Pro Trp Val Arg Trp Thr Gly Asp
370                 375                 380

Gly Lys Ser Val Tyr Ala Val Val Asp Ala Ala Gly Arg Val Pro Leu
385                 390                 395                 400

Arg Ile Ala Ala Asp Ala Val Asp Ala Asp Ser Ala Val Thr Leu Gly
                405                 410                 415

Gly Ser Ala Val Ala Val Asp Ala Asp Gly Asp Val Leu Thr Ala Asp
            420                 425                 430

Val Pro Ala Ser Glu Val Ala Gly Pro Gln Val Val His Phe Val Arg
        435                 440                 445

Arg
```

<210> SEQ ID NO 4
<211> LENGTH: 1493
<212> TYPE: PRT
<213> ORGANISM: Bifidobacterium bifidum
<220> FEATURE:
<223> OTHER INFORMATION: Bifidobacterium bifidum strain JCM 1254 alpha-
      L-fucosidase, glycoside hydrolase family 29 (GH29), afcB

<400> SEQUENCE: 4

```
Met Leu His Thr Ala Ser Arg Gly Cys Ser Arg Ser Trp Leu Arg Arg
1               5                   10                  15

Leu Thr Ala Leu Ile Ala Val Ser Ala Leu Ala Phe Val Ala Leu Pro
            20                  25                  30

Asn Val Ala Val Ala Ala Asp Pro Met Glu Tyr Leu Asp Val Ser Phe
        35                  40                  45

Gly Gly Thr Phe Ala Ala Asp Thr Tyr Thr Thr Gly Gly Asp Glu Val
    50                  55                  60

Ala Lys Gly Pro Val Thr Lys His Gly Ser Ile Pro Thr Lys Leu Asp
65                  70                  75                  80

Gly Gly Gly Ile Thr Leu Ala Gly Gly Thr Asn Gly Val Thr Phe Thr
                85                  90                  95

Ser Thr Ala Ser Phe Ser Glu Ser Gly Lys Val Asn Lys Gly Phe Arg
            100                 105                 110

Ala Glu Met Glu Tyr Arg Thr Thr Gln Thr Pro Ser Asn Leu Ala Thr
        115                 120                 125

Leu Phe Ser Ala Met Gly Asn Ile Phe Val Arg Ala Asn Gly Ser Asn
    130                 135                 140

Leu Glu Tyr Gly Phe Ser Thr Asn Pro Ser Gly Ser Thr Trp Asn Asp
145                 150                 155                 160

Tyr Thr Lys Ser Val Thr Leu Pro Ser Asn Asn Val Lys His Ile Ile
                165                 170                 175
```

-continued

```
Gln Leu Thr Tyr Leu Pro Gly Ala Asp Gly Ala Ala Ser Thr Leu Gln
                180                 185                 190

Leu Ser Val Asp Gly Val Ala Gly Glu Thr Ala Thr Ser Ala Ala Gly
            195                 200                 205

Glu Leu Ala Ala Val Ser Asp Ser Val Gly Asn Lys Phe Gly Ile Gly
        210                 215                 220

Tyr Glu Val Asn Pro Ala Ser Gly Ala Ala Ser Arg Gly Leu Ala Gly
225                 230                 235                 240

Asp Val Phe Arg Ala Arg Val Ala Asp Ser Ala Pro Trp Glu Ile
                245                 250                 255

Leu Asp Ala Ser Gln Leu Leu His Val Asn Phe Asn Gly Thr Phe Ser
                260                 265                 270

Gly Thr Ser Tyr Thr Ala Ala Ser Gly Glu Gln Met Leu Gly Ser Leu
            275                 280                 285

Val Ser Arg Ser Ala Asn Pro Ser Ile Ser Asn Ser Ala Val Thr Leu
        290                 295                 300

Gly Gly Gly Thr Ala Gly Phe Asp Phe Thr Pro Thr Asp Phe Thr Leu
305                 310                 315                 320

Gly Asp Asn Glu Ala Ile Thr Arg Pro Leu Val Ala Glu Leu Arg Phe
                325                 330                 335

Thr Pro Thr Gln Thr Gly Asp Asn Gln Thr Leu Phe Gly Ala Gly Gly
                340                 345                 350

Asn Leu Phe Leu Arg Tyr Glu Ser Asn Lys Leu Val Phe Gly Ala Ser
            355                 360                 365

Thr Lys Ser Gly Asp Asn Trp Thr Asp His Lys Ile Glu Ser Ala Ala
        370                 375                 380

Ala Thr Gly Ala Glu His Val Val Ser Val Ala Tyr Val Pro Asn Lys
385                 390                 395                 400

Ala Gly Thr Gly Ala Lys Leu Val Met Arg Val Asp Gly Gly Asp Ala
                405                 410                 415

Gln Thr Lys Asp Ile Thr Gly Leu Ala Tyr Leu Asn Ser Ser Ile Lys
                420                 425                 430

Gly Lys Val Gly Phe Gly Asn Asp Val His Thr Asp Ala Leu Ser Arg
            435                 440                 445

Gly Phe Val Gly Ser Leu Ser Glu Ile Arg Leu Ala Glu Thr Ser Ala
450                 455                 460

Asn Phe Thr Thr Asn Glu Phe Lys Leu Val Tyr Ser Gln Val Ser Cys
465                 470                 475                 480

Asp Thr Ser Gly Ile Lys Glu Ala Asn Thr Phe Asp Val Glu Pro Ala
                485                 490                 495

Glu Cys Glu Ala Ala Leu Lys Thr Lys Leu Ser Lys Leu Arg Pro Thr
                500                 505                 510

Glu Gly Gln Ala Asp Tyr Ile Asp Trp Gly Gln Ile Gly Phe Leu His
            515                 520                 525

Tyr Gly Ile Asn Thr Tyr Tyr Asn Gln Glu Trp Gly His Gly Asn Glu
        530                 535                 540

Asp Pro Ser Arg Ile Asn Pro Thr Gly Leu Asp Thr Asp Gln Trp Ala
545                 550                 555                 560

Lys Ser Phe Ala Asp Gly Phe Lys Met Ile Met Val Thr Val Lys
                565                 570                 575

His His Asp Gly Phe Glu Leu Tyr Asp Ser Arg Tyr Asn Thr Glu His
                580                 585                 590

Asp Trp Ala Asn Thr Ala Val Ala Lys Arg Thr Gly Glu Lys Asp Leu
```

-continued

```
            595                 600                 605
Phe Arg Lys Ile Val Ala Ser Ala Lys Lys Tyr Gly Leu Lys Val Gly
610                 615                 620

Ile Tyr Tyr Ser Pro Ala Asp Ser Tyr Met Glu Arg Lys Gly Val Trp
625                 630                 635                 640

Gly Asn Asn Ser Ala Arg Val Glu Arg Thr Ile Pro Thr Leu Val Glu
                645                 650                 655

Asn Asp Asp Arg Ala Gly Lys Val Ala Ser Gly Lys Leu Pro Thr Phe
                660                 665                 670

Lys Tyr Lys Ala Thr Asp Tyr Ala Tyr Met Leu Asn Gln Leu Tyr
                675                 680                 685

Glu Leu Leu Thr Glu Tyr Gly Asp Ile Ser Glu Val Trp Phe Asp Gly
690                 695                 700

Ala Gln Gly Asn Thr Ala Gly Thr Glu His Tyr Asp Tyr Gly Val Phe
705                 710                 715                 720

Tyr Glu Met Ile Arg Arg Leu Gln Pro Gln Ala Ile Gln Ala Asn Ala
                725                 730                 735

Ala Tyr Asp Ala Arg Trp Val Gly Asn Glu Asp Gly Trp Ala Arg Gln
                740                 745                 750

Thr Glu Trp Ser Pro Gln Ala Ala Tyr Asn Asp Gly Val Asp Lys Val
                755                 760                 765

Ser Leu Lys Pro Gly Gln Met Ala Pro Asp Gly Lys Leu Gly Ser Met
770                 775                 780

Ser Ser Val Leu Ser Glu Ile Arg Ser Gly Ala Ala Asn Gln Leu His
785                 790                 795                 800

Trp Tyr Pro Ala Glu Val Asp Ala Lys Asn Arg Pro Gly Trp Phe Tyr
                805                 810                 815

Arg Ala Ser Gln Ser Pro Ala Ser Val Ala Glu Val Val Lys Tyr Tyr
                820                 825                 830

Glu Gln Ser Thr Gly Arg Asn Ser Gln Tyr Leu Leu Asn Val Pro Pro
                835                 840                 845

Ser Asp Thr Gly Lys Leu Ala Asp Ala Asp Ala Gly Leu Lys Gly
850                 855                 860

Leu Gly Glu Glu Leu Ala Arg Arg Tyr Gly Thr Asp Leu Ala Leu Gly
865                 870                 875                 880

Lys Ser Ala Thr Val Ala Ala Ser Ala Asn Asp Thr Ala Val Ala Ala
                885                 890                 895

Pro Lys Leu Thr Asp Gly Ser Lys Leu Ser Ser Asp Lys Ala Val Gly
                900                 905                 910

Asn Thr Pro Thr Tyr Thr Ile Asp Leu Gly Ser Thr Val Ala Val Asp
                915                 920                 925

Ala Val Lys Ile Ser Glu Asp Val Arg Asn Ala Gly Gln Gln Ile Glu
                930                 935                 940

Ser Ala Thr Leu Gln Gly Arg Val Asn Gly Thr Trp Thr Asn Leu Ala
945                 950                 955                 960

Thr Met Thr Thr Val Gly Gln Gln Arg Asp Leu Arg Phe Thr Ser Gln
                965                 970                 975

Asn Ile Asp Ala Ile Arg Leu Val Val Asn Ser Ser Arg Gly Pro Val
                980                 985                 990

Arg Leu Ser Arg Leu Glu Val Phe His Thr Glu Ser Glu Ile Gln Thr
                995                 1000                1005

Gly Ala Arg Ala Tyr Tyr Ile Asp Pro Thr Ala Gln Thr Ala Gly Asp
                1010                1015                1020
```

```
Gly Phe Thr Lys Asp Lys Pro Met Thr Ser Ile Glu Gln Leu His Asp
1025                1030                1035                1040

Val Thr Val Ala Pro Gly Ser Val Ile Phe Val Lys Ala Gly Thr Glu
                1045                1050                1055

Leu Thr Gly Asp Phe Ala Val Phe Gly Tyr Gly Thr Lys Asp Glu Pro
                1060                1065                1070

Ile Thr Val Thr Thr Tyr Gly Glu Ser Asp Lys Ala Thr Thr Ala Ser
                1075                1080                1085

Phe Asp Gly Met Thr Ala Gly Leu Thr Leu Lys Gln Ala Leu Lys Ala
                1090                1095                1100

Leu Gly Lys Asp Asp Ala Gly Trp Val Val Ala Asp Ser Ala Thr Ala
1105                1110                1115                1120

Pro Ala Ser Arg Val Tyr Val Pro Gln Asp Glu Ile Ser Val His Ala
                1125                1130                1135

Gln Ser Ser Gln Asn Ser Gly Ala Glu Ala Ala Arg Ala Leu Asp Gly
                1140                1145                1150

Asp Ser Ser Thr Ser Trp His Ser Gln Tyr Ser Pro Thr Thr Ala Ser
                1155                1160                1165

Ala Pro His Trp Val Thr Leu Asp Leu Gly Lys Ser Arg Glu Asn Val
                1170                1175                1180

Ala Tyr Phe Asp Tyr Leu Ala Arg Ile Asp Gly Asn Asn Gly Ala
1185                1190                1195                1200

Ala Lys Asp Tyr Glu Val Tyr Val Ser Asp Asp Pro Asn Asp Phe Gly
                1205                1210                1215

Ala Pro Val Ala Ser Gly Thr Leu Lys Asn Val Ala Tyr Thr Gln Arg
                1220                1225                1230

Ile Lys Leu Thr Pro Lys Asn Gly Arg Tyr Val Lys Phe Val Ile Lys
                1235                1240                1245

Thr Asp Tyr Ser Gly Ser Asn Phe Gly Ser Ala Ala Glu Met Asn Val
1250                1255                1260

Glu Leu Leu Pro Thr Ala Val Glu Glu Asp Lys Val Ala Thr Pro Gln
1265                1270                1275                1280

Lys Pro Thr Val Asp Asp Ala Asp Thr Tyr Thr Ile Pro Asp Ile
                1285                1290                1295

Glu Gly Val Val Tyr Lys Val Asp Gly Lys Val Leu Ala Ala Gly Ser
                1300                1305                1310

Val Val Asn Val Gly Asp Glu Asp Val Thr Val Thr Val Thr Ala Glu
                1315                1320                1325

Pro Ala Asp Gly Tyr Arg Phe Pro Asp Gly Val Thr Ser Pro Val Thr
                1330                1335                1340

Tyr Glu Leu Thr Phe Thr Lys Lys Gly Gly Glu Lys Pro Pro Thr Glu
1345                1350                1355                1360

Val Asn Lys Asp Lys Leu His Ala Thr Ile Thr Lys Ala Gln Ala Ile
                1365                1370                1375

Asp Arg Ser Ala Tyr Thr Asp Glu Ser Leu Lys Val Leu Asp Asp Lys
                1380                1385                1390

Leu Ala Ala Ala Leu Lys Val Tyr Asp Asp Lys Val Ser Gln Asp
                1395                1400                1405

Asp Val Asp Ala Ala Glu Ala Ala Leu Ser Ala Ala Ile Asp Ala Leu
                1410                1415                1420

Lys Thr Lys Pro Thr Thr Pro Gly Gly Glu Gly Glu Lys Pro Gly Glu
1425                1430                1435                1440
```

Gly Glu Lys Pro Gly Asp Gly Asn Lys Pro Gly Asp Gly Lys Lys Pro
            1445                1450                1455

Gly Asp Val Ile Ala Lys Thr Gly Ala Ser Thr Met Gly Val Val Phe
        1460                1465                1470

Ala Ala Leu Ala Met Val Ala Gly Ala Val Val Thr Leu Glu Ala Lys
    1475                1480                1485

Arg Lys Ser Asn Arg
    1490

<210> SEQ ID NO 5
<211> LENGTH: 782
<212> TYPE: PRT
<213> ORGANISM: Bifidobacterium longum
<220> FEATURE:
<223> OTHER INFORMATION: Bifidobacterium longum subspecies infantis
      (B. infantis) strain ATCC 15697 = JCM 1222 = DSM 20088 glycoside
      hydrolase family 95 (GH95), afcA, hypothetical protein Blon_2335

<400> SEQUENCE: 5

Met Lys Leu Thr Phe Asp Gly Ile Ser Ser His Trp Glu Glu Gly Ile
1               5                   10                  15

Pro Phe Gly Asn Gly Arg Met Gly Ala Val Leu Cys Ser Glu Pro Asp
            20                  25                  30

Ala Asp Val Leu Tyr Leu Asn Asp Asp Thr Leu Trp Ser Gly Tyr Pro
        35                  40                  45

His Ala Glu Thr Ser Pro Leu Thr Pro Glu Ile Val Ala Lys Ala Arg
    50                  55                  60

Gln Ala Ser Ser Arg Gly Asp Tyr Val Ser Ala Thr Arg Ile Ile Gln
65                  70                  75                  80

Asp Ala Thr Gln Arg Glu Lys Asp Glu Gln Ile Tyr Glu Pro Phe Gly
                85                  90                  95

Thr Ala Cys Ile Arg Tyr Ser Ser Glu Ala Gly Glu Arg Lys His Val
            100                 105                 110

Lys Arg Ser Leu Asp Leu Ala Arg Ala Leu Ala Gly Glu Ser Phe Arg
        115                 120                 125

Leu Gly Ala Ala Asp Val His Val Asp Ala Trp Cys Ser Ala Pro Asp
    130                 135                 140

Asp Leu Leu Val Tyr Glu Met Ser Ser Ser Ala Pro Val Asp Ala Ser
145                 150                 155                 160

Val Ser Val Thr Gly Thr Phe Leu Lys Gln Thr Arg Ile Ser Ser Gly
                165                 170                 175

Ser Asp Ser Asp Ala Arg Gln Ala Thr Leu Val Val Met Gly Gln Met
            180                 185                 190

Pro Gly Leu Asn Val Gly Ser Leu Ala His Val Thr Asp Asn Pro Trp
        195                 200                 205

Glu Asp Glu Arg Asp Gly Ile Gly Met Ala Tyr Ala Gly Ala Phe Ser
    210                 215                 220

Leu Thr Val Thr Gly Gly Glu Ile Thr Val Ile Asp Asp Val Leu Gln
225                 230                 235                 240

Cys Ser Gly Val Thr Gly Leu Ser Leu Arg Phe Arg Ser Leu Ser Gly
                245                 250                 255

Phe Lys Gly Ser Ala Glu Gln Pro Glu Arg Asp Met Thr Val Leu Ala
            260                 265                 270

Asp Arg Leu Gly Glu Thr Ile Ala Ala Trp Pro Ser Asp Ser Arg Ala
        275                 280                 285

Met Leu Asp Arg His Val Ala Asp Tyr Arg Arg Phe Phe Asp Arg Val

-continued

```
            290                 295                 300
Gly Val Arg Leu Gly Pro Ala His Asp Asp Glu Val Pro Phe
305                 310                 315                 320

Ala Glu Ile Leu Arg Ser Lys Glu Asp Thr Pro His Arg Leu Glu Thr
                325                 330                 335

Leu Ser Glu Ala Met Phe Asp Phe Gly Arg Tyr Leu Leu Ile Ser Ser
                340                 345                 350

Ser Arg Pro His Thr Gln Pro Ser Asn Leu Gln Gly Ile Trp Asn His
            355                 360                 365

Lys Asp Phe Pro Asn Trp Tyr Ser Ala Tyr Thr Thr Asn Ile Asn Ile
        370                 375                 380

Glu Met Asn Tyr Trp Met Thr Gly Pro Cys Ala Leu Lys Glu Leu Ile
385                 390                 395                 400

Glu Pro Leu Val Ala Met Asn Arg Glu Leu Leu Glu Pro Gly His Asp
                405                 410                 415

Ala Ala Gly Ala Ile Leu Gly Cys Gly Gly Ser Ala Val Phe His Asn
                420                 425                 430

Val Asp Ile Trp Arg Arg Ala Leu Pro Ala Asn Gly Glu Pro Thr Trp
            435                 440                 445

Ala Phe Trp Pro Phe Gly Gln Ala Trp Met Cys Arg Asn Leu Phe Asp
450                 455                 460

Glu Tyr Leu Phe Asn Gln Asp Glu Ser Tyr Leu Ala Ser Ile Trp Pro
465                 470                 475                 480

Ile Met Arg Asp Ser Ala Arg Phe Cys Met Asp Phe Leu Ser Asp Thr
                485                 490                 495

Glu His Gly Leu Ala Pro Ala Pro Ala Thr Ser Pro Glu Asn Tyr Phe
                500                 505                 510

Val Val Asp Gly Glu Thr Ile Ala Val Ala His Thr Ser Glu Asn Thr
            515                 520                 525

Thr Ala Ile Val Arg Asn Leu Leu Asp Asp Leu Ile His Ala Ala Gln
        530                 535                 540

Thr Met Pro Asp Leu Asp Asp Gly Asp Lys Ala Leu Val Arg Glu Ala
545                 550                 555                 560

Glu Ser Thr Arg Ala Lys Leu Ala Ala Val Arg Val Gly Ser Asp Gly
                565                 570                 575

Arg Ile Leu Glu Trp Asn Asp Glu Leu Val Glu Ala Asp Pro His His
                580                 585                 590

Arg His Leu Ser His Leu Tyr Glu Leu His Pro Gly Ala Gly Ile Thr
            595                 600                 605

Ala Asn Thr Pro Arg Leu Glu Glu Ala Ala Arg Lys Ser Leu Glu Val
        610                 615                 620

Arg Gly Asp Asp Gly Ser Gly Trp Ser Ile Val Trp Arg Met Ile Met
625                 630                 635                 640

Trp Ala Arg Leu Arg Asp Ala Glu His Ala Glu Arg Ile Ile Gly Met
                645                 650                 655

Phe Leu Arg Pro Val Glu Ala Asp Ala Glu Thr Asp Leu Leu Gly Gly
                660                 665                 670

Gly Val Tyr Ala Ser Gly Met Cys Ala His Pro Phe Gln Ile Asp
            675                 680                 685

Gly Asn Leu Gly Phe Pro Ala Ala Leu Ala Glu Met Leu Val Gln Ser
        690                 695                 700

His Asp Gly Met Val Arg Ile Leu Pro Ala Leu Pro Glu Asp Trp His
705                 710                 715                 720
```

Glu Gly Ser Phe His Gly Leu Arg Ala Arg Gly Gly Leu Ser Val Asp
            725                 730                 735

Ala Ser Trp Thr Asp Asp Ala Ile Glu Tyr Thr Leu Arg Cys Thr Lys
            740                 745                 750

Pro Ala Thr Ile Thr Leu Ile Val Asp Gly Thr Asp Ala Thr Gln Val
            755                 760                 765

Arg Leu Ser Pro Asp Glu Pro Phe Lys Gly Leu Val Arg Arg
            770                 775                 780

<210> SEQ ID NO 6
<211> LENGTH: 1959
<212> TYPE: PRT
<213> ORGANISM: Bifidobacterium bifidum
<220> FEATURE:
<223> OTHER INFORMATION: Bifidobacterium bifidum strain JCM 1254 alpha-
      fucosidase, glycoside hydrolase family 95 (GH95), afcA

<400> SEQUENCE: 6

Met Lys His Arg Ala Met Ser Ser Arg Leu Met Pro Leu Val Ala Ser
 1               5                  10                  15

Cys Ala Thr Val Gly Met Leu Leu Ala Gly Leu Pro Val Ser Ala Val
            20                  25                  30

Ala Val Gly Thr Thr Arg Ala Ala Ser Asp Ala Ser Ser Ser Thr
        35                  40                  45

Thr Ala Thr Ile Thr Pro Ser Ala Asp Thr Thr Leu Gln Thr Trp Thr
    50                  55                  60

Ser Glu Lys Asn Ser Ser Met Ala Ser Lys Pro Tyr Ile Gly Thr Leu
65                  70                  75                  80

Gln Gly Pro Ser Gln Gly Val Phe Gly Glu Lys Phe Glu Ser Thr Asp
                85                  90                  95

Ala Ala Asp Thr Thr Asp Leu Lys Thr Gly Leu Leu Thr Phe Asp Leu
            100                 105                 110

Ser Ala Tyr Asp His Ala Pro Asp Ser Ala Thr Phe Glu Met Thr Tyr
        115                 120                 125

Leu Gly Tyr Arg Gly Asn Pro Thr Ala Thr Asp Thr Asp Thr Ile Lys
    130                 135                 140

Val Thr Pro Val Asp Thr Thr Val Cys Thr Asn Asn Ala Thr Asp Cys
145                 150                 155                 160

Gly Ala Asn Val Ala Thr Gly Ala Thr Lys Pro Lys Phe Ser Ile Asn
                165                 170                 175

Asp Ser Ser Phe Val Ala Glu Ser Lys Pro Phe Glu Tyr Gly Thr Thr
            180                 185                 190

Val Tyr Thr Gly Asp Ala Ile Thr Val Pro Ala Asn Thr Lys Lys
        195                 200                 205

Val Thr Val Asp Val Thr Glu Ile Val Arg Gln Gln Phe Ala Glu Gly
    210                 215                 220

Lys Lys Val Ile Thr Leu Ala Val Gly Glu Thr Lys Lys Thr Glu Val
225                 230                 235                 240

Arg Phe Ala Ser Ser Glu Gly Thr Thr Ser Leu Asn Gly Ala Thr Ala
                245                 250                 255

Asp Met Ala Pro Lys Leu Thr Val Ser Val Ser Thr Lys Asp Asp Leu
            260                 265                 270

Lys Pro Ser Ala Asp Thr Thr Leu Gln Ala Trp Ala Ser Glu Lys Asn
        275                 280                 285

Glu Lys Lys Asn Thr Ala Ala Tyr Val Gly Ala Leu Gln Pro Glu Gly

-continued

```
            290                 295                 300
Asp Tyr Gly Asp Phe Gly Glu Lys Phe Lys Ser Thr Asp Val His Asp
305                 310                 315                 320

Val Thr Asp Ala Lys Met Gly Leu Met Thr Phe Asp Leu Ser Asp Tyr
                325                 330                 335

Thr Ala Ala Pro Glu His Ser Ile Leu Thr Leu Thr Tyr Leu Gly Tyr
                340                 345                 350

Ala Gly Ala Asp Lys Thr Ala Thr Ala Asp Lys Val Lys Val Val
                355                 360                 365

Ala Val Asp Thr Ser Arg Cys Thr Gly Thr Ala Pro Cys Asp Thr Asn
370                 375                 380

Asn Ala Thr Trp Ala Asn Arg Pro Asp Phe Glu Val Thr Asp Thr Thr
385                 390                 395                 400

Lys Thr Ala Thr Ser His Ala Phe Ala Tyr Gly Ser Lys Tyr Ser
                405                 410                 415

Asp Gly Met Thr Val Glu Ser Gly Asn Ala Lys Lys Val Leu Leu Asp
                420                 425                 430

Val Ser Asp Val Ile Lys Ala Glu Phe Ala Lys Phe Ser Ala Gly Ala
        435                 440                 445

Thr Glu Lys Lys Ile Thr Leu Ala Leu Gly Glu Leu Asn Lys Ser Asp
        450                 455                 460

Met Arg Phe Gly Ser Lys Glu Val Thr Ser Leu Thr Gly Ala Thr Glu
465                 470                 475                 480

Ala Met Gln Pro Thr Leu Ser Val Thr Lys Lys Pro Lys Ala Tyr Thr
                485                 490                 495

Leu Ser Ile Glu Gly Pro Thr Lys Val Lys Tyr Gln Lys Gly Glu Ala
                500                 505                 510

Phe Asp Lys Ala Gly Leu Val Val Lys Ala Thr Ser Thr Ala Asp Gly
        515                 520                 525

Thr Val Lys Thr Leu Thr Glu Gly Asn Gly Glu Asp Asn Tyr Thr Ile
530                 535                 540

Asp Thr Ser Ala Phe Asp Ser Ala Ser Ile Gly Val Tyr Pro Val Thr
545                 550                 555                 560

Val Lys Tyr Asn Lys Asp Pro Glu Ile Ala Ala Ser Phe Asn Ala Tyr
                565                 570                 575

Val Ile Ala Ser Val Glu Asp Gly Gly Asp Gly Asp Thr Ser Lys Asp
                580                 585                 590

Asp Trp Leu Trp Tyr Lys Gln Pro Ala Ser Gln Thr Asp Ala Thr Ala
        595                 600                 605

Thr Ala Gly Gly Asn Tyr Gly Asn Pro Asp Asn Asn Arg Trp Gln Gln
        610                 615                 620

Thr Thr Leu Pro Phe Gly Asn Gly Lys Ile Gly Gly Thr Val Trp Gly
625                 630                 635                 640

Glu Val Ser Arg Glu Arg Val Thr Phe Asn Glu Glu Thr Leu Trp Thr
                645                 650                 655

Gly Gly Pro Gly Ser Ser Thr Ser Tyr Asn Gly Gly Asn Asn Glu Thr
                660                 665                 670

Lys Gly Gln Asn Gly Ala Thr Leu Arg Ala Leu Asn Lys Gln Leu Ala
        675                 680                 685

Asn Gly Ala Glu Thr Val Asn Pro Gly Asn Leu Thr Gly Gly Glu Asn
        690                 695                 700

Ala Ala Glu Gln Gly Asn Tyr Leu Asn Trp Gly Asp Ile Tyr Leu Asp
705                 710                 715                 720
```

```
Tyr Gly Phe Asn Asp Thr Thr Val Thr Glu Tyr Arg Arg Asp Leu Asn
            725                 730                 735

Leu Ser Lys Gly Lys Ala Asp Val Thr Phe Lys His Asp Gly Val Thr
        740                 745                 750

Tyr Thr Arg Glu Tyr Phe Ala Ser Asn Pro Asp Asn Val Met Val Ala
            755                 760                 765

Arg Leu Thr Ala Ser Lys Ala Gly Lys Leu Asn Phe Asn Val Ser Met
    770                 775                 780

Pro Thr Asn Thr Asn Tyr Ser Lys Thr Gly Glu Thr Thr Val Lys
785                 790                 795                 800

Gly Asp Thr Leu Thr Val Lys Gly Ala Leu Gly Asn Asn Gly Leu Leu
            805                 810                 815

Tyr Asn Ser Gln Ile Lys Val Val Leu Asp Asn Gly Glu Gly Thr Leu
            820                 825                 830

Ser Glu Gly Ser Asp Gly Ala Ser Leu Lys Val Ser Asp Ala Lys Ala
            835                 840                 845

Val Thr Leu Tyr Ile Ala Ala Thr Asp Tyr Lys Gln Lys Tyr Pro
    850                 855                 860

Ser Tyr Arg Thr Gly Glu Thr Ala Ala Glu Val Asn Thr Arg Val Ala
865                 870                 875                 880

Lys Val Val Gln Asp Ala Ala Asn Lys Gly Tyr Thr Ala Val Lys Lys
            885                 890                 895

Ala His Ile Asp Asp His Ser Ala Ile Tyr Asp Arg Val Lys Ile Asp
            900                 905                 910

Leu Gly Gln Ser Gly His Ser Ser Asp Gly Ala Val Ala Thr Asp Ala
            915                 920                 925

Leu Leu Lys Ala Tyr Gln Arg Gly Ser Ala Thr Thr Ala Gln Lys Arg
    930                 935                 940

Glu Leu Glu Thr Leu Val Tyr Lys Tyr Gly Arg Tyr Leu Thr Ile Gly
945                 950                 955                 960

Ser Ser Arg Glu Asn Ser Gln Leu Pro Ser Asn Leu Gln Gly Ile Trp
            965                 970                 975

Ser Val Thr Ala Gly Asp Asn Ala His Gly Asn Thr Pro Trp Gly Ser
            980                 985                 990

Asp Phe His Met Asn Val Asn Leu Gln Met Asn Tyr Trp Pro Thr Tyr
            995                 1000                1005

Ser Ala Asn Met Gly Glu Leu Ala Glu Pro Leu Ile Glu Tyr Val Glu
    1010                1015                1020

Gly Leu Val Lys Pro Gly Arg Val Thr Ala Lys Val Tyr Ala Gly Ala
1025                1030                1035                1040

Glu Thr Thr Asn Pro Glu Thr Thr Pro Ile Gly Glu Gly Glu Gly Tyr
            1045                1050                1055

Met Ala His Thr Glu Asn Thr Ala Tyr Gly Trp Thr Ala Pro Gly Gln
            1060                1065                1070

Ser Phe Ser Trp Gly Trp Ser Pro Ala Ala Val Pro Trp Ile Leu Gln
        1075                1080                1085

Asn Val Tyr Glu Ala Tyr Glu Tyr Ser Gly Asp Pro Ala Leu Leu Asp
    1090                1095                1100

Arg Val Tyr Ala Leu Leu Lys Glu Glu Ser His Phe Tyr Val Asn Tyr
1105                1110                1115                1120

Met Leu His Lys Ala Gly Ser Ser Gly Asp Arg Leu Thr Thr Gly
            1125                1130                1135
```

-continued

Val Ala Tyr Ser Pro Glu Gln Gly Pro Leu Gly Thr Asp Gly Asn Thr
            1140                1145                1150

Tyr Glu Ser Ser Leu Val Trp Gln Met Leu Asn Asp Ala Ile Glu Ala
        1155                1160                1165

Ala Lys Ala Lys Gly Asp Pro Asp Gly Leu Val Gly Asn Thr Thr Asp
    1170                1175                1180

Cys Ser Ala Asp Asn Trp Ala Lys Asn Asp Ser Gly Asn Phe Thr Asp
1185                1190                1195                1200

Ala Asn Ala Asn Arg Ser Trp Ser Cys Ala Lys Ser Leu Leu Lys Pro
                1205                1210                1215

Ile Glu Val Gly Asp Ser Gly Gln Ile Lys Glu Trp Tyr Phe Glu Gly
            1220                1225                1230

Ala Leu Gly Lys Lys Lys Asp Gly Ser Thr Ile Ser Gly Tyr Gln Ala
        1235                1240                1245

Asp Asn Gln His Arg His Met Ser His Leu Leu Gly Leu Phe Pro Gly
    1250                1255                1260

Asp Leu Ile Thr Ile Asp Asn Ser Glu Tyr Met Asp Ala Ala Lys Thr
1265                1270                1275                1280

Ser Leu Arg Tyr Arg Cys Phe Lys Gly Asn Val Leu Gln Ser Asn Thr
                1285                1290                1295

Gly Trp Ala Ile Gly Gln Arg Ile Asn Ser Trp Ala Arg Thr Gly Asp
            1300                1305                1310

Gly Asn Thr Thr Tyr Gln Leu Val Glu Leu Gln Leu Lys Asn Ala Met
        1315                1320                1325

Tyr Ala Asn Leu Phe Asp Tyr His Ala Pro Phe Gln Ile Asp Gly Asn
    1330                1335                1340

Phe Gly Asn Thr Ser Gly Val Asp Glu Met Leu Leu Gln Ser Asn Ser
1345                1350                1355                1360

Thr Phe Thr Asp Thr Ala Gly Lys Lys Tyr Val Asn Tyr Thr Asn Ile
                1365                1370                1375

Leu Pro Ala Leu Pro Asp Ala Trp Ala Gly Gly Ser Val Ser Gly Leu
            1380                1385                1390

Val Ala Arg Gly Asn Phe Thr Val Gly Thr Thr Trp Lys Asn Gly Lys
        1395                1400                1405

Ala Thr Glu Val Arg Leu Thr Ser Asn Lys Gly Lys Gln Ala Ala Val
    1410                1415                1420

Lys Ile Thr Ala Gly Gly Ala Gln Asn Tyr Glu Val Lys Asn Gly Asp
1425                1430                1435                1440

Thr Ala Val Asn Ala Lys Val Val Thr Asn Ala Asp Gly Ala Ser Leu
                1445                1450                1455

Leu Val Phe Asp Thr Thr Ala Gly Thr Thr Tyr Thr Ile Thr Lys Lys
            1460                1465                1470

Ala Ser Ala Asn Val Pro Val Thr Gly Val Thr Val Thr Gly Ala Asn
        1475                1480                1485

Thr Ala Thr Ala Gly Asp Thr Val Thr Leu Thr Ala Thr Val Ala Pro
    1490                1495                1500

Ala Asn Ala Thr Asp Lys Ser Val Thr Trp Ser Thr Ser Asp Ala Ala
1505                1510                1515                1520

Val Ala Thr Val Asn Ala Asn Gly Val Val Thr Thr Lys Lys Ala Gly
                1525                1530                1535

Lys Val Thr Ile Thr Ala Thr Ser Asn Gly Asp Lys Thr Lys Phe Gly
            1540                1545                1550

Ser Ile Glu Ile Thr Val Ser Ala Ala Thr Val Pro Val Thr Ser Val

```
                    1555                1560                1565

Thr Val Ala Gly Asp Ala Ala Met Thr Val Asp Gly Glu Gln Thr Leu
    1570                1575                1580

Thr Ala Thr Val Ala Pro Ala Thr Ala Thr Asp Lys Thr Val Thr Trp
1585                1590                1595                1600

Lys Ser Ser Asp Ala Thr Val Ala Thr Val Asp Ala Asn Gly Lys Val
                1605                1610                1615

Val Ala Lys Lys Ala Gly Glu Val Thr Ile Thr Ala Thr Ala Gly Gly
            1620                1625                1630

Val Ser Gly Thr Leu Lys Ile Thr Val Ser Asp Lys Ala Pro Thr Val
        1635                1640                1645

Ile Pro Val Gln Ser Val Thr Val Gly Lys Gln Glu Leu Val Glu
    1650                1655                1660

Gly Ala Ser Thr Thr Leu Thr Ala Thr Val Ala Pro Ala Asp Ala Thr
1665                1670                1675                1680

Asp Lys Thr Val Thr Trp Lys Ser Ser Asp Glu Ser Val Ala Thr Val
                1685                1690                1695

Asp Lys Asp Gly Val Val Thr Ala Lys Lys Ala Gly Thr Val Thr Ile
            1700                1705                1710

Thr Ala Thr Ala Gly Gly Val Ser Gly Thr Leu His Ile Thr Val Thr
        1715                1720                1725

Ala Lys Pro Val Glu Thr Val Pro Val Thr Ser Val Glu Val Thr Val
    1730                1735                1740

Glu Ala Gly Thr Thr Val Ser Val Gly Lys Thr Leu Gln Ala Thr Ala
1745                1750                1755                1760

Thr Val Lys Pro Gly Asn Ala Thr Asn Lys Lys Val Thr Trp Lys Ser
                1765                1770                1775

Ser Asp Glu Ser Ile Ala Thr Val Asp Ala Asn Gly Val Ile Thr Ala
            1780                1785                1790

Lys Lys Ala Gly Lys Val Val Ile Thr Ala Thr Ser Thr Asp Gly Thr
        1795                1800                1805

Asp Lys Ser Gly Ser Val Glu Ile Thr Val Val Asp Glu Thr Lys Pro
    1810                1815                1820

Thr Pro Asp His Lys Ser Val Lys Ala Asp Thr Gly Asp Val Thr Ala
1825                1830                1835                1840

Gly Lys Thr Gly Thr Val Thr Glu Pro Lys Asp Val Ala Gly Trp Lys
                1845                1850                1855

Ser Arg Ser Ile Ile Lys Gln Gly Lys Leu Gly Lys Ala Glu Ile Ala
            1860                1865                1870

Asp Gly Thr Leu Val Tyr Ala Ala Gly Asp Lys Thr Gly Asp Asp Ser
        1875                1880                1885

Phe Val Val Gln Tyr Thr Met Ala Asp Gly Thr Val Ile Asp Val Thr
    1890                1895                1900

Tyr Ser Val Thr Val Lys Ala Ala Glu Thr Gly Lys Asn Asp Gly Asp
1905                1910                1915                1920

Gly Lys Gly Asp Gly Val Ala Lys Thr Gly Ala Ala Val Gly Ala Leu
                1925                1930                1935

Ala Gly Leu Gly Leu Met Leu Leu Ala Val Gly Val Ser Val Val Met
            1940                1945                1950

Ile Arg Arg Lys His Ser Ala
        1955

<210> SEQ ID NO 7
```

```
<211> LENGTH: 1350
<212> TYPE: DNA
<213> ORGANISM: Bifidobacterium longum
<220> FEATURE:
<223> OTHER INFORMATION: Bifidobacterium longum subspecies infantis (B.
      infantis) strain ATCC 15697 = JCM 1222 = DSM 20088 glycoside
      hydrolase family 29 (GH29), afcB, Blon_0248

<400> SEQUENCE: 7
atggtgttgt tcatggccaa tccacagcgt cccaagatgt atgagaagtt cgtgcacgat      60
acacccgaat ggttcaaggg cgccggtctc ggcatcttcg cccactgggg ttcgtattcg     120
gtgccggcat gggcggagcc gatcggtgcg cttggcacct tgacgatcc ggtgtactgg      180 aacacccact gcccgtatgc ggaatggtat tggaacacga tgagcatcaa gggctcgccg     240
gcggccgagc atcagaagga agtctacggt gacatgccgt atgaggactt catcgacatg     300
tggaaggccg aggcgttcga ccccgcggac atggccgacc tgttcgcacg cgccggtgcc     360
cggtacttcg tgccgaccac gaagcatcac gaaggcatca cgctgtggaa ggcccccgac     420
aacgatgggt ggaataccgt ggaccgtggt ccgcatcgcg atctggtcaa ggaattcgcc     480
gacgccatgc gcgacaaggg actgaagttc ggcgtgtact actcctcggg cctcgactgg     540
cacaaggagc ccaacatgcc gattctcggc gacgggaat acgggccgca gagcgaggac      600
tacgcccgct atatgtactc gcatgtgatg gacctcatcg acgaatacca gccgtccatc     660
ctgtggggag atatcgacgt gccgaagatc tcggaggagg acaacgattt cagcgtggcc     720
cgactgttcg agcattacta cgacgtggtg ccggatggtg tggtcaacga ccgctggggc     780
ctgacccatt gggacttccg caccgtcgaa tacgaacagg caaggagct catgggcaag      840 ggcatgtggg agatgacccg aggcatcggc tactccttcg gctacaacca gatggaggac     900
gccgactcct acatgaccgg tccggaggcg gtgaagttgc tcgccgacgt ggtctccatg     960
ggcggcaacc tgctgctcga catcggcccc gacgccgccg gacgcatccc gaactgcag     1020 cgtcagtgcc tcgagggcat ggccgactgg atggacgtga actcgccgag tatccatgat    1080
gtcgaaccgg tgccggaagc ctcgccttcc ggagagggg acggcgagcc atgggtccgt     1140
tggaccggag acggcaagag cgtctatgcc gtcgtcgatg ctgcgggcag ggttccgctg    1200
cgcatcgccg ccgatgctgt ggacgcggat tccgccgtga cgcttggcgg atccgcagtc    1260
gccgtggacg ccgacggcga cgtgctgacc gccgatgttc cggcctcgga agtggcgggg    1320
ccgcaggtcg tgcacttcgt ccgtcgctga                                     1350

<210> SEQ ID NO 8
<211> LENGTH: 1350
<212> TYPE: DNA
<213> ORGANISM: Bifidobacterium longum
<220> FEATURE:
<223> OTHER INFORMATION: Bifidobacterium longum subspecies infantis (B.
      infantis) strain ATCC 15697 = JCM 1222 = DSM 20088 glycoside
      hydrolase family 29 (GH29), afcB, Blon_0426

<400> SEQUENCE: 8
atggtgttgt tcatggccaa tccacagcgt cccaagatgt atgagaagtt cgtgcacgat      60
acacccgaat ggttcaaggg cgccggtctc ggcatcttcg cccactgggg ttcgtattcg     120
gtgccggcat gggcggagcc gatcggtgcg cttggcacct tgacgatcc ggtgtactgg      180 aacacccact gcccgtatgc ggaatggtat tggaacacga tgagcatcaa gggctcgccg     240
gcggccgagc atcagaagga agtctacggt gacatgccgt atgaggactt catcgacatg     300
tggaaggccg aggcgttcga ccccgcggac atggccgacc tgttcgcacg cgccggtgcc     360
```

```
cggtacttcg tgccgaccac gaagcatcac gaaggcatca cgctgtggaa ggcccccgac    420
aacgatgggt ggaataccgt ggaccgtggt ccgcatcgcg atctggtcaa ggaattcgcc    480
gacgccatgc gcgacaaggg actgaagttc ggcgtgtact actcctcggg cctcgactgg    540
cacaaggagc ccaacatgcc gattctcggc gacggggaat acgggccgca gagcgaggac    600
tacgcccgct atatgtactc gcatgtgatg gacctcatcg acgaatacca gccgtccatc    660
ctgtggggag atatcgacgt gccgaagatc tcggaggagg acaacgattt cagcgtggcc    720
cgactgttcg agcattacta cgacgtggtg ccggatggtg tggtcaacga ccgctggggc    780
ctgacccatt gggacttccg caccgtcgaa tacgaacagg gcaaggagct catgggcaag    840
ggcatgtggg agatgacccg aggcatcggc tactccttcg gctacaacca gatggaggac    900
gccgactcct acatgaccgg tccggaggcg gtgaagttgc tcgccgacgt ggtctccatg    960
ggcggcaacc tgctgctcga catcggcccc gacgccgccg gacgcatccc gaactgcag    1020 cgtcagtgcc tcgagggcat ggccgactgg atggacgtga actcgccgag tatccatgat   1080
gtcgaaccgg tgccggaagc ctcgccttcc ggagaggggg acggcgagcc atgggttcgt   1140
tggaccggag acggcaagag cgtctatgcc gtcgtcgatg ctgcgggcag ggttccgctg   1200
cgcatagatg cgggtgcggt cgatgtggat ccgcaaccca ttcttggcgg tggcaacgtt   1260
gtcgtggagg cggacggcga tatgctgacc gtggagattc ccgcgacaga cgtcgccggc   1320
cctcaggtcg tgcgttttgc tcgacactaa                                    1350

<210> SEQ ID NO 9
<211> LENGTH: 1350
<212> TYPE: DNA
<213> ORGANISM: Bifidobacterium breve
<220> FEATURE:
<223> OTHER INFORMATION: Bifidobacterium breve strain SC95 glycoside
      hydrolase family 29 (GH29), afcB

<400> SEQUENCE: 9
atggtgctgt tcatggccaa tccgcagcgt cccaagatgt atgagaagtt cgtgcacgat     60
acacccgaat ggttcaaggg cgccggtctc ggcatcttcg cccactgggg ttcgtattcg    120
gtgccggcat gggcggagcc gatcggtgcg cttggcacct ttgacgatcc ggtgtactgg    180
aacacccact gcccgtatgc ggaatggtat tggaacacga tgagcatcaa gggctcgccg    240
gcggccgagc atcagaagga agtctacggt gacatgccgt atgaggactt catcgacatg    300
tggaaggccg aggcgttcga ccccgcggac atggccgacc tgttcgcacg cgccggtgcc    360
cggtacttcg tgccgaccac gaagcatcac gaaggcatca cgctgtggaa ggcccccgac    420
aacgatgggt ggaataccgt ggaccgtggt ccgcatcgcg atctggtcaa ggaattcgcc    480
gacgccatgc gcgacaaggg actgaagttc ggcgtgtact actcctcggg cctcgactgg    540
cacaaggagc ccaacatgcc gattctcggc gacggggaat acgggccgca gagcgaggac    600
tacgcccgct atatgtactc gcatgtgatg gacctcatcg acaaatacca gccgtccatc    660
ctgtggggag atatcgacgt gccgaagatc tcggaggagg acaacgattt cagtgtggcc    720
cgactgttcg agcattacta tgacgtggtg ccggatggtg tggtcaacga ccgctggggc    780
ctgacccatt gggacttccg caccgtcgaa tacgaacagg gcaaggagct catgggcaag    840
ggcatgtggg agatgacccg aggcatcggc tactccttcg gctacaacca gatggaggac    900
gccgactcct acatgaccgg tccggaggcg gtgaagttgc tcgccgacgt ggtctccatg    960
ggcggcaacc tgctgctcga catcggcccc gacgccgccg gacgcatccc gaactgcag   1020
```

```
cgtcagtgcc tcgagggcat ggccgactgg atgtacgtga actcgccgag tatccatgat   1080
gtcgaaccgg tgccggaagc ctcgccttcc ggagaggggg acggcgagcc atgggtccgt   1140
tggaccggag acggcaagag cgtctatgcc gtcgtcgatg ctgcgggcag ggttccgctg   1200
cgcatcgccg ccgatgctgt ggacgcggat tccgccgtga cgcttggcgg atccgcagtc   1260
gccgtggacg ccgacggcga cgtgctgacc gccgatgttc cggcctcgga agtggcgggg   1320
ccgcaggtcg tgcacttcgt ccgtcgctga                                    1350
```

<210> SEQ ID NO 10
<211> LENGTH: 4482
<212> TYPE: DNA
<213> ORGANISM: Bifidobacterium bifidum
<220> FEATURE:
<223> OTHER INFORMATION: Bifidobacterium bifidum strain JCM 1254 alpha-
      L-fucosidase, glycoside hydrolase family 29 (GH29), afcB

<400> SEQUENCE: 10

```
atgctacaca cagcatcaag aggatgctcg cgttcgtggc tgcgcagact caccgcattg     60
atagcggtct cggcgctcgc gttcgtggca ttgccgaacg tcgcggtggc ggcggatccg    120
atggaatacc tcgatgtgtc gttcggcggc acgttcgctg cagacaccta caccacaggt    180
ggcgacgagg tggcgaaggg ccccgtgacc aagcacggca gcataccgac caagcttgac    240
ggcggcggca tcaccctcgc tggcggcacc aacggcgtga cattcacctc gaccgcgagc    300
ttcagcgaga gtgggaaggt gaacaaggga ttccgcgccg aaatggagta ccgtacgacg    360
cagacgccca gcaacctcgc cacattgttc tccgccatgg gcaacatctt cgtgcgggcg    420
aacggcagca acctcgaata cggcttctcc acgaacccct tccggcagta catggaacgac   480 tacacaaagt ccgtgacgct gccttccaac aatgtgaagc acatcatcca gctgacatat    540
ctgccgggag ccgacggcgc tgcctcgacg ttgcagttgt cggtggatgg cgtggccggc    600
gagaccgcca cctccgcggc cggcgagctc gcggccgtca gcgattccgt cgggaacaag    660
ttcgggatcg gctacgaggt gaaccccgct ccggcgcgg cgagccgcgg tcttgccggt    720
gacgtgttcc gcgcgcgtgt cgccgattcg gacgccccgt gggagattct tgacgcatcc    780
cagctgctgc atgtcaattt caacggcacg ttcagcggca cctcatatac cgcggcgagc    840
ggcgagcaga tgctgggctc gctggtgtcg cgctcggcca atccgtccat ctcgaactcc    900
gccgtcacgc tgggcggcgg cacggccgga ttcgatttca cgcccacgga cttcaccctc    960
ggtgacaacg aggccatcac ccgcccgctg tcgcggagc tgcgcttcac cccgacgcag   1020
accggcgaca accagaccct gttcggcgcg ggcggcaacc tgttcctgcg ctacgagtcg   1080
aacaagctcg tgttcggcgc ctccaccaag tccggcgata ttggaccga ccacaagatc    1140 gagtccgcgg ccgccacggg tgcggagcac gtcgtgtcgg tggcgtacgt gcccaataag   1200
gccggcaccg gcgcgaagct tgtcatgcgc gtggatggcg cgacgcccca gaccaaggac   1260
atcactggtc tggcttacct gaattcgagc atcaagggca aggtcggctt cggcaacgac   1320
gtgcataccg acgcgctcag ccgcggcttc gtcggctcgc tgagcgagat ccgcctggcc   1380
gaaacctccg cgaacttcac caccaacgaa ttcaagctgg tctactctca ggtcagctgc   1440
gacacgtcgg gcatcaagga ggcgaatacc ttcgacgtgg agcccgccga gtgcgaggcc   1500
gcgcttaaga ccaagctgtc caagctgcgt ccgaccgaag ggcaggccga ctacatcgac   1560
tggggtcaga tcggattcct ccattacggc atcaacacgt actacaacca ggagtggggt   1620
cacggtaacg aggatccctc ccgcatcaac ccgaccggcc tcgacaccga ccagtgggcg   1680
```

```
aagtccttcg ccgacggtgg cttcaagatg atcatggtga cggtcaagca ccatgacggt    1740
ttcgagctgt acgactcgcg gtacaacacc gagcacgact gggcaaacac cgccgtcgcc    1800
aagcgcacgg gggagaagga cctgttccgc aagattgtcg cctcggcgaa gaaatacggc    1860
ctgaaggtcg gcatctacta ttcgccggcc gattcctaca tggagaggaa gggcgtctgg    1920
ggcaacaact ccgcacgcgt cgagcgcacg atccccacgc tggtggagaa cgacgaccgc    1980
gccggcaagg tggcttccgg caaactgccc acgttcaagt acaaggccac ggattacggc    2040
gcctacatgc tcaaccagct ctatgagctg ctgactgagt acggcgacat ctccgaggtc    2100
tggttcgacg gtgcccaagg caacaccgca ggcactgagc attacgacta tggcgtgttc    2160
tacgagatga tccgccggct tcagcccag gcaattcagg ccaacgccgc atacgatgcc    2220
cgatgggtgg gcaacgagga cggctgggcc cgtcagaccg agtggagccc gcaggcggca    2280
tacaacgacg gcgtggacaa ggtgtcgctc aagcctggcc agatggcccc cgacggtaag    2340
cttggcagca tgtcgagcgt gctgtccgag atccgcagcg gcgccgccaa ccagctgcac    2400
tggtatccgg ccgaagtcga cgccaagaac cggcccggat ggttctaccg tgccagccaa    2460
tcgccggcgt ccgtagccga agtcgtgaag tactacgagc agtccacggg acgcaactcg    2520
cagtatctgc tgaacgtccc accgtccgat accggcaagc tcgccgatgc ggatgccgcg    2580
ggacttaagg ggctgggcga ggagctcgcc cgacgctacg gcaccgatct tgccctgggc    2640
aagagcgcga ccgtcgccgc gtccgcgaac gacactgcgg tagcggcccc gaagctgacc    2700
gacggttcga agctctcctc cgacaaggcc gtgggcaata cgccgacgta caccatcgat    2760
ctgggcagca ctgtcgccgt ggatgcagtg aagatctccg aggacgtgcg caatgccggc    2820
cagcagatcg aaagcgccac tctgcaggga cgagtcaatg gaacatggac gaatctggcg    2880
actatgacga cggtcgggca gcagcgcgac cttcgcttca cgtcccagaa catcgatgcc    2940
atccgtctgg tggtcaactc ctcccgcggt ccggtgcgtc tgagccgtct tgaggtgttc    3000
cacaccgaat ccgagattca gaccggcgcc cgcgcctact acatcgatcc gacggcgcag    3060
accgcgggag atggattcac gaaggacaag cccatgacgt cgatcgagca gctgcacgat    3120
gtgaccgtcg cgccaggctc cgtgatcttc gtcaaggcgg gcaccgagct gaccggggac    3180
ttcgccgtct tcggctacgg caccaaggac gagcccatca ccgtgacgac atacggcgaa    3240
agcgacaaag ccaccaccgc gagcttcgac ggcatgaccg ccgggctgac gctgaagcag    3300
gcgctgaagg cgctcggcaa ggacgacgcc ggctgggtcg tggccgattc cgccactgca    3360
ccggcctccc gcgtgtatgt cccgcaggat gagatcagcg tgcacgccca gtcgtcgcag    3420
aactccggcg cagaggcggc gagggcgctc gacggcgact cgtcgacgag ctggcactcc    3480
cagtacagcc cgaccaccgc gtctgctccg cattgggtga ctctcgatct cggcaaatcg    3540
cgtgagaacg tcgcctactt cgactacctc gcccgtatcg acggcaacaa taacggtgcc    3600
gccaaggatt acgaggtgta tgtctccgac gatcccaacg attttggagc ccctgtggcc    3660
tcgggcacgt tgaagaacgt cgcctacacg cagcgcatca agctgacccc caagaacgga    3720
cggtacgtca agttcgtcat caagaccgat tattccggat cgaacttcgg ctccgcggcg    3780
gaaatgaatg tcgagttgct gcccacggcc gtagaggagg acaaggtcgc caccccgcag    3840
aagccgacag tggacgatga tgccgataca tacaccatcc ccgacatcga gggagtcgtg    3900
tacaaggtcg acggcaaggt gttggccgct ggttccgtag tgaacgtggg cgatgaggac    3960
gtgaccgtca cggtcaccgc cgagcccgcc gacggatacc gcttcccgga tggtgtgacg    4020
```

-continued

```
tccccagtca cgtatgagct gacgttcacc aagaagggtg gcgagaagcc tccgaccgaa    4080
gtcaacaagg acaagctgca cgccacgatc accaaggctc aggcgatcga ccgttccgcc    4140
tatacggacg agtcgctcaa ggtgcttgat gacaagctcg ccgcagcgct caaggtctat    4200
gacgatgaca aggtgagcca ggatgatgtc gatgccgccg aggcggctct gtctgcggcg    4260
atcgacgcgc tgaagaccaa gccgacgacc cccggcggtg aaggtgagaa gcctggtgaa    4320
ggtgaaaagc ccggtgacgg caacaagccc ggtgacggca agaagcccgg cgacgtgatc    4380
gcaaagaccg gcgcctccac aatgggcgtt gtcttcgctg cactcgcgat ggtagcgggt    4440
gcggtcgtga cgcttgaagc caagcgtaag tccaaccggt aa                       4482
```

<210> SEQ ID NO 11
<211> LENGTH: 2349
<212> TYPE: DNA
<213> ORGANISM: Bifidobacterium longum
<220> FEATURE:
<223> OTHER INFORMATION: Bifidobacterium longum subspecies infantis (B. infantis) strain ATCC 15697 = JCM 1222 = DSM 20088 glycoside hydrolase family 95 (GH95), afcA, Blon_2335

<400> SEQUENCE: 11

```
ctacctgcgg acaagcccct tgaacggctc gtcgggagac agtcggacct gcgtcgcgtc     60
ggtgccatcg acgatcaggg tgatcgtcgc gggcttcgtg cagcgcagcg tgtattcgat    120
ggcgtcgtcc gtccaggagg cgtccaccga aaggcctccc ctggcgcgca ggccatggaa    180
gctgccttca tgccaatcct cgggcaacgc gggcaggatg cgcaccatgc cgtcatgact    240
ctggacgagc atctccgcca gagccgcggg gaagcccaga ttgccgtcga tctggaatgg    300
gggatgcgcg cacatgccgc tggcatacac gccgccgcca agcagatcgg tttcggcgtc    360
ggcttcgacc gggcggagga acatgccgat gatgcgttcg gcgtgctcag cgtcccgcag    420
acgcgcccac atgatcatgc gccacacgat gctccagccg gaaccgtcgt cgccacgcac    480
ttcgagggac ttcctggcgg cctcctccag acgcggggtg ttcgcggtga tgcctgcgcc    540
cggatgcagt tcgtacaggt gggacaggtg acggtgatgc ggatccgcct cgacgagttc    600
atcgttccat tcgagaatcc tgccatcgga tcccacgcgg acagccgcca gcttcgcgcg    660
ggtggattcc gcctcccgca ccaaggcctt gtcgccgtca tccaggtcgg gcatggtttg    720
cgccgcgtgg atcagatcat cgagcagatt gcgcacgatg gccgtggtgt tttcgctggt    780
gtgggcgacg gcgatcgttt cgccgtccac gacgaagtag ttttccggcg atgtcgccgg    840
agccggggcc agaccgtgtt ccgtatccga cagaaaatcc atgcagaatc gcgcgctgtc    900
ccgcatgatc ggccagatgg aagccagata cgactcatcc tggttgaaca ggtactcatc    960
gaacaggttc cggcacatcc acgcctggcc gaacggccag aacgcccacg tcggctctcc   1020
gttcgccggc agcgccctgc gccagatatc gacattgtgg aagaccgcgg aaccaccgca   1080
tccgaggatg gcgccggccg catcatgccc cggttccagc agctccctgt tcatggcgac   1140
gagcggttcg atgagctcct tgagggcgca tgggccggtc atccaatagt tcatctcgat   1200
gttgatgttc gtcgtgtagg cgctatacca gttcgggaag tccttatggt tccagattcc   1260
ctgcagattc gacggctggg tatgcggcct ggacgaggag atcagcaggt atcgccgaa    1320
atcgaacatc gcctcggaga gcgtctccag acggtgcggc gtatcctcct ggagcgcag    1380
gatctcggcg aacggcacct cctcatcgtc gtcatgggcc gggccgagac gcacgccgac   1440
ccggtcgaag aaccgcggt agtcggcgac gtgacggtca agcatcgccc gcgaatcgga    1500
cggccatgcg gcgatggtct cgcccagccg atcggcgagc accgtcatgt cccgctccgg   1560
```

| | |
|---|---|
| ctgttcggcg cttcccttga acccgctcag gctgcggaac cgaagcgaca agccggtgac | 1620 |
| gcccgagcac tgcagaacat catcgatcac cgtgatctcg ccgcccgtga cggtgaggga | 1680 |
| gaaggcgccg gcatacgcca tcccgatgcc gtcccgttcg tcctcccatg gattatcggt | 1740 |
| gacatgggcc aatgatccga cattgagtcc gggcatctgc cccatgacga cgagggtggc | 1800 |
| ctggcgcgca tcggaatcag accccgacga tatccgggtc tgcttgagaa aagtgccggt | 1860 |
| gacgctcacg ctcgcatcga ccggcgcgct cgacgacatc tcatacacca gcagatcatc | 1920 |
| gggagcgctg caccatgcgt cgacatggac gtcggcggcg cccagccgga acgattcgcc | 1980 |
| ggcgagggcc ctggcgaggt ccaggctgcg cttcacatgc ttccgttcgc cggcctccga | 2040 |
| cgagtaccgg atgcaagccg tgccgaacgg ctcgtatatc tgctcgtcct tctcccgctg | 2100 |
| cgtggcgtcc tggatgatcc gcgtggccga cacgtaatcg ccgcgagacg acgcctgacg | 2160 |
| ggctttggcc acgatttcgg gcgtcaacgg cgaggtctcc gcatgcggat agcccgacca | 2220 |
| gagggtgtcg tcgttgaggt acagcacatc cgcgtccggt tcggagcaca ggaccgcccc | 2280 |
| catgcgaccg ttgccgaacg ggattccttc ctcccaatgc gaagaaatcc catcgaaagt | 2340 |
| gagtttcat | 2349 |

<210> SEQ ID NO 12
<211> LENGTH: 6120
<212> TYPE: DNA
<213> ORGANISM: Bifidobacterium bifidum
<220> FEATURE:
<223> OTHER INFORMATION: Bifidobacterium bifidum strain JCM 1254 alpha-
      fucosidase, glycoside hydrolase family 95 (GH95), afcA

<400> SEQUENCE: 12

| | |
|---|---|
| aacggtatcc agggactctc tgagagctgt ggttccaatt gaagacacaa gtcgccgacg | 60 |
| gacttgattc ttttagtaaa caatgtatat attaatatga accggcaaag ctgctggctg | 120 |
| tcctatagga gaaagaacca aatatgaaac atagagcgat gtcatcgcgt ctgatgccac | 180 |
| tggtggcgtc ctgcgcgacg gtcggcatgc tgctggccgg actacctgtg tcggccgtcg | 240 |
| cggtcggcac gacgagagcg gcagcgtccg acgcctcgtc ctccaccaca gcaaccatca | 300 |
| ccccctccgc cgataccacg ttgcagacat ggacgagcga gaagaattcc tcaatggcgt | 360 |
| ccaagccgta catcggcaca ctgcaagggc cctcgcaagg cgtgttcggc gagaagttcg | 420 |
| agtccacgga tgccgcggac accaccgatc tgaagaccgg cctgctgacg ttcgacctga | 480 |
| gcgcctacga ccatgcccccc gattccgcaa cgttcgagat gacgtacctc ggctaccgcg | 540 |
| gcaacccgac ggccaccgac accgacacca tcaaggtgac ccccgtcgac accaccgtgt | 600 |
| gcaccaataa cgccacagac tgcggcgcga atgtcgcgac cggcgcgacc aagccgaagt | 660 |
| tcagcatcaa cgactcctca ttcgtcgccg agtccaagcc gttcgagtac ggtacgacgg | 720 |
| tttacacggg cgacgccatc accgtggttc ccgccaatac caagaaggtc accgtagatg | 780 |
| tgaccgaaat cgtgcgccag cagttcgccg aaggcaagaa ggtcatcacc ctggccgtgg | 840 |
| gcgagaccaa gaagaccgag gttcgtttcg ccagttccga aggcacgacg tccctgaacg | 900 |
| gcgcgaccgc agacatggct ccgaagctga ccgtttccgt gtccaccaag gacgatctca | 960 |
| agccctccgc cgacaccacg ttgcaggcat gggccagcga gaagaacgag aagaagaaca | 1020 |
| ctgcggccta tgtcgcgcg ctgcagccgg aaggcgatta cggcgacttc ggtgagaagt | 1080 |
| tcaagtccac cgacgtccac gatgtcacag acgccaagat gggtctgatg acgttcgacc | 1140 |
| tgtccgatta caccgcggcg cccgagcact ccatcctcac cttgacgtat ctgggctacg | 1200 |

```
ccggtgcaga caagaccgcc acggccaccg ataaggtcaa ggtggtcgct gttgacacgt   1260
cgcggtgcac cggcaccgct ccctgcgaca ccaacaatgc cacgtgggcg aaccgcccgg   1320
acttcgaggt gaccgatacc acgaagaccg cgacgtccca tgcgttcgct tatggatcta   1380
agaagtattc cgatggcatg accgtcgaat cgggcaacgc caagaaggtc ctgctcgacg   1440
tgtccgatgt catcaaggca gagttcgcca agttcagcgc cggcgccacc gagaagaaga   1500
tcacgctggc cctgggcgag ctcaacaagt ccgacatgcg tttcggcagc aaggaagtca   1560
cctcgctgac cggcgccacc gaagccatgc agccgacctt gtccgtcacc aagaagccga   1620
aggcatacac gctgagcatc gaaggcccga ccaaggtcaa gtaccagaag ggcgaggcgt   1680
tcgacaaggc cggactcgtg gtcaaggcca ccagcacggc tgacggcacg gtcaagacgc   1740
tgaccgaagg caacggtgag gataactaca ccatcgacac cagcgctttc gatagtgcca   1800
gcatcggcgt ataccctgtt accgtgaagt acaacaagga ccccgaaatc gccgcttcgt   1860
tcaacgccta tgtcatcgcc agtgtcgagg acggcggaga cggcgacacc agcaaagacg   1920
actggctgtg gtacaagcag cccgcgtcgc agaccgacgc caccgccacc gccggcggca   1980
attacggcaa ccccgacaac aaccgttggc agcagaccac cttgccgttc ggcaacggca   2040
agatcggcgg caccgtctgg ggcgaggtca gccgtgaacg cgtcaccttc aacgaggaga   2100
cgctgtggac cggcggcccc ggatcctcga ccagctacaa cggcggcaac aacgagacca   2160
agggtcagaa cggcgccacg ctgcgcgcgc tcaacaagca gctcgcgaac ggcgccgaga   2220
cggtcaatcc cggcaacctg accggcgcg agaacgcggc cgagcagggc aactacctga   2280
actggggcga catctacctc gactacgggt tcaacgatac gaccgtcacc gaataccgcc   2340
gcgacctgaa cctgagcaag ggcaaggccg acgtcacgtt caagcatgac ggcgtcacct   2400
acacgcgcga atacttcgcg tcgaaccccg acaatgtcat ggtcgcccgc tcacggcca   2460 gcaaagccgg caagctgaac ttcaacgtca gcatgccgac caacacgaac tactccaaga   2520
ccggcgaaac cacgacggtc aagggtgaca cgctcaccgt caagggcgct ctcggcaaca   2580
acggcctgct gtacaactcg cagatcaagg tcgtcctcga caacggtgag ggcacgctct   2640
ccgaaggctc cgacggcgct tcgctgaagg tctccgacgc gaaggcggtc acgctgtaca   2700
tcgccgccgc gacggactac aagcagaagt atccgtccta ccgcaccggc gaaaccgccg   2760
ccgaggtgaa caccccgcgtc gccaaggtcg tgcaggacgc cgccaacaag ggctacaccg   2820
ccgtcaagaa agcgcacatc gacgatcatt ccgccatcta cgaccgcgtg aagatcgatt   2880
tgggccagtc cggccacagc tccgacggcg ccgtcgccac cgacgcgctg ctcaaggcgt   2940
accagagagg ctccgcaacc accgcgcaga agcgcgagct ggagacgctg gtgtacaagt   3000
acggccgcta cttgaccatc ggctcctccc gtgagaacag ccagctgccc agcaacctgc   3060
agggcatctg gtcggtcacc gcgggcgaca acgcccacgg caacacgcct tggggctccg   3120
acttccacat gaacgtgaac ctccagatga actactggcc gacctattcg ccaacatgg    3180 gagagctcgc cgagccgctc atcgagtatg tggagggtct ggtcaagccc ggccgtgtga   3240
ccgccaaggt ctacgcgggc gcggagacga cgaaccccga ccacgccg atcggcgagg    3300 gcgagggcta catggcccac accgagaaca ccgcctacgc ctggaccgca cccggtcaat   3360
cgttctcgtg gggttggagc ccggccgccg tgccgtggat cctgcagaac gtgtacgagg   3420
cgtacgagta ctccggcgac cctgccctgc ttgatcgcgt gtacgcgctg ctcaaggagg   3480
aatcgcactt ctacgtcaac tacatgctgc acaaggccgg ctccagctcc ggtgaccgcc   3540
```

```
tgactaccgg cgtcgcgtac tcgcccgaac agggcccgct gggcaccgac ggcaacacgt   3600
acgagagctc gctcgtgtgg cagatgctca acgacgccat cgaggcggcc aaggccaagg   3660
gagatccgga cggtctggtc ggcaatacca ccgactgctc ggccgacaac tgggccaaga   3720
atgcagcgg caacttcacc gatgcgaacg ccaaccgttc ctggagctgc gccaagagcc   3780
tgctcaagcc gatcgaggtc ggcgactccg gccagatcaa ggaatggtac ttcgaaggtg   3840
cgctcggcaa gaagaaggat ggatccacca tcagcggcta ccaggcggac aaccagcacc   3900
gtcacatgtc ccacctgctc ggactgttcc ccggtgattt gatcaccatc gacaactccg   3960
agtacatgga tgcggccaag acctcgctga ggtaccgctg cttcaagggc aacgtgctgc   4020
agtccaacac cggctgggcc attggccagc gcatcaattc gtgggctcgc accggcgacg   4080
gcaacaccac gtaccagctg gtcgagctgc agctcaagaa cgcgatgtat gcaaacctgt   4140
tcgattacca tgcgccgttc cagatcgacg gcaacttcgg caacacctcc ggtgtcgacg   4200
aaatgctgct gcagtccaac tccaccttca ccgacaccgc cggcaagaag tacgtgaact   4260
acacgaacat cctgcccgcc ctgccgatg cctgggcggg cggctcggtg agcggcctcg   4320
tggcccgcgg caacttcacc gtcggcacga catggaagaa cggcaaggcc accgaagtca   4380
ggctgacctc caacaagggc aagcaggcgg ccgtcaagat caccgccggc ggcgcccaga   4440
actacgaggt caagaacggt gacaccgccg tgaacgccaa ggtcgtgacc aacgcggacg   4500
gcgcctcgct gctcgtgttc gataccaccg caggcaccac gtacgcgatc acgaagaagg   4560
cgagcgccaa cgtgcccgtc accggcgtga ccgtgaccgg cgccaacacc gccaccgcag   4620
gcgacaccgt cactcttacg gctaccgtcg cccggccaa tgcgaccgac aagtccgtca   4680
cctggtcgac ctccgacgcc gccgtagcta cggtcaacgc caacggcgtg gtgaccacga   4740
agaaggccgg caaggtgacc atcaccgcca cgtcgaacgg cgacaagacg aagttcggtt   4800
ccatcgagat caccgtctcc gccgcgaccg tgcccgtcac cagcgtcacc gttgccggcg   4860
acgccgcgat gaccgtcgat ggagagcaga ccctgacggc gaccgtcgcc ccggccactg   4920
cgaccgacaa gacggtcacg tggaagtcct ccgacgccac tgtggcgacg gttgacgcca   4980
acggcaaggt cgtcgcgaag aaggccggcg aagtgacgat caccgccacg gccggtggcg   5040
tgtccggcac gctgaagatc acggtgagcg acaaggcccc gaccgtcatc ccggtccagt   5100
ccgtgaccgt gacaggcaag caggagctcg tcgaaggcgc ctccacgacc ctgacggcga   5160
ccgtcgcccc ggctgacgcg accgacaaga cggttacgtg gaagtcgagc gacgagtccg   5220
tcgccacggt cgacaaggac ggcgtcgtga ccgccaagaa ggccggcacg gtgaccatca   5280
ccgccacggc cggtggcgtg tccggcacgc tccacatcac cgtgacggcc aagcccgtcg   5340
agaccgtccc cgtcaccagc gtggaggtca ccgtcgaggc cggcaccacc gtctccgtcg   5400
gcaagacact ccaggccacc gcgaccgtca agcccggcaa cgccaccaac aagaaggtga   5460
cgtggaagtc gagcgacgaa tccatcgcga cggtcgacgc caacggcgtc atcaccgcga   5520
agaaggccgg caaggtcgtc atcacggcca cctcgaccga cggcacggac aagtccggca   5580
gcgtcgagat caccgtcgtg gatgagacca agccgacgcc cgaccacaag tccgtcaagg   5640
ccgataccgg cgacgtgacc gccggcaaga ccggtacggt caccgagccg aaggacgtgg   5700
cgggctggaa gagccgctcc atcatcaagc aaggcaagct cggcaaggcc gaaatcgccg   5760
acggcacgct cgtgtatgcg gccgcgacga agaccggtga cgacagcttc gtcgtgcagt   5820
acacgatggc cgacggcacg gtcatcgacg tgacctacag cgtcacggtc aaggccgccg   5880
aaaccggcaa gaacgacggc gacggcaagg gcgacggtgt cgcgaagacc ggcgccgccg   5940
```
tcggcgcgct cgccggcctc ggcttgatgc tgctcgccgt cggagtgagc gtggtgatga    6000
ttcgccgcaa gcactccgcc tgatccccag tcagaccggc cagtcgtgac cggtcggcct    6060
gactgactct ttctccaccg tccccgtcg gataaacccc ggcgggggac ggtggcttgt    6120

<210> SEQ ID NO 13
<211> LENGTH: 20
<212> TYPE: DNA
<213> ORGANISM: Artificial Sequence
<220> FEATURE:
<223> OTHER INFORMATION: synthetic 16SrDNA universal PCR amplification
      primer 27F

<400> SEQUENCE: 13
agagtttgat cctggctcag                                                  20

<210> SEQ ID NO 14
<211> LENGTH: 19
<212> TYPE: DNA
<213> ORGANISM: Artificial Sequence
<220> FEATURE:
<223> OTHER INFORMATION: synthetic 16SrDNA universal PCR amplification
      primer 1492R

<400> SEQUENCE: 14
tacggttacc ttgttacga                                                   19

<210> SEQ ID NO 15
<211> LENGTH: 21
<212> TYPE: DNA
<213> ORGANISM: Artificial Sequence
<220> FEATURE:
<223> OTHER INFORMATION: synthetic multilocus sequence typing (MLST) PCR
      forward primer

<400> SEQUENCE: 15
gagtaccgca agtacatcga g                                                21

<210> SEQ ID NO 16
<211> LENGTH: 23
<212> TYPE: DNA
<213> ORGANISM: Artificial Sequence
<220> FEATURE:
<223> OTHER INFORMATION: synthetic multilocus sequence typing (MLST) PCR
      reverse primer

<400> SEQUENCE: 16
catcctcatc gtcgaacagg aac                                              23

<210> SEQ ID NO 17
<211> LENGTH: 20
<212> TYPE: DNA
<213> ORGANISM: Artificial Sequence
<220> FEATURE:
<223> OTHER INFORMATION: synthetic multilocus sequence typing (MLST) PCR
      forward primer

<400> SEQUENCE: 17
cattcgaact ccgacaccga                                                  20

<210> SEQ ID NO 18
<211> LENGTH: 18
<212> TYPE: DNA
<213> ORGANISM: Artificial Sequence
<220> FEATURE:
<223> OTHER INFORMATION: synthetic multilocus sequence typing (MLST) PCR reverse primer

<400> SEQUENCE: 18
gtggggtagt cgccgttg                                               18

<210> SEQ ID NO 19
<211> LENGTH: 24
<212> TYPE: DNA
<213> ORGANISM: Artificial Sequence
<220> FEATURE:
<223> OTHER INFORMATION: synthetic multilocus sequence typing (MLST) PCR
      forward primer

<400> SEQUENCE: 19
agctgcacgc bggcggcaag ttcg                                        24

<210> SEQ ID NO 20
<211> LENGTH: 24
<212> TYPE: DNA
<213> ORGANISM: Artificial Sequence
<220> FEATURE:
<223> OTHER INFORMATION: synthetic multilocus sequence typing (MLST) PCR
      reverse primer

<400> SEQUENCE: 20
gttgccgagc ttggtcttgg tctg                                        24

<210> SEQ ID NO 21
<211> LENGTH: 24
<212> TYPE: DNA
<213> ORGANISM: Artificial Sequence
<220> FEATURE:
<223> OTHER INFORMATION: synthetic multilocus sequence typing (MLST) PCR
      forward primer

<400> SEQUENCE: 21
atcggcatca tggcycacat ygat                                        24

<210> SEQ ID NO 22
<211> LENGTH: 22
<212> TYPE: DNA
<213> ORGANISM: Artificial Sequence
<220> FEATURE:
<223> OTHER INFORMATION: synthetic multilocus sequence typing (MLST) PCR
      reverse primer

<400> SEQUENCE: 22
ccagcatcgg ctgmacrccc tt                                          22

<210> SEQ ID NO 23
<211> LENGTH: 21
<212> TYPE: DNA
<213> ORGANISM: Artificial Sequence
<220> FEATURE:
<223> OTHER INFORMATION: synthetic multilocus sequence typing (MLST) PCR
      forward primer

<400> SEQUENCE: 23
atcccgcgyt accagacsat g                                           21

<210> SEQ ID NO 24
<211> LENGTH: 20
<212> TYPE: DNA
<213> ORGANISM: Artificial Sequence
<220> FEATURE:
<223> OTHER INFORMATION: synthetic multilocus sequence typing (MLST) PCR
      reverse primer

```
<400> SEQUENCE: 24
cggtgtcgac gtagtcggcg                                                    20

<210> SEQ ID NO 25
<211> LENGTH: 24
<212> TYPE: DNA
<213> ORGANISM: Artificial Sequence
<220> FEATURE:
<223> OTHER INFORMATION: synthetic multilocus sequence typing (MLST) PCR
      forward primer

<400> SEQUENCE: 25
ggacaaggac ggcrtsccsg ccaa                                               24

<210> SEQ ID NO 26
<211> LENGTH: 24
<212> TYPE: DNA
<213> ORGANISM: Artificial Sequence
<220> FEATURE:
<223> OTHER INFORMATION: synthetic multilocus sequence typing (MLST) PCR
      reverse primer

<400> SEQUENCE: 26
acgaccrccg tgcgggtgrt cgac                                               24

<210> SEQ ID NO 27
<211> LENGTH: 20
<212> TYPE: DNA
<213> ORGANISM: Artificial Sequence
<220> FEATURE:
<223> OTHER INFORMATION: synthetic multilocus sequence typing (MLST) PCR
      forward primer

<400> SEQUENCE: 27
ggcgagctga tccagaacca                                                    20

<210> SEQ ID NO 28
<211> LENGTH: 20
<212> TYPE: DNA
<213> ORGANISM: Artificial Sequence
<220> FEATURE:
<223> OTHER INFORMATION: synthetic multilocus sequence typing (MLST) PCR
      reverse primer

<400> SEQUENCE: 28
gcatcctcgt agttgtascc                                                    20

<210> SEQ ID NO 29
<211> LENGTH: 18
<212> TYPE: DNA
<213> ORGANISM: Artificial Sequence
<220> FEATURE:
<223> OTHER INFORMATION: synthetic qPCR degenerate amplification primer
      Blon_2335F

<400> SEQUENCE: 29
garatgaayt aytggatg                                                      18

<210> SEQ ID NO 30
<211> LENGTH: 23
<212> TYPE: DNA
<213> ORGANISM: Artificial Sequence
<220> FEATURE:
<223> OTHER INFORMATION: synthetic qPCR degenerate amplification primer
      Blon_2335R
<220> FEATURE:
```

```
<221> NAME/KEY: modified_base
<222> LOCATION: (1)...(23)
<223> OTHER INFORMATION: n = g, a, c or t

<400> SEQUENCE: 30
ttnccrtcda tytgraangg ngg                                              23

<210> SEQ ID NO 31
<211> LENGTH: 20
<212> TYPE: DNA
<213> ORGANISM: Artificial Sequence
<220> FEATURE:
<223> OTHER INFORMATION: synthetic qPCR degenerate amplification primer
      Blon_2336F
<220> FEATURE:
<221> NAME/KEY: modified_base
<222> LOCATION: (15)...(15)
<223> OTHER INFORMATION: n = g, a, c or t

<400> SEQUENCE: 31
aarcaycayg ayggnttytg                                                  20

<210> SEQ ID NO 32
<211> LENGTH: 17
<212> TYPE: DNA
<213> ORGANISM: Artificial Sequence
<220> FEATURE:
<223> OTHER INFORMATION: synthetic qPCR degenerate amplification primer
      Blon_2336R
<220> FEATURE:
<221> NAME/KEY: modified_base
<222> LOCATION: (1)...(17)
<223> OTHER INFORMATION: n = g, a, c or t

<400> SEQUENCE: 32
acytcngcng grtacca                                                     17

<210> SEQ ID NO 33
<211> LENGTH: 15
<212> TYPE: DNA
<213> ORGANISM: Artificial Sequence
<220> FEATURE:
<223> OTHER INFORMATION: synthetic qPCR degenerate amplification primer
      Blon_0248/0426F
<220> FEATURE:
<221> NAME/KEY: modified_base
<222> LOCATION: (6)...(6)
<223> OTHER INFORMATION: n = g, a, c or t

<400> SEQUENCE: 33
taygcngart ggtay                                                       15

<210> SEQ ID NO 34
<211> LENGTH: 17
<212> TYPE: DNA
<213> ORGANISM: Artificial Sequence
<220> FEATURE:
<223> OTHER INFORMATION: synthetic qPCR degenerate amplification primer
      Blon_0248/0426R
<220> FEATURE:
<221> NAME/KEY: modified_base
<222> LOCATION: (1)...(17)
<223> OTHER INFORMATION: n = g, a, c or t

<400> SEQUENCE: 34
tcrtgrtgyt tngtngt                                                     17

<210> SEQ ID NO 35
<211> LENGTH: 17
```

```
<212> TYPE: DNA
<213> ORGANISM: Artificial Sequence
<220> FEATURE:
<223> OTHER INFORMATION: synthetic qPCR degenerate amplification primer
      Blon_0346F
<220> FEATURE:
<221> NAME/KEY: modified_base
<222> LOCATION: (1)...(17)
<223> OTHER INFORMATION: n = g, a, c or t

<400> SEQUENCE: 35
ytngayttyc ayacnws                                                  17

<210> SEQ ID NO 36
<211> LENGTH: 17
<212> TYPE: DNA
<213> ORGANISM: Artificial Sequence
<220> FEATURE:
<223> OTHER INFORMATION: synthetic qPCR degenerate amplification primer
      Blon_0346R
<220> FEATURE:
<221> NAME/KEY: modified_base
<222> LOCATION: (1)...(17)
<223> OTHER INFORMATION: n = g, a, c or t

<400> SEQUENCE: 36
tcrtgrtgyt tngtngt                                                  17

<210> SEQ ID NO 37
<211> LENGTH: 17
<212> TYPE: DNA
<213> ORGANISM: Artificial Sequence
<220> FEATURE:
<223> OTHER INFORMATION: synthetic qPCR degenerate amplification primer
      Blon_2348F
<220> FEATURE:
<221> NAME/KEY: modified_base
<222> LOCATION: (1)...(17)
<223> OTHER INFORMATION: n = g, a, c or t

<400> SEQUENCE: 37
athacngcng ayathac                                                  17

<210> SEQ ID NO 38
<211> LENGTH: 20
<212> TYPE: DNA
<213> ORGANISM: Artificial Sequence
<220> FEATURE:
<223> OTHER INFORMATION: synthetic qPCR degenerate amplification primer
      Blon_2348R
<220> FEATURE:
<221> NAME/KEY: modified_base
<222> LOCATION: (1)...(20)
<223> OTHER INFORMATION: n = g, a, c or t

<400> SEQUENCE: 38
tcnacnacyt trttytcrtc                                               20

<210> SEQ ID NO 39
<211> LENGTH: 20
<212> TYPE: DNA
<213> ORGANISM: Artificial Sequence
<220> FEATURE:
<223> OTHER INFORMATION: synthetic qPCR amplification primer Blon_0646F

<400> SEQUENCE: 39
ccaccagaca tggaacagtg                                               20

<210> SEQ ID NO 40
```

-continued

```
<211> LENGTH: 20
<212> TYPE: DNA
<213> ORGANISM: Artificial Sequence
<220> FEATURE:
<223> OTHER INFORMATION: synthetic qPCR amplification primer Blon_0646R

<400> SEQUENCE: 40
aaatcgccga aggtgatatg                                               20

<210> SEQ ID NO 41
<211> LENGTH: 20
<212> TYPE: DNA
<213> ORGANISM: Artificial Sequence
<220> FEATURE:
<223> OTHER INFORMATION: synthetic qPCR amplification primer Blon_0459F

<400> SEQUENCE: 41
ccccaccctc gactggctca                                               20

<210> SEQ ID NO 42
<211> LENGTH: 17
<212> TYPE: DNA
<213> ORGANISM: Artificial Sequence
<220> FEATURE:
<223> OTHER INFORMATION: synthetic qPCR amplification primer Blon_459R

<400> SEQUENCE: 42
cttcgaggtg gcacagg                                                  17

<210> SEQ ID NO 43
<211> LENGTH: 20
<212> TYPE: DNA
<213> ORGANISM: Artificial Sequence
<220> FEATURE:
<223> OTHER INFORMATION: synthetic qPCR amplification primer 0248WF

<400> SEQUENCE: 43
accaacaacc agcaaccaat                                               20

<210> SEQ ID NO 44
<211> LENGTH: 20
<212> TYPE: DNA
<213> ORGANISM: Artificial Sequence
<220> FEATURE:
<223> OTHER INFORMATION: synthetic qPCR amplification primer 0248WR

<400> SEQUENCE: 44
atcgaatacg gcaccttcag                                               20

<210> SEQ ID NO 45
<211> LENGTH: 20
<212> TYPE: DNA
<213> ORGANISM: Artificial Sequence
<220> FEATURE:
<223> OTHER INFORMATION: synthetic qPCR amplification primer 0426WF

<400> SEQUENCE: 45
accaacaacc agcaaccaat                                               20

<210> SEQ ID NO 46
<211> LENGTH: 20
<212> TYPE: DNA
<213> ORGANISM: Artificial Sequence
<220> FEATURE:
<223> OTHER INFORMATION: synthetic qPCR amplification primer 0426WR

<400> SEQUENCE: 46
```
gaccgccttc atggataaga                                              20

<210> SEQ ID NO 47
<211> LENGTH: 20
<212> TYPE: DNA
<213> ORGANISM: Artificial Sequence
<220> FEATURE:
<223> OTHER INFORMATION: synthetic qPCR amplification primer RNP-F

<400> SEQUENCE: 47
aacctgatga tcggacgacg                                              20

<210> SEQ ID NO 48
<211> LENGTH: 20
<212> TYPE: DNA
<213> ORGANISM: Artificial Sequence
<220> FEATURE:
<223> OTHER INFORMATION: synthetic qPCR amplification primer RNP-R

<400> SEQUENCE: 48
ggcaaactgc tcatccaacg                                              20

<210> SEQ ID NO 49
<211> LENGTH: 20
<212> TYPE: DNA
<213> ORGANISM: Artificial Sequence
<220> FEATURE:
<223> OTHER INFORMATION: synthetic qPCR amplification primer GH29-F

<400> SEQUENCE: 49
ggactgaagt tcggcgtgta                                              20

<210> SEQ ID NO 50
<211> LENGTH: 20
<212> TYPE: DNA
<213> ORGANISM: Artificial Sequence
<220> FEATURE:
<223> OTHER INFORMATION: synthetic qPCR amplification primer GH29-R

<400> SEQUENCE: 50
tcgttgtcct cctccgagat                                              20

<210> SEQ ID NO 51
<211> LENGTH: 20
<212> TYPE: DNA
<213> ORGANISM: Artificial Sequence
<220> FEATURE:
<223> OTHER INFORMATION: synthetic qPCR amplification primer GH95-F

<400> SEQUENCE: 51
cgcggactac cgcagatatt                                              20

<210> SEQ ID NO 52
<211> LENGTH: 20
<212> TYPE: DNA
<213> ORGANISM: Artificial Sequence
<220> FEATURE:
<223> OTHER INFORMATION: synthetic qPCR amplification primer GH95-R

<400> SEQUENCE: 52
atcgaacatt gcctctgcca                                              20